US007498292B2

(12) United States Patent
Suga et al.

(10) Patent No.: US 7,498,292 B2
(45) Date of Patent: Mar. 3, 2009

(54) COMBINATORIAL LIBRARIES OF AUTOINDUCER ANALOGS, AUTOINDUCER AGONISTS AND ANTAGONISTS, AND METHODS OF USE THEREOF

(75) Inventors: Hiroaki Suga, Williamsville, NY (US); Yigong Bu, Troy, NY (US)

(73) Assignee: The Research Foundation of State University of New York, Amherst, NY (US)

( * ) Notice: Subject to any disclaimer, the term of this patent is extended or adjusted under 35 U.S.C. 154(b) by 0 days.

(21) Appl. No.: 10/637,940

(22) Filed: Aug. 8, 2003

(65) Prior Publication Data
US 2004/0115732 A1 Jun. 17, 2004

Related U.S. Application Data

(60) Provisional application No. 60/403,791, filed on Aug. 15, 2002.

(51) Int. Cl.
*C40B 40/02* (2006.01)
(52) U.S. Cl. .......................... 506/15; 514/561
(58) Field of Classification Search ........................ None
See application file for complete search history.

(56) References Cited

U.S. PATENT DOCUMENTS

| 6,395,282 B1 | 5/2002 | Kende et al. |
| 6,559,176 B1 | 5/2003 | Bassler et al. |

FOREIGN PATENT DOCUMENTS

| CA | 2328831 A1 | 7/2002 |
| WO | 99/65889 A1 | 12/1999 |
| WO | WO 01/85664 | 11/2001 |
| WO | 01/94543 A2 | 12/2001 |
| WO | 02/18342 A2 | 3/2002 |

OTHER PUBLICATIONS

Winson et al. "Multiple N-acyl-L-homoserine lactone signal molecules regulate production of virulence determinants and secondary metabolites in *Pseudomonas aeruginosa*" Proc. Natl. Acad. Sci. USA 1995, 92, 9427-9431.*
Mndzhoan et al., Biol. Svioistva Khim. Soedin., Akad. Nauk Arm. SSR, Inst. Tonkoi Organ. Khim. 1962, 1, 219-233.*
Mndzhoyan et al., "Effect of organic acids of pyridyl and thiazolylamides on certain members of coli-typhosal, staphylococcal, streptococcal groups and on acid-resistant mycobacteria" Biol. Svioistva Khim. Soedin., Akad. Nauk Arm. SSR, Inst. Tonkoi Organ. Khim. 1962, 1, 219-233 (1-21 for English translation).*
(Buchi, J. "The Constitution-Effect Relationships from a New Viewpoint" Deutsche Apotheker-Zeitung 1966, pp. 1695-1700 (1-29 for English translation).*
Smith et al. "Library Screening for Synthetic Agonists and Antagonists of a *Pseudomonas aeruginosa* Autoinducer" Chemistry & Biology Jun. 2003, vol. 10, pp. 563-571.*

Kato et al., "Antitumor activity of compounds derived from diketone and their related compounds" Yakugaku Zasshi 1997, 97(6), 676-84.*
Buchi, J. "The Constitution-Effect Relationships from a New Viewpoint" Deutsche Apotheker-Zeitung 1966, pp. 1695-1700 (1-29 for English translation).*
Smith et al., "Induction and Inhibition of *Pseudomonas aeruginosa* Quorum Sensing by Synthetic Autoinducer Analogs," Chemistry & Biology, 10:81-89 (2003).
Smith et al., "Library Screening for Synthetic Agonists and Antagonists of a *Pseudomonas aeruginosa* Autoinducer," Chemistry & Biology, 10:563-571 (2003).
Bu et al., "Design and Synthesis of Autoinducer Analogs for the Interruption of the Quorum-Sensing in *Pseudomonas aeruginosa*," Abstracts of Papers, 224th ACS National Meeting, (Aug. 18-22, 2002) (abstract).
Bu et al., "Discovery of Antagonists of Quorum Sensing in *Pseudomonas aeruginosa* by Combinatorial Chemistry and High-Throughput Screening," Abstracts of Papers, 224th ACS National Meeting (Aug. 18-22, 2002) (abstract).
Bu, "Design and Synthesis of Autoinducer Analogs: Toward the Discovery of Antagonists of Quorum Sensing in *Pseudomanas aeruginosa*" Ph.D. Dissertation, State University of New York at Buffalo (Jan. 31, 2003).
Kline et al., "Novel Synthetic Analogs of the *Pseudomonas* Autoinducer," Bioorganic & Medicinal Chemistry Letters, 9:3447-3452 (1999).
Olsen et al., "Synthesis of New 3- and 4-Substituted Analogs of Acyl Homoserine Lactone Quorum Sensing Autoinducers," Bioorganic & Medicinal Chemistry Letters, 12:325-328 (2002).
Reverchon et al., "New Synthetic Analogues of N-Acyl Homoserine Lactones as Agonists or Antagonists of Transcriptional Regulators Involved in Bacterial Quorum Sensing," Bioorganic & Medicinal Chemistry Letters, 12:1153-1157 (2002).
Manefield et al., "Halogenated Furanones from the Red Alga, *Delisea pulchra*, Inhibit Carbapenem Antibiotic Synthesis and Exoenzyme Virulence Factor Production in the Phytopathogen *Erwinia carotovora*," FEMS Microbiology Letters, 205:131-138 (2001).
Pearson et al., "Roles of *Pseudomonas aeruginosa las* and *rhl* Quorum-Sensing Systems In Control of Elastase and Rhamnolipid Biosynthesis Genes," Journal of Bacteriology, 179:5756-5767 (1997).

(Continued)

*Primary Examiner*—J D Schultz
*Assistant Examiner*—Jeffrey S. Lundgren
(74) *Attorney, Agent, or Firm*—Nixon Peabody LLP

(57) ABSTRACT

The present invention relates to solid phase or solution phase combinatorial libraries of autoinducer analogs. The present invention also relates to autoinducer agonists and antagonists. In addition, the present invention relates to methods for identifying autoinducer agonists and antagonists, as well as methods for regulating the activity of an autoinducer receptor, regulating biofilm formation, regulating growth or virulence of an organism in a subject, inhibiting the quorum sensing mechanism of an organism, and treating an infection in a subject caused by an organism possessing a quorum sensing mechanism which use the autoinducer analogs of the present invention.

4 Claims, 21 Drawing Sheets

OTHER PUBLICATIONS

Schaefer et al., "Quorum Sensing in *Vibrio fischeri*: Probing Autoinducer-LuxR Interactions with Autoinducer Analogs," *Journal of Bacteriology*, 178:2897-2901 (1996).

Passador et al., "Functional Analysis of the *Pseudomonas aeruginosa* Autoinducer PAI," *Journal of Bacteriology*, 178:5995-6000 (1996).

Manefield et al., "Evidence that Halogenated Furanomes from *Delisea pulchra* Inhibit Acylated Homoserine Lactone (AHL)-Mediated Gene Expression by Displacing the Signal from its Receptor Protein," *Microbiology*, 145:283-291 (1999).

Hentzer et al., "Inhibition of Quorum Sensing in *Pseudomonas aeruginosa* Biofilm Bacteria by a Halogenated Furanone Compound," *Microbiology*, 148:87-102 (2002).

Pearson et al., "Structure of the Autoinducer Required for Expression of *Pseudomonas aeruginosa* Virulence Genes," *Proc. Natl. Acad Sci. USA*, 91:197-201 (1994).

Pearson et al., "A second N-acylhomoserine Lactone Signal Produced by *Pseudomonas aeruginosa*," *Proc. Natl. Acad. Sci. USA*, 92:1490-1494 (1995).

Pesci et al., "Quinolone Signaling in the Cell-to-Cell Communication System of *Pseudomonas aeruginosa*," 96:11229-11234 (1999).

Suga et al., "Molecular Mechanisms of Bacterial Quorum Sensing as a New Drug Target," *Current Opinion in Chemical Biology*, 7:586-591 (2003).

Zhang et al., "Structure of a Bacterial Quorum-Sensing Transcription Factor Complexed With Pheromone and DNA," *Nature*, 417:971-974 (2002).

Passador et al., "Expression of *Pseudomonas aeruginosa* Virulence Genes Requires Cell-to-Cell Communication," *Science*, 260:1127-1130 (1993).

Eberhard et al., "Analogs of the Autoinducer of Bioluminescence in *Vibrio fischeri*," *Arch. Microbiol.*, 146:35-40 (1986).

De Kievit et al., "Quorum-Sensing Genes in *Pseudomonas aeruginosa* Biofilms: Their Role and Expression Patterns," *Applied and Environmental Microbiology*, 67:1865-1873 (2001).

Bu et al., "The Synthesis and Biological Assay of a Library of autoinducer analogs of *Pseudomonas Aeruginosa*," *Buffalo International Symposium on Bioorganic Reaction Mechanisms*, Buffalo, New York (Aug. 15-17, 2002).

Glansdorp et al., "Synthesis and Stability of Small Molecule Probes for *Pseudomonas aeruginosa* Quorum Sensing Modulation," *Org. Biomol. Chem.* 2(22):3329-3336 (2004).

Vannini et al., "The Crystal Structure of the Quorum Sensing Protein TraR Bound to its Autoinducer and Target DNA," *EMBO J.* 21(17):4393-4401 (2002).

\* cited by examiner

Reagents and conditions: (a) n-BuLi, THF, -78 °C; undecenoyl chloride; (b) HOCH$_2$CH$_2$OH, p-TsOH, benzene, reflux. (c) BH$_3$.THF, THF; H$_2$O$_2$, NaHCO$_3$ aq, 38% for three steps (a–c); (d) DHP resin, PPTS, CH$_2$Cl$_2$, room temperature, 27 h; (e) LiOH in THF/H$_2$O, 75°C, 20 h. (f) parallel couplings with 94 amines and 2 alcohols (X), EDC, DMAP, DIPEA, DMF, room temperature, 72 h; (g) 95% TFA, room temperature, 30 min, R = CF$_3$CO or H.

Solid phase synthesis II. Reagents and conditions: (a) BH$_3$·THF, THF; H$_2$O$_2$, NaHCO$_3$ aq; (b) DHP resin, PPTS, CH$_2$Cl$_2$, room temperature, 27 h; (c) LiOH in THF/H$_2$O, 75°C, 20 h. (d) Meldrum's acid, DCC, DMAP, CH$_2$Cl$_2$, (e) parallel couplings with amines or alcohols (X), Et$_3$N, CH$_3$CN, reflux; (g) 95% TFA, room temperature, 30 min, R = CF$_3$CO or H.

COMBINATORIAL LIBRARIES OF AUTOINDUCER ANALOGS, AUTOINDUCER AGONISTS AND ANTAGONISTS, AND METHODS OF USE THEREOF

The present invention claims benefit of U.S. Provisional Application Ser. No. 60/403,791, filed Aug. 15, 2002, which is hereby incorporated by reference in its entirety.

FIELD OF THE INVENTION

The present invention relates to combinatorial libraries of autoinducer analogs, methods using such combinatorial libraries, autoinducer agonists and antagonists, and methods of use thereof.

BACKGROUND OF THE INVENTION

*Pseudomonas aeruginosa* is a ubiquitous gram-negative bacterium capable of infecting a wide variety of animals, plants, and insects (Rahme et al., *Science* 268:1899-1902 (1995)). *P. aeruginosa* is classified as an opportunistic pathogen because while it rarely causes disease in healthy people, it does infect people with impaired host defense systems that include cystic fibrosis (CF), cancer, AIDS, diabetes, deep burns, and wounds (Van Delden et al., *Emerg. Infect. Dis.* 4:551-560 (1998)). During infection, *P. aeruginosa* produces numerous virulence factors that cause tissue damage. In the case of CF, *P. aeruginosa* causes chronic, fatal lung infections in over 90% of patients (Hoiby, *Acta. Path. Microbiol. Scand. Sect. B* 82:551 (1974); Mahenthiralingam et al., *Infect Immun.* 62:596-605 (1994); Smith et al., *Cell* 85:229-236 (1996)). Although several anti-pseudomonal antibiotics, such as β-lactams, aminoglycosides and quinolones, are used in clinical drug regimens (Kovacs et al., *Infect. Med.* 15:467-472 (1998)), *P. aeruginosa* frequently develops resistance to these treatments (Oliver et al., *Science* 288:1251-1253 (2000)). Compounding the difficulty in eliminating the infection is the intrinsic ability of *P. aeruginosa* to develop a biofilm (Costerton et al., *Science* 284:1318-1322 (1999)). A biofilm is a complex, polysaccharide-laden microniche that protects the bacteria from both antibiotics and the host's humoral and cell-mediated responses.

Regulation of virulence factor production and biofilm development in *P. aeruginosa* is controlled by a sophisticated inter-cellular signaling mechanism responding to cell population density, known as quorum sensing (QS) (de Kievit et al., *Sci. Med.* November/December:42-50 (1999); Passador et al., *Science* 260:1127-1130 (1993); Passador et al., *J. Bacteriol.* 178:5995-6000 (1996); Hastings et al., *J. Bacteriol.* 181:2667-2668 (1999); Pesci et al., *Proc. Natl Acad. Sci. USA* 96:11229-11234 (1999); Parsek et al., *Proc. Natl Acad. Sci. USA* 97:8789-8793 (2000); Whiteley et al., *Proc. Natl Acad. Sci. USA* 96:13904-13909 (1999)). This regulatory circuit was first discovered in the marine bacterium *Vibrio fischeri* (Dunlap et al., *J. Bacteriol.* 164:45-50 (1985)), but later found in *P. aeruginosa* and many other bacteria (Hastings et al., *J. Bacteriol.* 181:2667-2668 (1999); de Kievit et al., *Infect. Immun.* 68:4839-5862 (2000)). The QS system generally consists of two families of proteins, R (regulator) and I (autoinducer synthase) proteins. The R proteins are known to activate transcription of both R and I genes that encode these protein families, as well as numerous downstream targets that include virulence factor and biofilm genes. In contrast, the I proteins are synthases of autoinducer signal molecules (vide infra). Importantly, the R protein is "activated" for DNA binding and transcriptional activation only upon binding to its cognate autoinducer (Gambello et al., *J. Bacteriol.* 173:3000-3009 (1991)), which is synthesized by the respective I protein. Therefore, as more autoinducers are produced by the I proteins, more activated R proteins exist in the system, which results in increased I protein levels. Thus, it is no coincidence that the signaling molecules are called autoinducers, because of the feedback role they play in QS. In *P. aeruginosa*, two R proteins, known as LasR and RhlR, and two I proteins, known as LasI and RhlI, have been identified (Passador et al., *Science* 260:1127-1130 (1993); Gambello et al., *J. Bacteriol.* 173:3000-3009 (1991); Ochsner et al., *J. Bacteriol.* 176:2044-2054 (1994); Ochsner et al., *Proc. Natl Acad. Sci. USA* 92:6424-6428 (1995)). Two autoinducers that bind to the respective R proteins have been identified, and are known as N-(3-oxododecanoyl)-L-homoserine lactone (3-oxo-$C_{12}$-HSL) (Pearson et al., *Proc. Natl Acad. Sci. USA* 91:197-201 (1994); Seed et al., *J. Bacteriol.* 177:654-659 (1995)) and N-butyloyl-L-homoserine lactone ($C_4$-HSL) (Pearson et al., *Proc. Natl Acad. Sci. USA* 92:1490-1494 (1995); Winson et al., *Proc. Natl Acad. Sci. USA* 92:9427-9431 (1995)). For simplicity, hereafter 3-oxo-$C_{12}$-HSL and $C_4$-HSL are called AI1 and AI2, respectively. By means of these diffusible autoinducers, the bacterial cells can monitor cell density in their immediate surroundings, and regulate gene expression accordingly.

While the las and rhl QS system consists of two separate regulons, their functions are apparently not independent. Even though both AI1-LasR and AI2-RhlR can activate transcription of lasB (which encodes the elastase (LasB) virulence factor), it has been shown that the las QS system controls the rhl QS system at both the transcriptional (Pearson et al., *J. Bacteriol.* 179:5756-5767 (1997)) and post-translational (Pesci et al., *J. Bacteriol.* 179:3127-3132 (1997)) levels. For example, as cell density increases, AI1 builds to a critical concentration, at which point it interacts with LasR (Passador et al., *Science* 260:1127-1130 (1993)). This AI1-LasR complex then activates transcription of a number of genes, such as lasB, toxA, rhlR, and lasI (Whiteley et al., *Proc. Natl Acad. Sci. USA* 96:13904-13909 (1999); Gambello et al., *J. Bacteriol.* 173:3000-3009 (1991); Pesci et al., *J. Bacteriol.* 179:3127-3132 (1997); Storey et al., *Infect. Immun.* 66:2521-2528 (1998); Toder et al., *Infect. Immun.* 62:1320-1327 (1994); Gambello et al., *Infect. Immun.* 61:1320-1327 (1993)). This indicates the two systems are arranged in a hierarchy where the las QS system is dominant over the rhl QS system. Since activation of the lasI gene by the AI1-LasR complex essentially triggers the initial steps in the cascade, LasR is considered the master regulator of *P. aeruginosa* QS.

More recently, a third signal molecule, 2-heptyl-3-hydroxy-4-quinolone (*Pseudomonas* quinolone signal, PQS), has been found to provide a possible additional link between the las and rhl QS networks (Pesci et al., *Proc. Natl Acad. Sci. USA* 96:11229-11234 (1999); McKnight et al., *J. Bacteriol.* 182:2702-2708 (2000)). These studies showed that PQS strongly induces rhlI while it has lesser positive effects on the transcription of lasR and rhlR. Still, the mechanism by which PQS influences the las and rhl QS networks and the proteins involved in PQS biosynthesis are unknown.

The QS system has been shown to directly relate to bacterial pathogenicity. In particular, a number of reports have shown a positive correlation between QS and *P. aeruginosa* virulence (Costerton et al., *Science* 284:1318-1322 (1999); de Kievit et al., *Sci. Med.* November/December:42-50 (1999); Passador et al., *Science* 260:1127-1130 (1993); de Kievit et al., *Infect. Immun.* 68:4839-5862 (2000); Storey et al., *Infect. Immun.* 66:2521-2528 (1998); Hassett et al., *Mol. Microbiol.*

34:1082-1093 (1999); Pearson et al., *Infect. Immun.* 68:4331-4334 (2000); Singh et al., *Nature* 407:762-764 (2000); Rumbaugh et al., *Infect. Immun.* 67:5854-5862 (1999); Tang et al., *Infect. Immun.* 64:37-43 (1996); Davies et al., *Science* 280:295-298 (1998); Tan et al., *Proc. Natl Acad. Sci. USA* 96:715-720 (1998); Tan et al., *Proc. Natl Acad. Sci. USA* 96:2408-2413 (1999); Sawa et al., *Infect. Immun.* 66:3242-3249 (1998); Telford et al., *Infect. Immun.* 66:36-42 (1998); Saleh et al., *Infect. Immun.* 67:5076-5082 (1999); Wu et al., *Microbiol.* 147:1105-1113 (2001); Silo-Suh et al., *Proc. Natl Acad. Sci. USA* 99:15699-15704 (2002); Lesprit et al., *American Journal of Respiratory and Critical Care Medicine* epub (2003)), for review see (Rumbaugh et al., *Microbes and Infection* 2:1721-1731 (2000)). Disruption of QS genes leads to decreased virulence in mouse, plant, nematode, *Drosophila*, and wax moth pathogenicity studies. For example, Hamood et al. have shown that the in vivo virulence of lasI, lasR, and rhlI mutants in a burned-mouse model (a commonly used mammalian pathogenicity model) was significantly reduced compared to the wild-type strain with an intact QS cascade (Rumbaugh et al., *Infect. Immun.* 67:5854-5862 (1999)). While the wild-type strain killed 94% of infected mice, the lasR mutant was able to kill only 28%, and the lasIrhlI double mutant killed only 7%. Expression in trans of constitutively active lasI and rhlI genes in the lasIrhlI mutant restored the ability of the organism to (i) spread within the burned tissue and systemically, and (ii) cause death at near wild-type levels (93%). Ausubel et al. have utilized a *C. elegans-P. aeruginosa* pathogenesis system to identify virulence-associated genes, and demonstrated that a lasR mutant is significantly less virulent in this surrogate model system (Tan et al., *Proc. Natl Acad. Sci. USA* 96:715-720 (1998); Tan et al., *Proc. Natl Acad. Sci. USA* 96:2408-2413 (1999); Mahajan-Miklos et al., *Cell* 96:47-56 (2003)). Interestingly, the QS mutants behave similarly to mutants with gene disruptions in crucial virulence factor genes. This is the expected result if indeed QS controls expression of virulence factors required for the disease process. It is interesting to note that interference with PQS production led to decreased expression of the LasB elastase virulence factor, further evidence that disruption of the QS system leads to decreased virulence (Calfee et al., *Proc. Natl Acad. Sci. USA* 98:11633-11637 (2001)).

Another critical discovery was the overlapping role of virulence factors that spanned different phyla (Rahme et al., *Science* 268:1899-1902 (1995); Tan et al., *Proc. Natl Acad. Sci. USA* 96:2408-2413 (1999); Mahajan-Miklos et al., *Cell* 96:47-56 (2003); Rahme et al., *Proc. Natl Acad. Sci. USA* 94:13245-13250 (1997); Plotnikova et al., *Plant Physiol.* 124:1766-1774 (2000)). The same *P. aeruginosa* mutants with reduced virulence in the worm, *C. elegans*, were also less virulent in the plant and burned mouse models. Based upon such experiments, it was postulated that the bacteria use the same virulence factors for infection of all hosts, a mode dependent upon QS.

A likely explanation for the decrease in virulence when QS is disrupted is that the QS transcriptional activators, LasR and RhlR, directly activate expression of genes encoding critical enzymes (LasB elastase, LasA protease, exoenzyme S, alkaline protease, and phospholipase C) and toxins (rhamnolipid, exotoxin A, cyanide, and pyocyanin) that contribute to the disease process (Rumbaugh et al., *Microbes and Infection* 2:1721-1731 (2000); de Kievit et al., *Sci. Med.* November/December:42-50 (1999); Whiteley et al., *Proc. Natl Acad. Sci. USA* 96:13904-13909 (1999)). QS also regulates components of the MexAB-OprM multidrug efflux pump (Evans et al., *J. Bacteriol.* 180:5443-5447 (1998)) and genes involved in resistance to reactive oxygen intermediates (sodA, sodB, and katA) (Hassett et al., *Mol. Microbiol.* 34:1082-1093 (1999)). Interestingly, the ability of *P. aeruginosa* to form complex, highly developed biofilms is also controlled by QS. Strains unable to form biofilms are less infectious. Davies et al. showed that a lasI mutant produces abnormal (thin and much more uniform) biofilms that are not resistant to detergent treatment. However, in the presence of exogenous AI1, this mutant forms normal detergent-resistant biofilms of an average thickness and cell density similar to that of the wild-type biofilms (Davies et al., *Science* 280:295-298 (1998)). Singh et al. recently demonstrated that *P. aeruginosa* in sputum of CF patients are living in the biofilm mode of growth. A direct correlation was made that revealed in vitro bio films and CF sputum harbored 3 times the AI2 relative to AI1 levels (Singh et al., *Nature* 407:762-764 (2000)), implicating the rhl system in playing a critical role in the biofilm mode of growth. Wu et al. confirmed these results, showing that acyl-HSL molecules are not only expressed by *P. aeruginosa* infecting mouse lung tissue, but their presence in the lung coincides with the occurrence of pathological changes (Wu et al., *Microbiol.* 146:2481-2493 (2000)). This strongly suggests that biofilms contribute to the chronic and refractory nature of *P. aeruginosa* infections in CF lungs, and biofilm formation is dependent on QS. Of particular importance is a study of sputa from lungs of CF patients by Storey et al. which found a direct correlation between the level of lasR mRNA and the level of LasB elastase, LasA protease, exotoxin A, and possibly algD (a gene involved in alginate synthesis, a major component of the biofilm matrix) mRNA (Storey et al., *Infect. Immun.* 66:2521-2528 (1998)). These studies provide the first direct evidence that QS is indeed active in human lung infections. However, drugs designed to fight *P. aeruginosa* and QS pathogens based on the QS pathway have not been identified.

In the last few years, investigations of synthetic autoinducer analogs, with respect to agonist and antagonist activities in the QS systems of *P. aeruginosa* (Passador et al., *J. Bacteriol.* 178:5995-6000 (1996); Kline et al., *Bioorg. Med. Chem. Lett.* 9:3447-3452 (1999)), *V. fischeri* (Schaefer et al., *J. Bacteriol.* 178:2897-2901 (1996)), and *A. tumefaciens* (Zhu et al., *J. Bacteriol.* 180:5398-5405 (1998)), have been reported. In these studies, major efforts were made to vary the length of the aliphatic side chain or modify the 3-oxo functionality of the autoinducers (substituting the 3-oxo group with 3-hydroxyl or methylene groups). The analog molecules whose structures are closely related to the cognate autoinducer structure exhibited weak-to-moderate gene activation (agonist activity). In some cases, the analogs weakly inhibited the induction of target genes (antagonist activity). These studies, however, failed to identify potent synthetic antagonists.

Interestingly, secondary metabolites isolated from the Australian macroalga, *Delisea pulchra*, exhibited moderate antagonist activity against QS-controlled gene expression in *Serratia liquefaciens, V. fischeri*, and *Erwinia carotovora*, all gram-negative bacteria with QS systems similar to that of *P. aeruginosa* (Givskov et al., *J. Bacteriol.* 178:6618-6622 (1996); Manefield et al., *Microbiol.* 145:283-291 (1999); Rasmussen et al., *Microbiol.* 146:3237-3244 (2000); Manefield et al., *FEMS Microbiol. Lett.* 205:131-138 (2001)). These natural products are highly halogenated furanone derivatives that are able to act as an antagonist of an AI2-like autoinducer in *S. liquefaciens* and 3-oxo-$C_6$-HSL in both *V. fischeri* and *E. carotovora*. Although their structure, in terms of the electronic and steric features, significantly differs from that of the HSL autoinducers, it still shares the features of the aliphatic side chain and the five-membered lactone ring (but fully conjugated) with the HSL autoinducers. The above naturally occurring furanone was nearly inactive in wild type of *P.*

*aeruginosa*, PAO1. In 2002, Hentzer et al. reported that a furanone that lacks the alkyl side chain of the natural product exhibits antagonist activity using a PAO-JP2 mini-Tn5-PlasB-gfp(ASV) reporter system (Hentzer et al., *Microbiol.* 148:87-102 (2002)). Approximately 50% inhibition was observed in the presence of 320 µM of the furanone competing with 0.1 µM AI1. It should be noted that Whiteley et al. grouped QS promoters into four classes based on their responsiveness to AI1 vs. AI2, and the degree and timing of that response (Whiteley et al., *Proc. Natl Acad. Sci. USA* 96:13904-13909 (1999)). The lasB promoter used in the Hentzer's study is a Class IV promoter that requires both AI1 and AI2 for full induction, and responds very little to AI1 alone. Additionally, they used a low AI1 concentration.

The present invention is directed to overcoming these and other deficiencies in the art.

SUMMARY OF THE INVENTION

The present invention relates to combinatorial libraries of autoinducer analogs as described below. The combinatorial libraries include solid phase (i.e., members of the library are attached to a solid support) and solution phase (i.e., members of the library are present in solution) libraries.

Another aspect of the present invention relates to an autoinducer agonist or antagonist having the structure

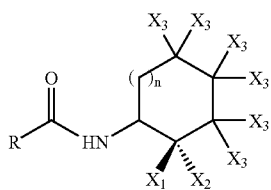

wherein $X_1$ is selected from the group consisting of H and OH, $X_2$ is selected from the group consisting of H and OH, $X_3$ is independently selected from the group consisting of H, OH, SH, $OR^1$, $SR^1$, $NH_2$, $NHR^1$, $NR^1R^2$, $COOR^1$, alkyl, cycloalkyl, alkenyl, alkynyl, aryl, heteroaryl, heteroalicyclic, acyl group, carbonyl, cyano, nitro, halogen, and, adjacent $X_3$ substituents combined, a cycloalkyl of 3 to 8 carbon atoms, a heterocycloalkyl of 3 to 8 members comprising carbon atoms and from 1 to 6 heteroatoms selected from the group consisting of N, S, and O, and an aryl or heteroaryl ring having 3 to 8 members, wherein $R^1$ and $R^2$ are selected from the group consisting of H, alkyl, cycloalkyl, alkenyl, aryl, heteroaryl, carbonyl, and sulfonyl and n is 0 to 4; or

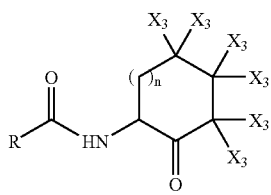

wherein $X_3$ is independently selected from the group consisting of H, OH, SH, $OR^1$, $SR^1$, $NH_2$, $NHR^1$, $NR^1R^2$, $COOR^1$, alkyl, cycloalkyl, alkenyl, alkynyl, aryl, heteroaryl, heteroalicyclic, acyl group, carbonyl, cyano, nitro, halogen, and, adjacent $X_3$ substituents combined, a cycloalkyl of 3 to 8 carbon atoms, a heterocycloalkyl of 3 to 8 members comprising carbon atoms and from 1 to 6 heteroatoms selected from the group consisting of N, S, and O, and an aryl or heteroaryl ring having 3 to 8 members, wherein $R^1$ and $R^2$ are selected from the group consisting of H, alkyl, cycloalkyl, alkenyl, aryl, heteroaryl, carbonyl, and sulfonyl and n is 0 to 4; or

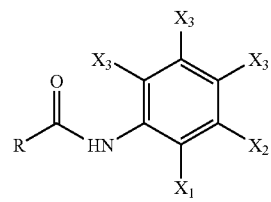

wherein $X_1$, $X_2$, and $X_3$ are independently selected from the group consisting of H, OH, SH, $OR^1$, $SR^1$, $NH_2$, $NHR^1$, $NR^1R^2$, $COOR^1$, alkyl, cycloalkyl, alkenyl, alkynyl, aryl, heteroaryl, heteroalicyclic, acyl group, carbonyl, cyano, nitro, halogen, and, adjacent $X_1$, $X_2$, and $X_3$ substituents combined, a cycloalkyl of 3 to 8 carbon atoms, a heterocycloalkyl of 3 to 8 members comprising carbon atoms and from 1 to 6 heteroatoms selected from the group consisting of N, S, and O, and an aryl or heteroaryl ring having 3 to 8 members, wherein $R^1$ and $R^2$ are selected from the group consisting of H, alkyl, cycloalkyl, alkenyl, aryl, heteroaryl, carbonyl, and sulfonyl; or

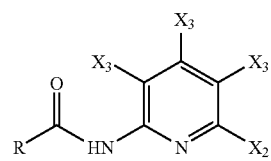

wherein $X_2$ and $X_3$ are independently selected from the group consisting of H, OH, SH, $OR^1$, $SR^1$, $NH_2$, $NHR^1$, $NR^1R^2$, $COOR^1$, alkyl, cycloalkyl, alkenyl, alkynyl, aryl, heteroaryl, heteroalicyclic, acyl group, carbonyl, cyano, nitro, halogen, and, adjacent $X_2$ and $X_3$ substituents combined, a cycloalkyl of 3 to 8 carbon atoms, a heterocycloalkyl of 3 to 8 members comprising carbon atoms and from 1 to 6 heteroatoms selected from the group consisting of N, S, and O, and an aryl or heteroaryl ring having 3 to 8 members, wherein $R^1$ and $R^2$ are selected from the group consisting of H, alkyl, cycloalkyl, alkenyl, aryl, heteroaryl, carbonyl, and sulfonyl, and wherein R is selected from the group consisting of $C_mH_{2m+1}$, wherein m is 1 to 14,

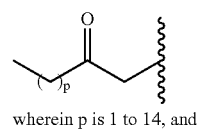

wherein p is 1 to 14, and

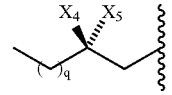

wherein q is 1 to 14, $X_4$ is OH, $NH_2$, or SH and $X_5$ is H, or $X_4$ is H and $X_5$ is OH, $NH_2$, or SH.

Compositions including the autoinducer analog(s) of the present invention are also disclosed and may also include an antibiotic.

Yet another aspect of the present invention relates to a method of identifying an autoinducer agonist. This method involves providing an autoinducer analog having the structure

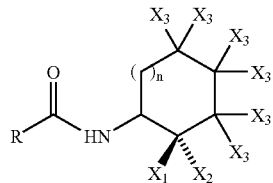

wherein $X_1$ is selected from the group consisting of H and OH, $X_2$ is selected from the group consisting of H and OH, $X_3$ is independently selected from the group consisting of H, OH, SH, $OR^1$, $SR^1$, $NH_2$, $NHR^1$, $NR^1R^2$, $COOR^1$, alkyl, cycloalkyl, alkenyl, alkynyl, aryl, heteroaryl, heteroalicyclic, acyl group, carbonyl, cyano, nitro, halogen, and, adjacent $X_3$ substituents combined, a cycloalkyl of 3 to 8 carbon atoms, a heterocycloalkyl of 3 to 8 members comprising carbon atoms and from 1 to 6 heteroatoms selected from the group consisting of N, S, and O, and an aryl or heteroaryl ring having 3 to 8 members, wherein $R^1$ and $R^2$ are selected from the group consisting of H, alkyl, cycloalkyl, alkenyl, aryl, heteroaryl, carbonyl, and sulfonyl, and n is 0 to 4; or

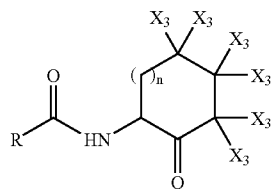

wherein $X_3$ is independently selected from the group consisting of H, OH, SH, $OR^1$, $SR^1$, $NH_2$, $NHR^1$, $NR^1R^2$, $COOR^1$, alkyl, cycloalkyl, alkenyl, alkynyl, aryl, heteroaryl, heteroalicyclic, acyl group, carbonyl, cyano, nitro, halogen, and, adjacent $X_3$ substituents combined, a cycloalkyl of 3 to 8 carbon atoms, a heterocycloalkyl of 3 to 8 members comprising carbon atoms and from 1 to 6 heteroatoms selected from the group consisting of N, S, and O, and an aryl or heteroaryl ring having 3 to 8 members, wherein $R^1$ and $R^2$ are selected from the group consisting of H, alkyl, cycloalkyl, alkenyl, aryl, heteroaryl, carbonyl, and sulfonyl, and n is 0 to 4; or

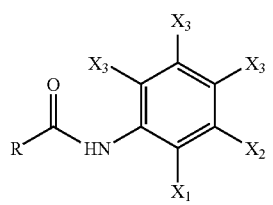

wherein $X_1$, $X_2$, and $X_3$ are independently selected from the group consisting of H, OH, SH, $OR^1$, $SR^1$, $NH_2$, $NHR^1$, $NR^1R^2$, $COOR^1$, alkyl, cycloalkyl, alkenyl, alkynyl, aryl, heteroaryl, heteroalicyclic, acyl group, carbonyl, cyano, nitro, halogen, and, adjacent $X_1$, $X_2$, and $X_3$ substituents combined, a cycloalkyl of 3 to 8 carbon atoms, a heterocycloalkyl of 3 to 8 members comprising carbon atoms and from 1 to 6 heteroatoms selected from the group consisting of N, S, and O, and an aryl or heteroaryl ring having 3 to 8 members, wherein $R^1$ and $R^2$ are selected from the group consisting of H, alkyl, cycloalkyl, alkenyl, aryl, heteroaryl, carbonyl, and sulfonyl; or

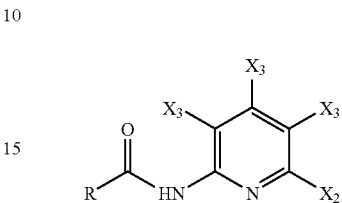

wherein $X_2$ and $X_3$ are independently selected from the group consisting of H, OH, SH, $OR^1$, $SR^1$, $NH_2$, $NHR^1$, $NR^1R^2$, $COOR^1$, alkyl, cycloalkyl, alkenyl, alkynyl, aryl, heteroaryl, heteroalicyclic, acyl group, carbonyl, cyano, nitro, halogen, and, adjacent $X_2$ and $X_3$ substituents combined, a cycloalkyl of 3 to 8 carbon atoms, a heterocycloalkyl of 3 to 8 members comprising carbon atoms and from 1 to 6 heteroatoms selected from the group consisting of N, S, and O, and an aryl or heteroaryl ring having 3 to 8 members, wherein $R^1$ and $R^2$ are selected from the group consisting of H, alkyl, cycloalkyl, alkenyl, aryl, heteroaryl, carbonyl, and sulfonyl, and wherein R is selected from the group consisting of $C_mH_{2m+1}$, wherein m is 1 to 14,

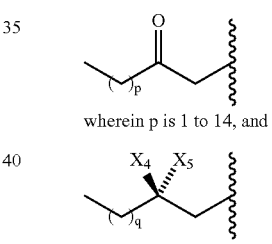

wherein p is 1 to 14, and

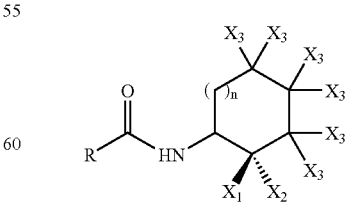

wherein q is 1 to 14, $X_4$ is OH, $NH_2$, or SH and $X_5$ is H, or $X_4$ is H and $X_5$ is OH, $NH_2$, or SH. The autoinducer analog is contacted with an autoinducer receptor and activity of the receptor is measured in the presence of the autoinducer analog.

A further aspect of the present invention relates to a method of identifying an autoinducer antagonist. This method involves providing an autoinducer analog having the structure

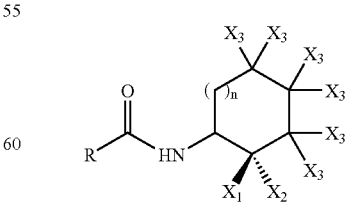

wherein $X_1$ is selected from the group consisting of H and OH, $X_2$ is selected from the group consisting of H and OH, $X_3$ is independently selected from the group consisting of H, OH, SH, OR$^1$, SR$^1$, NH$_2$, NHR$^1$, NR$^1$R$^2$, COOR$^1$, alkyl, cycloalkyl, alkenyl, alkynyl, aryl, heteroaryl, heteroalicyclic, acyl group, carbonyl, cyano, nitro, halogen, and, adjacent X$_3$ substituents combined, a cycloalkyl of 3 to 8 carbon atoms, a heterocycloalkyl of 3 to 8 members comprising carbon atoms and from 1 to 6 heteroatoms selected from the group consisting of N, S, and O, and an aryl or heteroaryl ring having 3 to 8 members, wherein R$^1$ and R$^2$ are selected from the group consisting of H, alkyl, cycloalkyl, alkenyl, aryl, heteroaryl, carbonyl, and sulfonyl, and n is 0 to 4; or

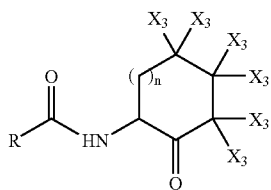

wherein X$_3$ is independently selected from the group consisting of H, OH, SH, OR$^1$, SR$^1$, NH$_2$, NHR$^1$, NR$^1$R$^2$, COOR$^1$, alkyl, cycloalkyl, alkenyl, alkynyl, aryl, heteroaryl, heteroalicyclic, acyl group, carbonyl, cyano, nitro, halogen, and, adjacent X$_3$ substituents combined, a cycloalkyl of 3 to 8 carbon atoms, a heterocycloalkyl of 3 to 8 members comprising carbon atoms and from 1 to 6 heteroatoms selected from the group consisting of N, S, and O, and an aryl or heteroaryl ring having 3 to 8 members, wherein R$^1$ and R$^2$ are selected from the group consisting of H, alkyl, cycloalkyl, alkenyl, aryl, heteroaryl, carbonyl, and sulfonyl, and n is 0 to 4; or

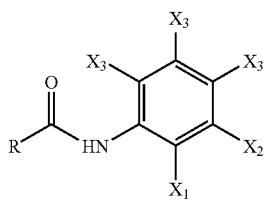

wherein X$_1$, X$_2$, and X$_3$ are independently selected from the group consisting of H, OH, SH, OR$^1$, SR$^1$, NH$_2$, NHR$^1$, NR$^1$R$^2$, COOR$^1$, alkyl, cycloalkyl, alkenyl, alkynyl, aryl, heteroaryl, heteroalicyclic, acyl group, carbonyl, cyano, nitro, halogen, and, adjacent X$_1$, X$_2$, and X$_3$ substituents combined, a cycloalkyl of 3 to 8 carbon atoms, a heterocycloalkyl of 3 to 8 members comprising carbon atoms and from 1 to 6 heteroatoms selected from the group consisting of N, S, and O, and an aryl or heteroaryl ring having 3 to 8 members, wherein R$^1$ and R$^2$ are selected from the group consisting of H, alkyl, cycloalkyl, alkenyl, aryl, heteroaryl, carbonyl, and sulfonyl; or

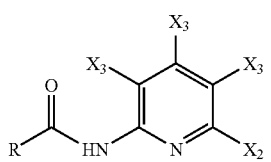

wherein X$_2$ and X$_3$ are independently selected from the group consisting of H, OH, SH, OR$^1$, SR$^1$, NH$_2$, NHR$^1$, NR$^1$R$^2$, COOR$^1$, alkyl, cycloalkyl, alkenyl, alkynyl, aryl, heteroaryl, heteroalicyclic, acyl group, carbonyl, cyano, nitro, halogen, and, adjacent X$_2$ and X$_3$ substituents combined, a cycloalkyl of 3 to 8 carbon atoms, a heterocycloalkyl of 3 to 8 members comprising carbon atoms and from 1 to 6 heteroatoms selected from the group consisting of N, S, and O, and an aryl or heteroaryl ring having 3 to 8 members, wherein R$^1$ and R$^2$ are selected from the group consisting of H, alkyl, cycloalkyl, alkenyl, aryl, heteroaryl, carbonyl, and sulfonyl, and wherein R is selected from the group consisting of $C_mH_{2m+1}$, wherein m is 1 to 14,

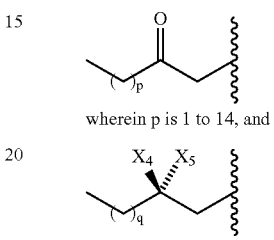

wherein p is 1 to 14, and

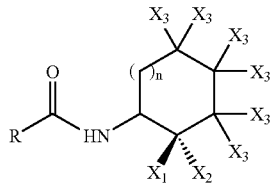

wherein q is 1 to 14, X$_4$ is OH, NH$_2$, or SH and X$_5$ is H, or X$_4$ is H and X$_5$ is OH, NH$_2$, or SH. The autoinducer analog is contacted with an autoinducer receptor and an autoinducer, whereby competition between the autoinducer analog and the autoinducer for the autoinducer receptor is allowed to occur. Activity of the receptor in the presence of the autoinducer analog and autoinducer is then measured and compared with activity of the receptor in the presence of only the autoinducer.

Yet another aspect of the present invention relates to a method for regulating the activity of an autoinducer receptor. This method involves contacting an autoinducer receptor with an autoinducer analog, wherein the autoinducer analog is an autoinducer agonist or antagonist. In one embodiment, the autoinducer analog has the structure wherein X$_1$ is selected from the group consisting of H and OH, X$_2$ is selected from the group consisting of H and OH, X$_3$ is independently selected from the group consisting of H, OH, SH, OR$^1$, SR$^1$, NH$_2$, NHR$^1$, NR$^1$R$^2$, COOR$^1$, alkyl, cycloalkyl, alkenyl, alkynyl, aryl, heteroaryl, heteroalicyclic, acyl group, carbonyl, cyano, nitro, halogen, and, adjacent X$_3$ substituents combined, a cycloalkyl of 3 to 8 carbon atoms, a heterocycloalkyl of 3 to 8 members comprising carbon atoms and from 1 to 6 heteroatoms selected from the group consisting of N, S, and O, and an aryl or heteroaryl ring having 3 to 8 members, wherein R$^1$ and R$^2$ are selected from the group consisting of H, alkyl, cycloalkyl, alkenyl, aryl, heteroaryl, carbonyl, and sulfonyl, and n is 0 to 4; or

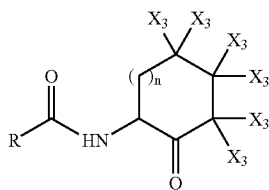

wherein $X_3$ is independently selected from the group consisting of H, OH, SH, $OR^1$, $SR^1$, $NH_2$, $NHR^1$, $NR^1R^2$, $COOR^1$, alkyl, cycloalkyl, alkenyl, alkynyl, aryl, heteroaryl, heteroalicyclic, acyl group, carbonyl, cyano, nitro, halogen, and, adjacent $X_3$ substituents combined, a cycloalkyl of 3 to 8 carbon atoms, a heterocycloalkyl of 3 to 8 members comprising carbon atoms and from 1 to 6 heteroatoms selected from the group consisting of N, S, and O, and an aryl or heteroaryl ring having 3 to 8 members, wherein $R^1$ and $R^2$ are selected from the group consisting of H, alkyl, cycloalkyl, alkenyl, aryl, heteroaryl, carbonyl, and sulfonyl, and n is 0 to 4; or

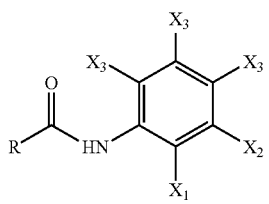

wherein $X_1$, $X_2$, and $X_3$ are independently selected from the group consisting of H, OH, SH, $OR^1$, $SR_1$, $NH_2$, $NHR^1$, $NR^1R^2$, $COOR^1$, alkyl, cycloalkyl, alkenyl, alkynyl, aryl, heteroaryl, heteroalicyclic, acyl group, carbonyl, cyano, nitro, halogen, and, adjacent $X_1$, $X_2$, and $X_3$ substituents combined, a cycloalkyl of 3 to 8 carbon atoms, a heterocycloalkyl of 3 to 8 members comprising carbon atoms and from 1 to 6 heteroatoms selected from the group consisting of N, S, and O, and an aryl or heteroaryl ring having 3 to 8 members, wherein $R^1$ and $R^2$ are selected from the group consisting of H, alkyl, cycloalkyl, alkenyl, aryl, heteroaryl, carbonyl, and sulfonyl; or

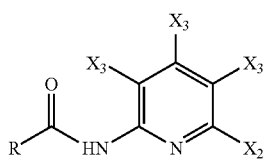

wherein $X_2$ and $X_3$ are independently selected from the group consisting of H, OH, SH, $OR^1$, $SR_1$, $NH_2$, $NHR^1$, $NR^1R^2$, $COOR^1$, alkyl, cycloalkyl, alkenyl, alkynyl, aryl, heteroaryl, heteroalicyclic, acyl group, carbonyl, cyano, nitro, halogen, and, adjacent $X_2$ and $X_3$ substituents combined, a cycloalkyl of 3 to 8 carbon atoms, a heterocycloalkyl of 3 to 8 members comprising carbon atoms and from 1 to 6 heteroatoms selected from the group consisting of N, S, and O, and an aryl or heteroaryl ring having 3 to 8 members, wherein $R^1$ and $R^2$ are selected from the group consisting of H, alkyl, cycloalkyl, alkenyl, aryl, heteroaryl, carbonyl, and sulfonyl, and wherein R is selected from the group consisting of $C_mH_{2m+1}$, wherein m is 1 to 14,

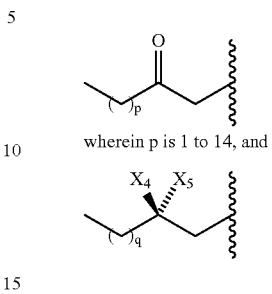

wherein p is 1 to 14, and wherein q is 1 to 14, $X_4$ is OH, $NH_2$, or SH and $X_5$ is H, or $X_4$ is H and $X_5$ is OH, $NH_2$, or SH, whereby activity of the autoinducer receptor is regulated.

A further aspect of the present invention relates to a method of regulating biofilm formation. This method involves contacting a cell of an organism with an autoinducer analog as described herein, whereby biofilm formation on the cell is regulated. In accordance with the present invention, biofilm formation may be inhibited or biofilm architecture may be modified by contact with the autoinducer analog.

The present invention also relates to a method for regulating the growth or virulence of an organism in a subject. This method involves contacting a cell of an organism with an autoinducer analog as described herein, whereby growth or virulence of the organism in the subject is regulated.

Another aspect of the present invention relates to a method of inhibiting a quorum sensing mechanism in an organism. This method involves contacting a cell of an organism possessing a quorum sensing mechanism with an autoinducer analog as described herein, whereby the quorum sensing mechanism of the organism is inhibited.

Yet another aspect of the present invention relates to a method of treating an infection in a subject caused by an organism possessing a quorum sensing mechanism. This method involves administering to the subject an effective amount of a composition including an autoinducer analog as described herein and a pharmaceutically acceptable carrier or diluent.

In accordance with the present invention, combinatorial libraries of autoinducer analogs can be prepared. Such libraries can be used to identify antagonists that will inhibit the interaction between wild type autoinducer molecules and their cognate transcription regulator proteins, both of which play critical roles in regulating the quorum sensing cascade. The antagonists can be used in new therapies to fight infection by *P. aeruginosa* as well as other organisms which use a quorum sensing system to regulate the production of numerous virulence factors and to form protective biofilms.

BRIEF DESCRIPTION OF THE DRAWINGS

FIG. 1A shows a schematic representation of QS activation from low cell density to high cell density, to biofilm development (left), and the mechanism of two QS circuits, las and rhl (right). Light grey lines and arrows indicate specific activations by the complex of R proteins to the cognate autoinducers (AIs). Dark grey arrows indicate secretion of AIs or virulence factors to initiate the cell-to-cell communication or host attacks. FIG. 1B shows the chemical structures of autoinducers found in *P. aeruginosa* QS circuits. AI1 activates the las circuit, while AI2 activates the rhl circuit.

FIG. 5A is a 96-well plate assay of PAO-JP2 (plasI-LVAgfp) in the presence of library compounds. Negative control is no treatment. Positive control is 1 μM AI1. Each well of the plate contains roughly 400 μM of one library compound. FIG. 5B shows the structures of compounds in wells with GFP expression and related compounds lacking agonist activity.

FIG. 9A shows PAO-JP2 (plasI-LVAgfp) expression of GFP in the presence of increasing amounts of designated compounds. FIG. 9B shows MG4 (pKDT37) beta-galactosidase activity in the presence of increasing amounts of designated compounds.

In FIG. 10B, PAO-JP2 (plasI-LVAgfp) was grown for 6 hours in the presence of 1 μM AI1 alone (white) or with 3-oxo-$C_{12}$-D10 competitor (dark grey). In FIG. 10C, PAO-JP2 (prhlI-LVAgfp) was grown for 6 hours in the presence of 1 μM AI1 and 10 μM AI2 alone (white) or with 3-oxo-$C_{12}$-D10 (dark grey) or $C_4$-D10 (grey). Fluorescence intensity was divided by $OD_{600}$ of cell culture. Control was set to 1 and all other values are relative.

In FIG. 11A, PAO-JP2 was grown for 6 hours in the absence (negative control, white) or presence (positive control, grey) of 5 μM AI1 and 10 μM AI2 or in combination with 3-oxo-$C_{12}$-D10 (dark grey), and elastase activity was determined. In FIG. 11B, wild type strain PAO1 was grown without (grey) or with antagonist (dark grey). In FIG. 11C, PAO-JP2 was grown for 18 hours in the absence (negative control, white) or presence (positive control, grey) of 25 μM AI1 and 25 μM AI2 or in combination with 3-oxo-$C_{12}$-D10 (dark grey) then assayed for pyocyanin production. In FIG. 11D, PAO1 was grown without (grey) or with antagonist (dark grey) then assayed for pyocyanin production.

FIGS. 12A-C show PAO-JP2 (pTdK-GFP) (de Kievit et al., *Appl. Environ. Microbiol.* 67:865-1873 (2001), which is hereby incorporated by reference in its entirety) biofilm development in the presence of designated compounds. FIGS. 12A and B represent negative and positive controls. FIGS. 12D and E show the absence (negative control) or presence of antagonist, respectively.

FIG. 14A shows a Molecular Imager scan of a 96-well plate containing PAO-JP2 (plasI-LVAgfp) in the presence of 1, 100, and 400 μM of the designated 3-oxo-$C_{12}$ compound. FIG. 14B shows the quantification of results of 3-oxo-$C_{13}$ compounds. Cont, negative control of untreated cell (not shown in FIG. 14A). Average fluorescence of four replicate wells was corrected for cell density by dividing by $OD_{600}$ of cell culture. The standard deviation was derived from three independent experiments shown in FIG. 14A. FIG. 14C shows a Molecular Imager scan of a 96-well plate containing PAO-JP2 (prhlI-LVAgfp) in the presence of 1 μM AI2 and 10, 100, and 400 μM designated $C_4$ compound. FIG. 14D shows the quantification of results of $C_4$ compounds. Data analysis was the same as in FIG. 14B.

FIG. 15A shows GFP expression by PAO-JP2 (plasI-LVAgfp) in the presence of 1 μM AI1 alone (control, black bar) or 1 μM AI1 plus 2 or 3. FIG. 15B shows GFP expression by PAO-JP2 (prhlI-LVAgfp) in the presence of 1 μM AI1 and 10 μM AI2 (control, black bar) or 1 μM AI1 and 10 μM AI2 plus 2 or 3.

FIG. 16A shows pyocyanin expression by PAO-JP2. −, negative control; +, positive control, 25 μM each of AI1 and AI2; 2, 25 μM each of AI1 and AI2 in the presence of 100 μM 2; 3, 25 μM each of AI1 and AI2 in the presence of 100 μM 3. FIG. 16B shows the quantification of pyocyanin expression by PAO-JP2 in the presence of various concentrations of 2 or 3. −, negative control containing no AIs; +, positive control containing 25 μM each of AI1 and AI2; 2, 25 μM each of AI1 and AI2 in the presence of 2; 3, 25 μM each of AI1 and AI2 in the presence of 3. FIG. 16C shows the quantification of pyocyanin expression of wild type strain PAO1. The conditions were the same as FIG. 16B, except for control where no AIs were added. FIG. 16D shows elastase B activity produced by PAO-JP2 in the absence (—control) or presence of 5 μM AI1 and 10 μM AI2 (+control) or 5 μM AI1 and 10 μM AI2 plus 2 or 3. FIG. 16E shows elastase B activity produced by PAO1 control or in the presence of 2 or 3.

FIG. 17A shows PAO-JP2 (pTdK-GFP) biofilm development in the presence of designated compounds. FIG. 17B shows PAO-1 (pTdK-GFP) biofilm development in the absence (negative control) or presence of 50 μM 3.

FIG. 20A shows solid phase synthesis of the library based on 3-aminocyclohexene. Reagents and Conditions: (a) (i) PPTS; (ii) mCPBA; (b) $X^-M^+$ or Lewis acid with TMS-X; (c) (i) TFA; (ii) Dess-Martin reagent.

In FIG. 21A, $X_1$, $X_2$, and $X_3$ can be any functional group. FIG. 21B shows aniline derivatives with expanded rings.

DETAILED DESCRIPTION OF THE INVENTION

Figure 1:
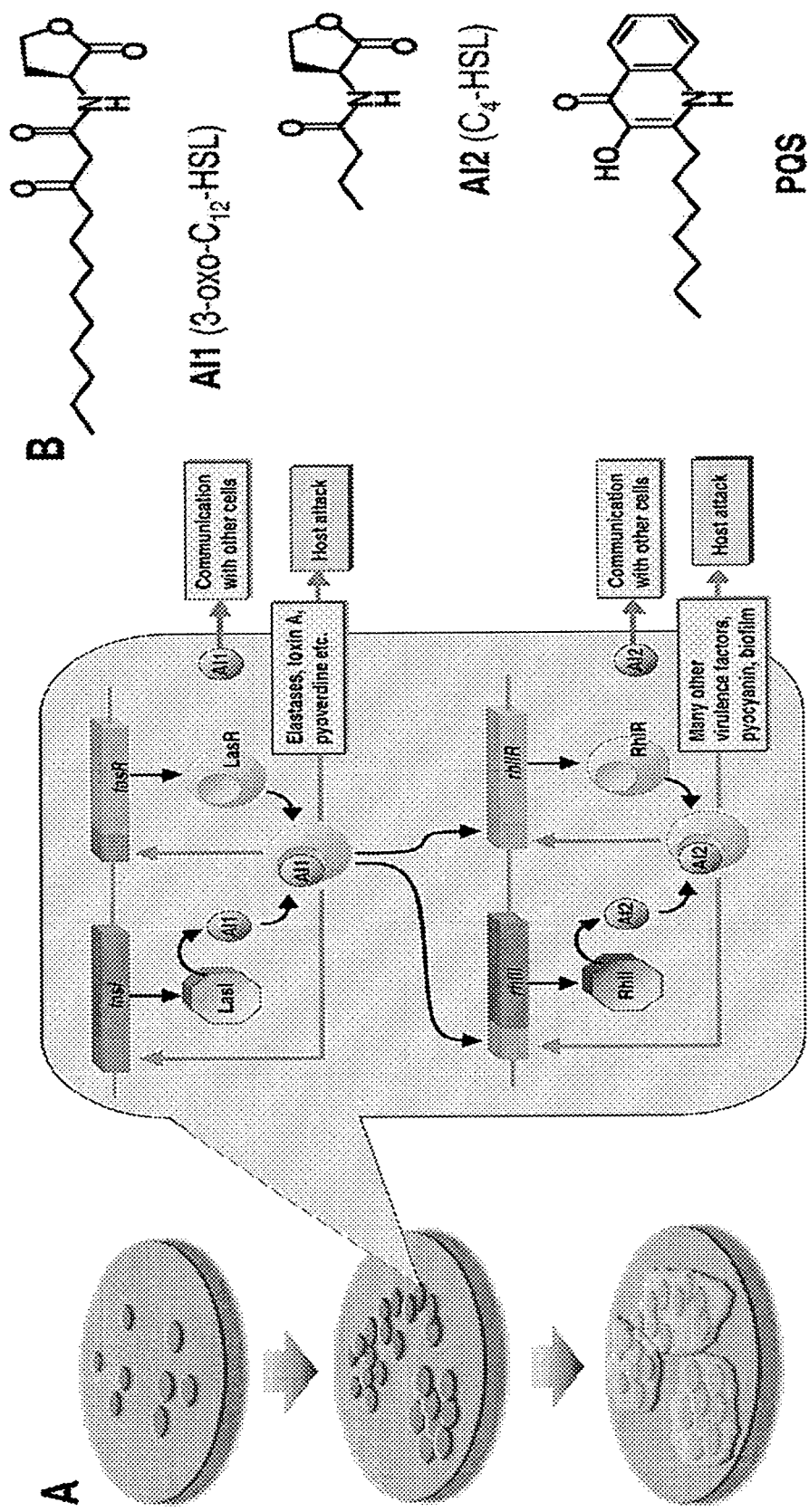
FIGS. 1A-B shows quorum sensing (QS) in *P. aeruginosa*.

The present invention relates to a combinatorial library of autoinducer analogs, including two or more different autoinducer analogs of the structure

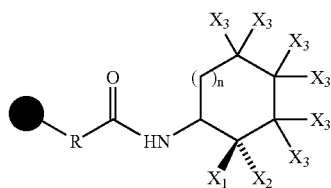

wherein $X_1$ is independently selected from the group consisting of H and OH, $X_2$ is independently selected from the group consisting of H and OH, $X_3$ is independently selected from the group consisting of H, OH, SH, $OR^1$, $SR^1$, $NH_2$, $NHR^1$, $NR^1R^2$, $COOR^1$, alkyl, cycloalkyl, alkenyl, alkynyl, aryl, heteroaryl, heteroalicyclic, acyl group, carbonyl, cyano, nitro, halogen, and, adjacent $X_3$ substituents combined, a cycloalkyl of 3 to 8 carbon atoms, a heterocycloalkyl of 3 to 8 members comprising carbon atoms and from 1 to 6 heteroatoms selected from the group consisting of N, S, and O, and an aryl or heteroaryl ring having 3 to 8 members, wherein $R^1$ and $R^2$ are selected from the group consisting of H, alkyl, cycloalkyl, alkenyl, aryl, heteroaryl, carbonyl, and sulfonyl, ● is a solid support, and n is 0 to 4; or

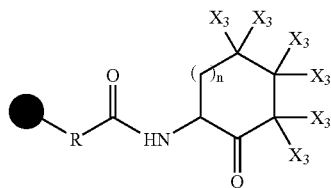

wherein $X_3$ is independently selected from the group consisting of H, OH, SH, $OR^1$, $SR^1$, $NH_2$, $NHR^1$, $NR^1R^2$, $COOR^1$, alkyl, cycloalkyl, alkenyl, alkynyl, aryl, heteroaryl, heteroalicyclic, acyl group, carbonyl, cyano, nitro, halogen, and, adjacent $X_3$ substituents combined, a cycloalkyl of 3 to 8 carbon atoms, a heterocycloalkyl of 3 to 8 members comprising carbon atoms and from 1 to 6 heteroatoms selected from the group consisting of N, S, and O, and an aryl or heteroaryl ring having 3 to 8 members, wherein $R^1$ and $R^2$ are selected from the group consisting of H, alkyl, cycloalkyl, alkenyl, aryl, heteroaryl, carbonyl, and sulfonyl, ● is a solid support, and n is 0 to 4; or

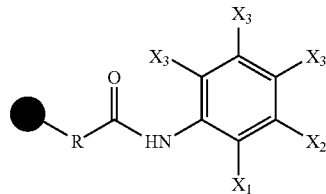

wherein $X_1$, $X_2$, and $X_3$ are independently selected from the group consisting of H, OH, SH, $OR^1$, $SR^1$, $NH_2$, $NHR^1$, $NR^1R^2$, $COOR^1$, alkyl, cycloalkyl, alkenyl, alkynyl, aryl, heteroaryl, heteroalicyclic, acyl group, carbonyl, cyano, nitro, halogen, and, adjacent $X_1$, $X_2$, and $X_3$ substituents combined, a cycloalkyl of 3 to 8 carbon atoms, a heterocycloalkyl of 3 to 8 members comprising carbon atoms and from 1 to 6 heteroatoms selected from the group consisting of N, S, and O, and an aryl or heteroaryl ring having 3 to 8 members, wherein $R^1$ and $R^2$ are selected from the group consisting of H, alkyl, cycloalkyl, alkenyl, aryl, heteroaryl, carbonyl, and sulfonyl, and ● is a solid support; or

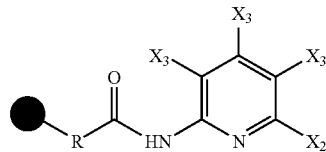

wherein $X_2$ and $X_3$ are independently selected from the group consisting of H, OH, SH, $OR^1$, $SR^1$, $NH_2$, $NHR^1$, $NR^1R^2$, $COOR^1$, alkyl, cycloalkyl, alkenyl, alkynyl, aryl, heteroaryl, heteroalicyclic, acyl group, carbonyl, cyano, nitro, halogen, and, adjacent $X_2$ and $X_3$ substituents combined, a cycloalkyl of 3 to 8 carbon atoms, a heterocycloalkyl of 3 to 8 members comprising carbon atoms and from 1 to 6 heteroatoms selected from the group consisting of N, S, and O, and an aryl or heteroaryl ring having 3 to 8 members, wherein $R^1$ and $R^2$ are selected from the group consisting of H, alkyl, cycloalkyl, alkenyl, aryl, heteroaryl, carbonyl, and sulfonyl, and is a solid support, and wherein R is selected from the group consisting of $C_mH_{2m}$, wherein m is 1 to 14,

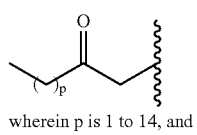

wherein p is 1 to 14, and

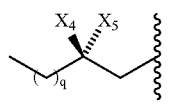

wherein q is 1 to 14, $X_4$ is OH, $NH_2$, or SH and $X_5$ is H, or $X_4$ is H and $X_5$ is OH, $NH_2$, or SH. The side chain ($C_mH_{2m}$, $C_{(p)}$, or $C_{(q)}$) in the R group may include saturated and unsaturated bonds and may be substituted or unsubstituted. Suitable substitutions are described below with respect to alkyl groups in general. In this embodiment of the present invention, the combinatorial library is a solid phase library.

As used herein, the term alkyl refers to a saturated aliphatic hydrocarbon include straight chain and branched chain groups. Preferably, the alkyl group has from 1 to 12 carbon atoms. The alkyl group may be substituted or unsubstituted. Suitable substituents include, but are not limited to, cycloalkyl, aryl, heteroaryl, heteroalicyclic, hydroxy, alkoxy, aryloxy, thiohydroxy, thioalkoxy, thioaryloxy, cyano, halogen, carbonyl, thiocarbonyl, carboxy, nitro, silyl, and amino. A cycloalkyl group refers to an all carbon monocyclic or fused ring (i.e., rings which share an adjacent pair of atoms) group wherein one or more of the rings does not have a completely conjugated pi-electron system. Suitable cycloalkyl groups include, but are not limited to, cyclopropane, cyclobutane, cyclopentane, cyclopentene, cyclohexane, cyclohexadiene, cycloheptane, and cycloheptatriene. A cycloalkyl group may be substituted or unsubstituted. Suitable substituents include those describe above an alkyl groups.

As used herein, an aryl group refers to an all carbon monocyclic or fused-ring polycyclic group having a completely conjugated pi-electron system. Suitable examples of aryl groups include, but are not limited to, phenyl, benzyl, benzoyl, naphthalenyl, and anthracenyl. The aryl group may be substituted or unsubstituted. Suitable substituents include, but are not limited to, alkyl, hydroxy, alkoxy, aryloxy, thiohydroxy, thioalkoxy, thioaryloxy, cyano, nitro, carbonyl, thiocarbonyl, carboxy, sulfinyl, sulfonyl, amino, halogen, and triohalomethyl.

As used herein, a heteroaryl group refers to a monocyclic or fused ring group having in the ring(s) one or more heteroatoms, such as sulfur, nitrogen, and oxygen, and in addition having a completely conjugated pi-electron system. Suitable heteroaryl groups include, but are not limited to, pyrrole, furan, thiophene, imidazole, oxazole, thiazole, pyrazole, pyridine, pyrimidine, quinoline, isoquinoline, purine, and carbazole. The heteroaryl group may be substituted or unsubstituted. Suitable substituents include, but are not limited to, alkyl, cycloalkyl, hydroxy, alkoxy, aryloxy, thiohydroxy, thioalkoxy, thioaryloxy, cyano, nitro, carbonyl, thiocarbonyl, carboxy, sulfinyl, sulfonyl, amino, halogen, and triohalomethyl.

As used herein, a heteroalicyclic group (or heterocycloalkyl) refers to a monocyclic or fused ring group having in the ring(s) one or more heteroatoms, such as sulfur, nitrogen, and oxygen. The rings may also have one or more double bonds. However, the rings do not have a completely conjugated pi-electron system. The heteroalicyclic ring may be substituted or unsubstituted. Suitable substituents include, but are not limited to, alkyl, cycloalkyl, hydroxy, alkoxy, aryloxy, thiohydroxy, thioalkoxy, thioaryloxy, cyano, nitro, carbonyl, thiocarbonyl, carboxy, sulfinyl, sulfonyl, amino, halogen, and triohalomethyl.

A second embodiment of the present invention relates to a combinatorial library including two or more different autoinducer analogs of the structure

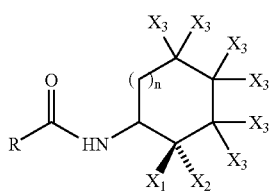

wherein $X_1$ is independently selected from the group consisting of H and OH, $X_2$ is independently selected from the group consisting of H and OH, $X_3$ is independently selected from the group consisting of H, OH, SH, $OR^1$, $SR^1$, $NH_2$, $NHR^1$, $NR^1R^2$, $COOR^1$, alkyl, cycloalkyl, alkenyl, alkynyl, aryl, heteroaryl, heteroalicyclic, acyl group, carbonyl, cyano, nitro, halogen, and, adjacent $X_3$ substituents combined, a cycloalkyl of 3 to 8 carbon atoms, a heterocycloalkyl of 3 to 8 members comprising carbon atoms and from 1 to 6 heteroatoms selected from the group consisting of N, S, and O, and an aryl or heteroaryl ring having 3 to 8 members, wherein $R^1$ and $R^2$ are selected from the group consisting of H, alkyl, cycloalkyl, alkenyl, aryl, heteroaryl, carbonyl, and sulfonyl, n is 0 to 4; or

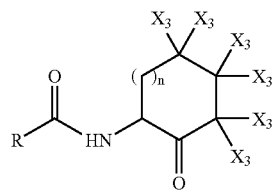

wherein $X_3$ is independently selected from the group consisting of H, OH, SH, $OR^1$, $SR^1$, $NH_2$, $NHR^1$, $NR^1R^2$, $COOR^1$, alkyl, cycloalkyl, alkenyl, alkynyl, aryl, heteroaryl, heteroalicyclic, acyl group, carbonyl, cyano, nitro, halogen, and, adjacent $X_3$ substituents combined, a cycloalkyl of 3 to 8 carbon atoms, a heterocycloalkyl of 3 to 8 members comprising carbon atoms and from 1 to 6 heteroatoms selected from the group consisting of N, S, and O, and an aryl or heteroaryl ring having 3 to 8 members, wherein $R^1$ and $R^2$ are selected from the group consisting of H, alkyl, cycloalkyl, alkenyl, aryl, heteroaryl, carbonyl, and sulfonyl, n is 0 to 4; or

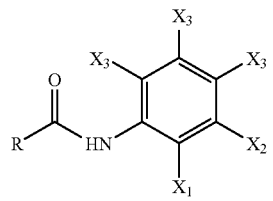

wherein $X_1$, $X_2$, and $X_3$ are independently selected from the group consisting of H, OH, SH, $OR^1$, $SR^1$, $NH_2$, $NHR^1$, $NR^1R^2$, $COOR^1$, alkyl cycloalkyl, alkenyl, alkynyl, aryl, heteroaryl, heteroalicyclic, acyl group, carbonyl, cyano, nitro, halogen, and, adjacent $X_1$, $X_2$, and $X_3$ substituents combined, a cycloalkyl of 3 to 8 carbon atoms, a heterocycloalkyl of 3 to 8 members comprising carbon atoms and from 1 to 6 heteroatoms selected from the group consisting of N, S, and O, and an aryl or heteroaryl ring having 3 to 8 members, wherein $R^1$ and $R^2$ are selected from the group consisting of H, alkyl, cycloalkyl, alkenyl, aryl, heteroaryl, carbonyl, and sulfonyl; or

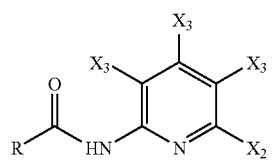

wherein $X_2$ and $X_3$ are independently selected from the group consisting of H, OH, SH, $OR^1$, $SR^1$, $NH_2$, $NHR^1$, $NR^1R^2$, $COOR^1$, alkyl, cycloalkyl, alkenyl, alkynyl, aryl, heteroaryl, heteroalicyclic, acyl group, carbonyl, cyano, nitro, halogen, and, adjacent $X_2$ and $X_3$ substituents combined, a cycloalkyl of 3 to 8 carbon atoms, a heterocycloalkyl of 3 to 8 members comprising carbon atoms and from 1 to 6 heteroatoms selected from the group consisting of N, S, and O, and an aryl or heteroaryl ring having 3 to 8 members, wherein $R^1$ and $R^2$ are selected from the group consisting of H, alkyl, cycloalkyl, alkenyl, aryl, heteroaryl, carbonyl, and sulfonyl, and wherein R is selected from the group consisting of $C_mH_{2m+1}$, wherein m is 1 to 14,

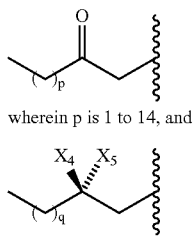

wherein p is 1 to 14, and wherein q is 1 to 14, $X_4$ is OH, $NH_2$, or SH and $X_5$ is H, or $X_4$ is H and $X_5$ is OH, $NH_2$, or SH. Thus, in this embodiment of the present invention, the combinatorial library is a solution phase library.

As used herein an autoinducer is a molecule encoded by an autoinducer synthase gene (e.g., I gene) in a quorum sensing pathway of an organism. FIGS. 1A-B show the quorum sensing pathway in *P. aeruginosa* and the generation of two autoinducer molecules, AI1 and AI2, by the I genes LasI and RhlI. As used herein, a "combinatorial library" is an intentionally created collection of differing molecules which can be created by the techniques set forth below or otherwise and screened for activity in a variety of formats (e.g., libraries of soluble molecules or libraries of compounds attached to a solid support). A "combinatorial library" involves successive and/or parallel rounds of chemical synthesis based on a common starting structure. The combinatorial libraries can be screened in a variety of assays, such as those described below as well as other assays useful for assessing biological or chemical activities. The combinatorial libraries will generally have at least one active compound and are generally prepared such that the compounds are in equimolar quantities. Thus, in one embodiment of the present invention, the combinatorial library includes at least one compound which is active as an autoinducer agonist or an autoinducer antagonist. Compounds disclosed in the prior art that are not in an intentionally created collection are not part of a "combinatorial library" of the present invention. In addition, compounds that are part of an unintentional or undesired mixture are not part of a "combinatorial library" of the present invention.

A combinatorial library in accordance with the present invention can include any number of different autoinducer analogs. As used herein an autoinducer analog is different if one autoinducer analog includes an R group, an $X_1$ group, an $X_2$ group, or an $X_3$ group which is not present in the other autoinducer analog or an n value which is different than the other autoinducer analog. In one embodiment, the combinatorial library contains at least about 1,000 to 10,000 different autoinducer analogs.

The combinatorial library of autoinducer analogs of the present invention encompasses autoinducer analogs for any organism having a quorum sensing pathway. Such organisms include gram negative and gram positive bacteria. Suitable examples include, but are not limited to, *Pseudomonas aeruginosa, Aeromonas hydrophilia, Aeromonas salmonicida, Yersinia pseudotuberculosis, Helicobacter pylori, Agrobacterium tumefaciens, Vibrio fischeri, Vibrio harveyi, Erwinia carotovora, Rhizobium leguminosarum, Rhodobacter sphaeroides*, and *Escherichia coli*. In one embodiment, the combinatorial library of the present invention encompasses autoinducer analogs for *Pseudomonas aeruginosa*.

In accordance with the present invention, the combinatorial library synthesis can be carried out either manually or through the use of an automated process. For manual synthesis, the chemical manipulations would be performed by a scientist or technician. For automated synthesis, the chemical manipulations would typically be performed robotically. The choice and implementation of such techniques is within the skill of one of ordinary skill in the art of combinatorial chemistry and will not be discussed in detail herein.

As described in detail herein, the synthesis of an autoinducer analog combinatorial library of the present invention can be performed on a solid support. As used herein, a solid support is a insoluble substrate that has been appropriately derivatized such that a chemical molecule can be attached to the surface of the substrate through standard chemical methods. Suitable solid supports include, but are not limited to, beads and particles. The solid support can include many different materials which are capable of being functionalized through synthetic methods or already include a suitable functional group. Examples of such materials include, but are not limited to, polymers, plastics, resins, polysaccharides, silicon or silica based materials, carbon, metals, inorganic glasses, and membranes. In one embodiment, the solid support is a 3,4-dihydro-2H-pyran-2-ylmethoxymethyl polystyrene (DHP resin). Other preferred solid supports include those which allow attachment of a hydroxyl group.

As described above, the solid support can be provided with a suitable functionality already present or the solid support can be chemically modified such that a desired chemical molecule is attached to the support surface. The choice of functionality used for attaching a chemical molecule to the solid support will depend on the nature of the molecule to be attached and the type of solid support. Examples of suitable functionalities on a solid support used to attach a chemical molecule to the solid support include, but are not limited to, alkyl or aryl halides, aldehydes, alcohols, ketones, amines, sulfides, carboxyl groups, aldehyde groups, and sulfonyl groups. Preferably, the functional group on the solid support in the present invention is an alcohol.

For the attachment of certain molecules to the solid support, masking of functionality that is not involved in the attachment process may be necessary. Strategies for the use of masking or protecting groups are well known in the art and will not be described in detail herein.

Figure 2:
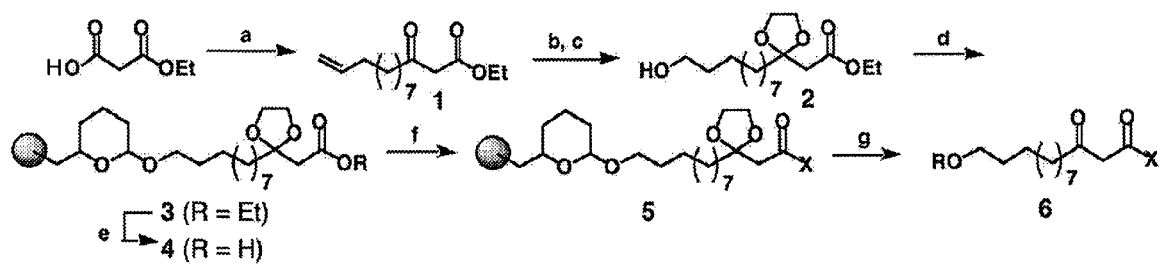
FIG. 2 shows a solid phase library synthesis scheme of the present invention. Reagents and conditions: (a) n-BuLi, THF, −78° C.; undecenoyl chloride. (b) $HOCH_2CH_2OH$, p-TsOH, benzene, reflux. (c) $BH_3$, THF, THF; $H_2O_2$, $NaHCO_3$ aq, 38% for three steps (a-c). (d) DHP resin, PPTS, $CH_2Cl_2$, room temperature, 27 hours. (e) LiOH in THF/water, 75° C., 20 hours. (f) parallel couplings with 94 amines and 2 alcohols (X), EDC, DMAP, DIPEA, DMF, room temperature, 72 hours. (g) 95% TFA, room temperature, 30 minutes, R=$CF_3CO$ or H.
Figure 3:
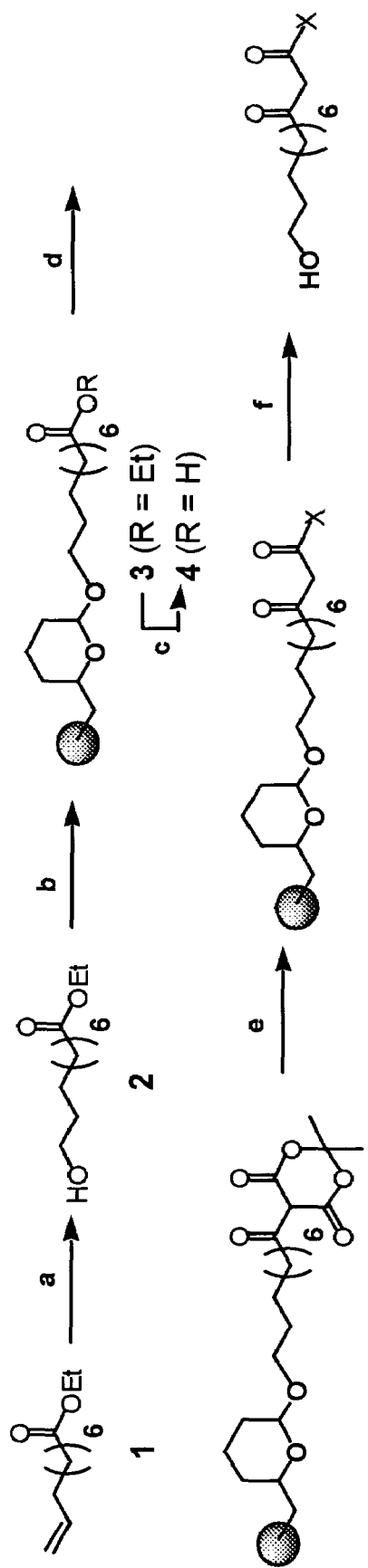
FIG. 3 shows a solid phase library synthesis scheme of the present invention. Reagents and conditions: (a) $BH_3$•THF, THF; $H_2O_2$, $NaHCO_3$ aq.; (b) DHP resin, PPTS, $CH_2Cl_2$, room temperature, 27 hours; (c) LiOH in THF/water, 75° C., 20 hours; (d) Meldrum's acid, DCC, DMAP, $CH_2Cl_2$; (e) parallel couplings with amines or alcohols (X), $Et_3N$, $CH_3CN$, reflux; (f) 95% TFA, room temperature, 30 minutes, R=$CF_3CO$ or H.
Figure 4:
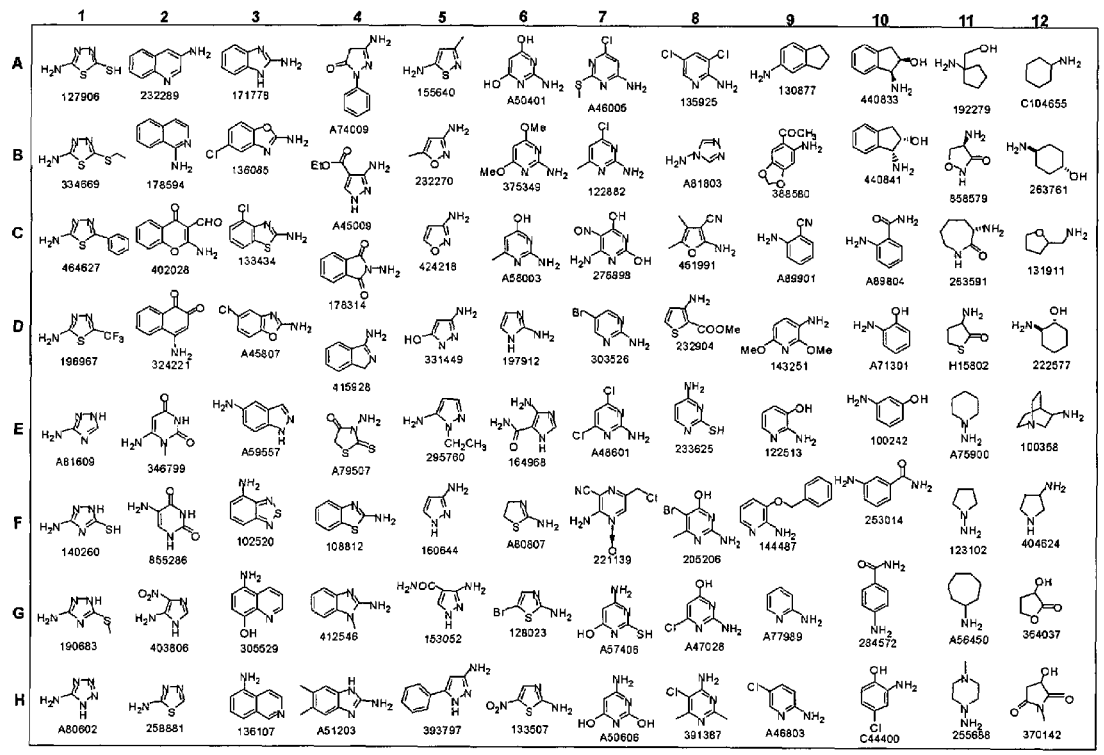
FIG. 4 shows the structures of 96 molecules used for parallel synthesis in accordance with the present invention. The Aldrich/Sigma catalog numbers are listed under the molecules.

General synthetic strategies for the construction of autoinducer analog combinatorial libraries in accordance with the present invention are shown in FIGS. 2 and 3. It should be appreciated that the chemical compounds described herein are merely exemplary and other groups can be used (e.g., different alkyl side chain lengths can be used without changing the synthetic methods). In particular, with regard to FIG. 2, an R group as set forth above (in this case a 3-oxo-$C_{12}$ side chain) was immobilized onto a solid phase and coupling with various amines and alcohols was carried out in parallel. More specifically, ethyl 3,3-ethylenedioxo-13-hydroxy-tridecanoate (2) was synthesized in solution phase through a three-step sequence. The attachment of this molecule to DHP resin (3) and on-resin hydrolysis of the ester moiety (4) was then performed. Parallel coupling of amines and alcohols having different structural features was accomplished on a 96 well reactor block. Suitable amines and alcohols are set forth in FIG. 4, however, this listing is merely representative. Any suitable molecule to produce a combinatorial library as described above may be used. The products are released from the resin by treatment with 95% TFA, which simultaneously removes the protective ketal group. The individual products are then collected into, for example, a 96 deep well plate, dried, and then passed through a tertiary alkyl amine resin to remove residual TFA.

With regard to FIG. 3, an alternative synthesis scheme is set forth. In the methodology set forth in FIG. 2, protection and deprotection steps of the 3-keto protecting group (cyclic ketal) are included. In contrast, in the methodology shown in FIG. 3, such steps are not required and, thus, the synthesis technique is shortened.

The synthesis for molecules without a 3-oxo group can be carried out in an analogous method as shown in FIG. 3, using a different starting material (with additional carbon atoms) and substituting the methods and reagents in steps (d) and (e) of FIG. 3 with those of step (f) in FIG. 2. The remaining procedures are the same as those in FIG. 3.

Thus, in one embodiment of the present invention, the autoinducer analog library is bound to a solid support. In another embodiment of the present invention, the autoinducer analog library is cleaved from the solid support. Cleavage of compounds from a solid support to produce a soluble chemical library can be accomplished using a variety of methods including hydrolysis, as described above, as well as phytolytic cleavage, nucleophilic attack, and Lewis acid-catalyzed hydrolysis. Alternatively, techniques for solution phase synthesis of a combinational library may be used, as are known in the art (Edwards et al., *Curr. Opin. Drug Discov. Devel.* 5(4):594-605 (2002), which is hereby incorporated by reference in its entirety). Solid supported libraries and solution phase libraries of the present invention may be used, for example, in the assays described below to identify autoinducer agonists and antagonists.

In another embodiment of the present invention, a position-scanning combinatorial approach is used to generate the combinatorial libraries of the present invention. Such techniques are generally known in the art. In particular, in this embodiment, once a structural motif (e.g., amine or alcohol group) identified using a library generated, for example, using the synthetic scheme of FIG. 2 or 3 is identified as possessing the desired activity (e.g., agonist or antagonist activity), a second generation library is constructed based on this information. In this second generation library, a different portion of the analog molecule (e.g., the alkyl side chain and/or the 3-oxoamide group shown in structure (6) in FIG. 2) is extensively varied into different structural elements while maintaining the previously identified structural motif (amine group or alcohol group) which displayed the desired activity. The new library (and any further libraries) can then be screened for increased activity. The number of compounds tested is the product of the number of varied structural elements in all of the libraries produced.

The autoinducer analogs produced in accordance with the present invention can be used to enhance bacterial growth by acting in concert with or instead of the wild-type autoinducer (i.e., an autoinducer agonist). Alternatively, the autoinducer analog can inhibit the wild-type autoinducer by competing with the wild-type autoinducer in the quorum sensing pathway (i.e., an autoinducer antagonist).

Thus, the present invention also relates to an autoinducer agonist or antagonist having the structure

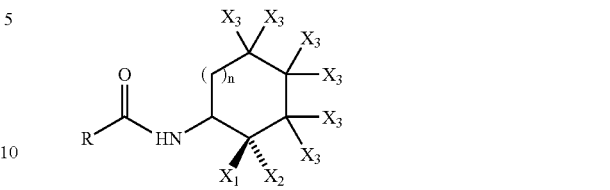

wherein $X_1$ is selected from the group consisting of H and OH, $X_2$ is selected from the group consisting of H and OH, $X_3$ is independently selected from the group consisting of H, OH, SH, $OR^1$, $SR^1$, $NH_2$, $NHR^1$, $NR^1R^2$, $COOR^1$, alkyl, cycloalkyl, alkenyl, alkynyl, aryl, heteroaryl, heteroalicyclic, acyl group, carbonyl, cyano, nitro, halogen, and, adjacent $X_3$ substituents combined, a cycloalkyl of 3 to 8 carbon atoms, a heterocycloalkyl of 3 to 8 members comprising carbon atoms and from 1 to 6 heteroatoms selected from the group consisting of N, S, and O, and an aryl or heteroaryl ring having 3 to 8 members, wherein $R^1$ and $R^2$ are selected from the group consisting of H, alkyl, cycloalkyl, alkenyl, aryl, heteroaryl, carbonyl, and sulfonyl, n is 0 to 4; or

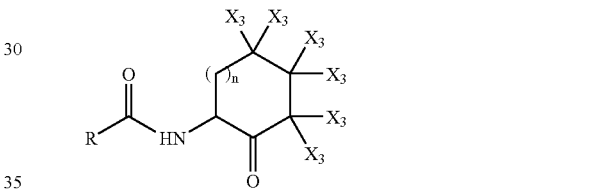

wherein $X_3$ is independently selected from the group consisting of H, OH, SH, $OR^1$, $SR^1$, $NH_2$, $NHR^1$, $NR^1R^2$, $COOR^1$, alkyl, cycloalkyl, alkenyl, alkynyl, aryl, heteroaryl, heteroalicyclic, acyl group, carbonyl, cyano, nitro, halogen, and, adjacent $X_3$ substituents combined, a cycloalkyl of 3 to 8 carbon atoms, a heterocycloalkyl of 3 to 8 members comprising carbon atoms and from 1 to 6 heteroatoms selected from the group consisting of N, S, and O, and an aryl or heteroaryl ring having 3 to 8 members, wherein $R^1$ and $R^2$ are selected from the group consisting of H, alkyl, cycloalkyl, alkenyl, aryl, heteroaryl, carbonyl, and sulfonyl, and n is 0 to 4; or

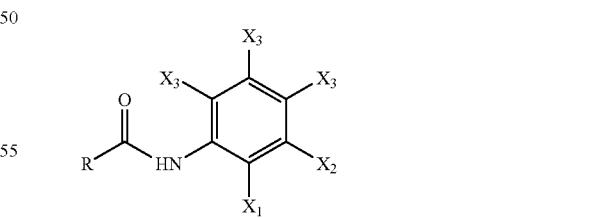

wherein $X_1$, $X_2$, and $X_3$ are independently selected from the group consisting of H, OH, SH, $OR^1$, $SR^1$, $NH_2$, $NHR^1$, $NR^1R^2$, $COOR^1$, alkyl, cycloalkyl, alkenyl, alkynyl, aryl, heteroaryl, heteroalicyclic, acyl group, carbonyl, cyano, nitro, halogen, and, adjacent $X_1$, $X_2$, and $X_3$ substituents combined, a cycloalkyl of 3 to 8 carbon atoms, a heterocycloalkyl of 3 to 8 members comprising carbon atoms and from 1 to 6 heteroatoms selected from the group consisting of N, S, and O, and an aryl or heteroaryl ring having 3 to 8 members, wherein $R^1$ and $R^2$ are selected from the group consisting of H, alkyl, cycloalkyl, alkenyl, aryl, heteroaryl, carbonyl, and sulfonyl; or

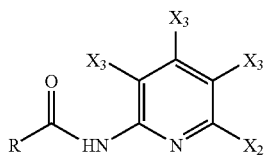

wherein $X_2$ and $X_3$ are independently selected from the group consisting of H, OH, SH, $OR^1$, $SR_1$, $NH_2$, $NHR^1$, $NR^1R^2$, $COOR^1$, alkyl, cycloalkyl, alkenyl, alkynyl, aryl, heteroaryl, heteroalicyclic, acyl group, carbonyl, cyano, nitro, halogen, and, adjacent $X_2$ and $X_3$ substituents combined, a cycloalkyl of 3 to 8 carbon atoms, a heterocycloalkyl of 3 to 8 members comprising carbon atoms and from 1 to 6 heteroatoms selected from the group consisting of N, S, and O, and an aryl or heteroaryl ring having 3 to 8 members, wherein $R^1$ and $R^2$ are selected from the group consisting of H, alkyl, cycloalkyl, alkenyl, aryl, heteroaryl, carbonyl, and sulfonyl, and wherein R is selected from the group consisting of $C_mH_{2m+1}$, wherein m is 1 to 14,

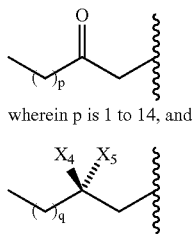

wherein p is 1 to 14, and wherein q is 1 to 14, $X^4$ is OH, $NH_2$, or SH and $X_5$ is H, or $X_4$ is H and $X_5$ is OH, $NH_2$, or SH. In one embodiment, n is 1 to 4.

Figure 6:
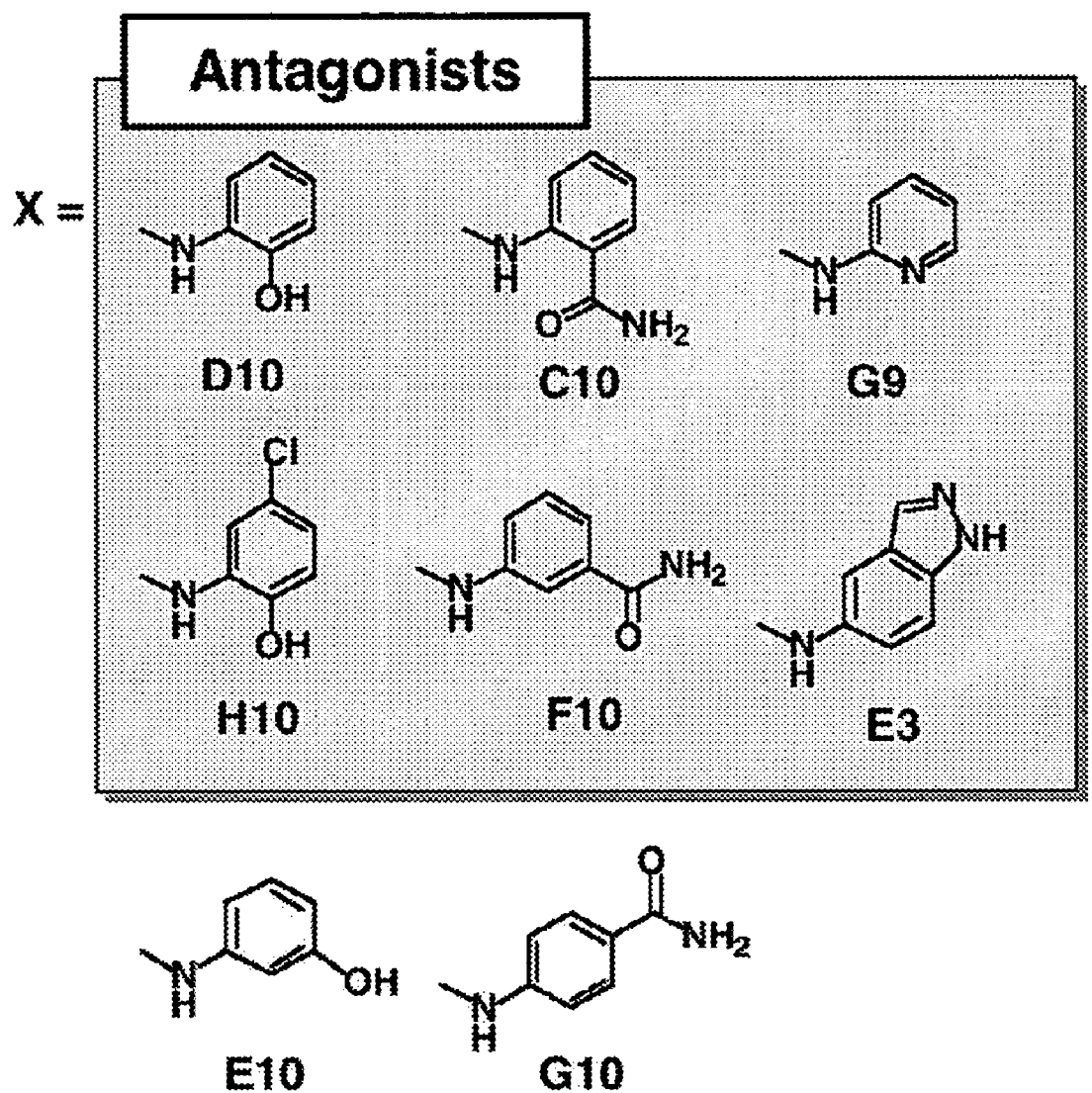
FIG. 6 shows the structure of antagonists and similar compounds with agonist or no activity.
Figure 7:
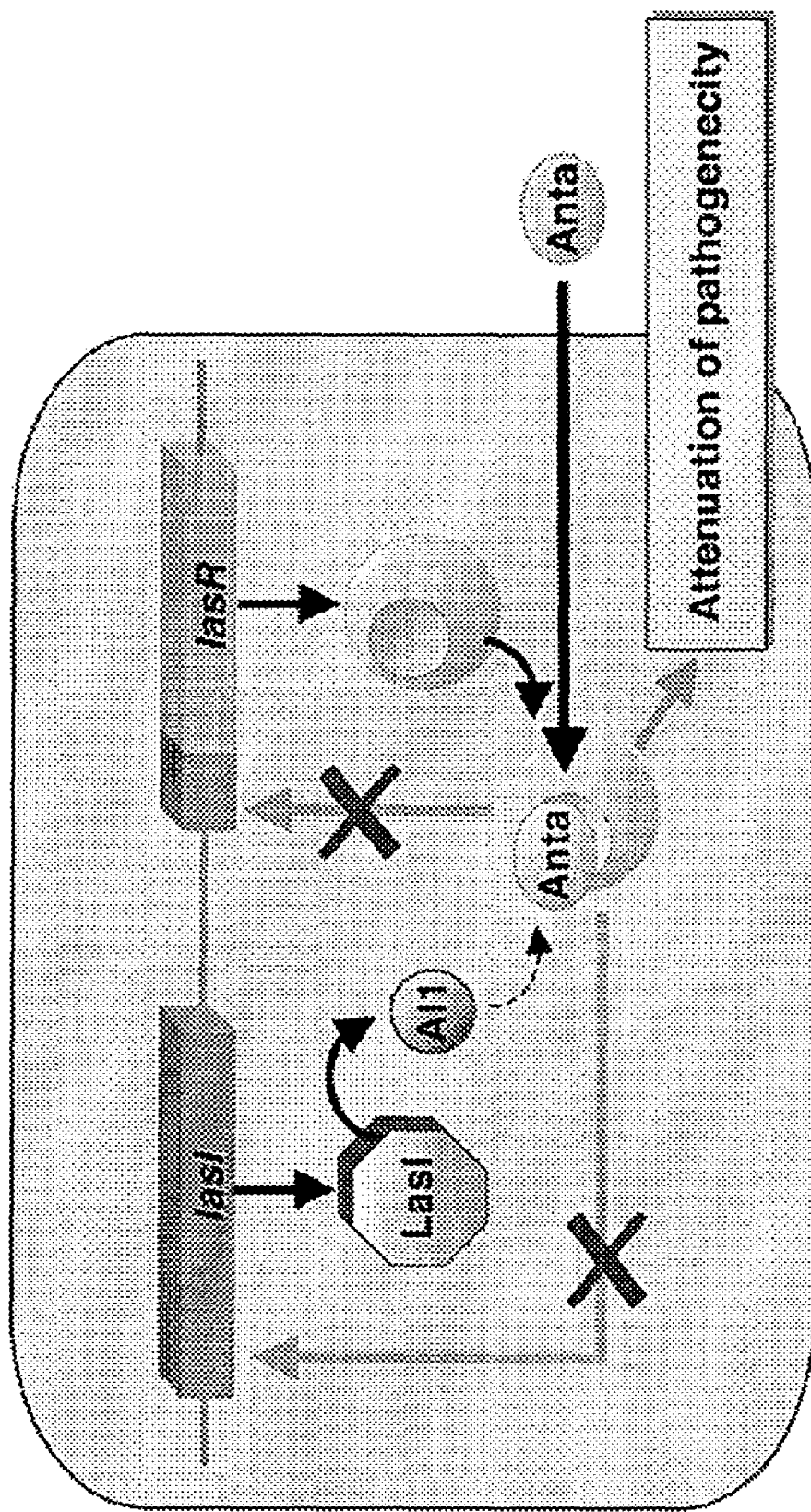
FIG. 7 is a schematic showing the inhibition of quorum sensing that attenuates pathogenicity. Anta abbreviates antagonist.
Figure 18:
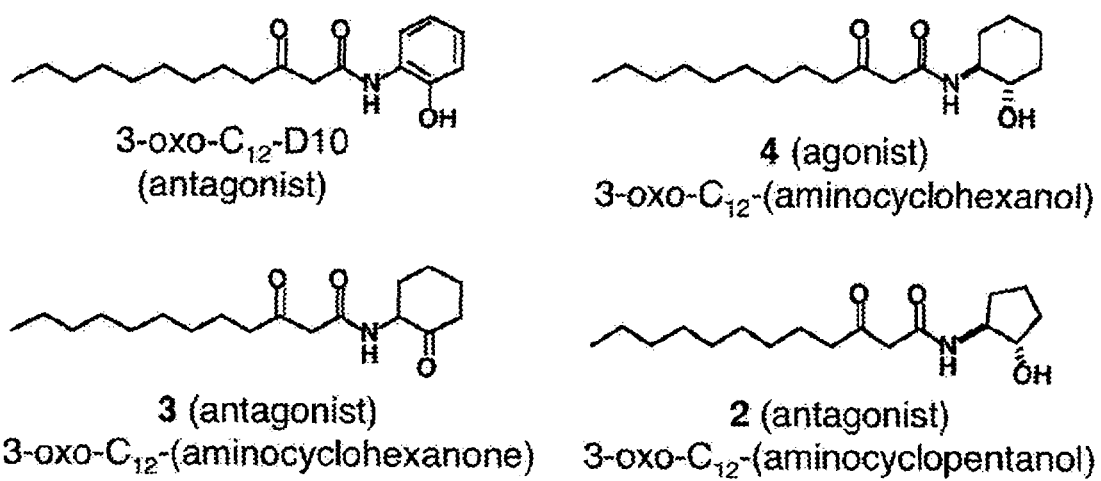
FIG. 18 shows agonist and antagonists in *P. aeruginosa* QS circuits found in accordance with the present invention.

Preferred autoinducer agonists of the present invention are set forth in FIG. 5B and are described in detail in the Examples, below. Preferred autoinducer antagonists of the present invention are set forth in FIG. 6 and are described in detail in the Examples, below. As described in detail below, autoinducer antagonists of the present invention can be used to attenuate the pathogenicity of an organism possessing the quorum sensing mechanism (see also FIG. 7). Additional preferred autoinducer agonists and antagonists are set forth in FIG. 18 and are described in Example 11, below. As described herein, in one embodiment, the agonists and antagonists have a hydrogen bond donor or acceptor adjacent to the amino group that connects to the R side chain.

The autoinducer analogs identified in accordance with the present invention (e.g. autoinducer agonists or antagonists) can be used in compositions which include one or more autoinducer analogs. In one embodiment, the composition also includes an antibiotic. Suitable antibiotics include bactericidal and bacteristatic agents, such as sulfonamides, antiurinary tract agents, β-lactam antibiotics, quinolones, cephalosporins, clavulanic acid derivatives, aminoglycosides, carbapenems, tetracyclines and related antibacterial agents, macrolides, anti-tuberculosis drugs, anti-mycobacterium avium agents, anti-leprosy agents, antifungal agents, and antiviral agents. In this embodiment, the autoinducer analog is preferably an autoinducer antagonist. The autoinducer antagonist may be present in the composition in an amount of from about 10 ng/L to about 10 mg/L and the antibiotic may be present in the composition in an amount of from about 10 ng/L to about 10 mg/L, however, any desirable quantity of autoinducer antagonist or antibiotic may be used.

Such compositions are useful for inhibition of growth of an organism possessing a quorum sensing pathway. One example of such as use is in medical devices used both percutaneously and implanted within a patient. Such medical devices commonly serve as loci for bacterial infection. Thus, the autoinducer analogs and compositions of the present invention can be used to inhibit growth of an organism possessing a quorum sensing pathway on a medical device associated with non-invasive or invasive medical procedures. Such medical devices include, but are not limited to, catheters, pacemakers, vascular grafts, vascular stents, dialysis membranes, heart valves, surgical instruments, blood bags, sutures, prostheses, dental devices, and artificial organs.

The autoinducer analogs and compositions can be incorporated (e.g., impregnated or infused) within the structure of the medical device (e.g., chemically incorporated within an outer layer of a medical device) or provided as a coating on the medical device. Techniques suitable for incorporating the autoinducer analogs and compositions of the present invention within a medical device depend upon the particular autoinducer analog/composition used and the medical device used. Techniques suitable for providing a coating on a medical device substrate are well known in the art and will not be discussed in detail herein.

The medical device may be further supplemented with any other desirable compound, for example, antibiotics, analgesics, anticoagulants, anti-inflammatory compounds, antimicrobial compositions, vitamins, minerals, and the like.

The autoinducer analogs and compositions can also be used to inhibit growth of an organism possessing a quorum sensing pathway on any product or device that comes into contact with human (or other mammalian) tissue, such as a toothbrush or dental floss.

Moreover, the autoinducer analogs and compositions of the present invention may also be used as immunosuppressive agents (see Telford et al., *Infect. Immun.* 66(1):36-42 (1998), which is hereby incorporated by reference in its entirety).

Yet another aspect of the present invention relates to a method of identifying an autoinducer agonist. This method involves providing an autoinducer analog having the structure

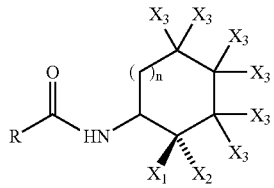

wherein $X_1$ is selected from the group consisting of H and OH, $X_2$ is selected from the group consisting of H and OH, $X_3$ is independently selected from the group consisting of H, OH, SH, $OR^1$, $SR_1$, $NH_2$, $NHR^1$, $NR^1R^2$, $COOR^1$, alkyl, cycloalkyl, alkenyl, alkynyl, aryl, heteroaryl, heteroalicyclic, acyl group, carbonyl, cyano, nitro, halogen, and, adjacent $X_3$ substituents combined, a cycloalkyl of 3 to 8 carbon atoms, a heterocycloalkyl of 3 to 8 members comprising carbon atoms and from 1 to 6 heteroatoms selected from the group consisting of N, S, and O, and an aryl or heteroaryl ring having 3 to 8 members, wherein $R^1$ and $R^2$ are selected from the group consisting of H, alkyl, cycloalkyl, alkenyl, aryl, heteroaryl, carbonyl, and sulfonyl, and n is 0 to 4; or

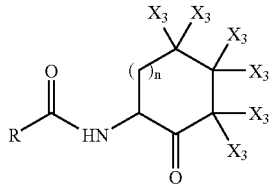

wherein $X_3$ is independently selected from the group consisting of H, OH, SH, $OR^1$, $SR_1$, $NH_2$, $NHR^1$, $NR^1R^2$, $COOR^1$, alkyl, cycloalkyl, alkenyl, alkynyl, aryl, heteroaryl, heteroalicyclic, acyl group, carbonyl, cyano, nitro, halogen, and, adjacent $X_3$ substituents combined, a cycloalkyl of 3 to 8 carbon atoms, a heterocycloalkyl of 3 to 8 members comprising carbon atoms and from 1 to 6 heteroatoms selected from the group consisting of N, S, and O, and an aryl or heteroaryl ring having 3 to 8 members, wherein $R^1$ and $R^2$ are selected from the group consisting of H, alkyl, cycloalkyl, alkenyl, aryl, heteroaryl, carbonyl, and sulfonyl, and n is 0 to 4; or

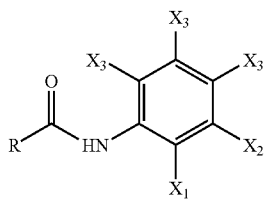

wherein $X_1$, $X_2$, and $X_3$ are independently selected from the group consisting of H, OH, SH, $OR^1$, $SR_1$, $NH_2$, $NHR^1$, $NR^1R^2$, $COOR^1$, alkyl, cycloalkyl, alkenyl, alkynyl, aryl, heteroaryl, heteroalicyclic, acyl group, carbonyl, cyano, nitro, halogen, and, adjacent $X_1$, $X_2$, and $X_3$ substituents combined, a cycloalkyl of 3 to 8 carbon atoms, a heterocycloalkyl of 3 to 8 members comprising carbon atoms and from 1 to 6 heteroatoms selected from the group consisting of N, S, and O, and an aryl or heteroaryl ring having 3 to 8 members, wherein $R^1$ and $R^2$ are selected from the group consisting of H, alkyl, cycloalkyl, alkenyl, aryl, heteroaryl, carbonyl, and sulfonyl; or

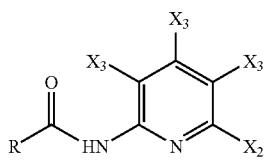

wherein $X_2$ and $X_3$ are independently selected from the group consisting of H, OH, SH, $OR^1$, $SR_1$, $NH_2$, $NHR^1$, $NR^1R^2$, $COOR^1$, alkyl, cycloalkyl, alkenyl, alkynyl, aryl, heteroaryl, heteroalicyclic, acyl group, carbonyl, cyano, nitro, halogen, and, adjacent $X_2$ and $X_3$ substituents combined, a cycloalkyl of 3 to 8 carbon atoms, a heterocycloalkyl of 3 to 8 members comprising carbon atoms and from 1 to 6 heteroatoms selected from the group consisting of N, S, and O, and an aryl or heteroaryl ring having 3 to 8 members, wherein $R^1$ and $R^2$ are selected from the group consisting of H, alkyl, cycloalkyl, alkenyl, aryl, heteroaryl, carbonyl, and sulfonyl, and wherein R is selected from the group consisting of $C_mH_{2m+1}$, wherein m is 1 to 14,

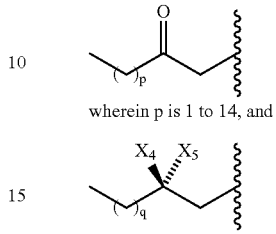

wherein p is 1 to 14, and

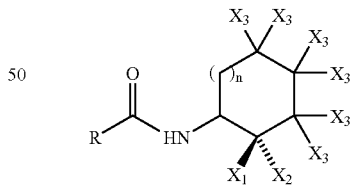

wherein q is 1 to 14, $X_4$ is OH, $NH_2$, or SH and $X_5$ is H, or $X_4$ is H and $X_5$ is OH, $NH_2$, or SH. In one embodiment, n is 1 to 4. The autoinducer analog is contacted with an autoinducer receptor and activity of the receptor is measured in the presence of the autoinducer analog. The autoinducer analog can be provided as part of a combinatorial library, as described above.

In a preferred embodiment, an autoinducer analog is identified using a organism strain lacking the ability to produce one or more natural autoinducers, due to the disruption of any autoinducer synthase genes. Thus, activation of autoinducer receptors in such strains relies on the addition of exogenous autoinducer. Such strains include, but are not limited to, *P. aeruginosa* PAO-JP2 and *E. coli* MG4 (pKDT37).

Activity of the receptor can be measured using any suitable reporter assay. In particular, a reporter may be incorporated into the above strain as is known in the art, such that the strain is capable of providing a signal (e.g., luminescence or enzyme activity) in the presence of autoinducer or an autoinducer agonist. Suitable reporters include, but are not limited to, gfp and lacZ. Activity of the receptor in the presence of the autoinducer analog can be compared to known activities of other autoinducer agonists or the autoinducer itself.

A further aspect of the present invention relates to a method of identifying an autoinducer antagonist. This method involves providing an autoinducer analog having the structure wherein $X_1$ is selected from the group consisting of H and OH, $X_2$ is selected from the group consisting of H and OH, $X_3$ is independently selected from the group consisting of H, OH, SH, $OR^1$, $SR^1$, $NH_2$, $NHR^1$, $NR^1R^2$, $COOR^1$, alkyl, cycloalkyl, alkenyl, alkynyl, aryl, heteroaryl, heteroalicyclic, acyl group, carbonyl, cyano, nitro, halogen, and, adjacent $X_3$ substituents combined, a cycloalkyl of 3 to 8 carbon atoms, a heterocycloalkyl of 3 to 8 members comprising carbon atoms and from 1 to 6 heteroatoms selected from the group consisting of N, S, and O, and an aryl or heteroaryl ring having 3 to 8 members, wherein $R^1$ and $R^2$ are selected from the group consisting of H, alkyl, cycloalkyl, alkenyl, aryl, heteroaryl, carbonyl, and sulfonyl, and n is 0 to 4; or

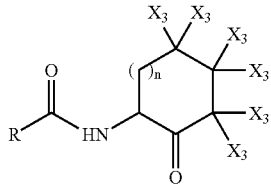

wherein $X_3$ is independently selected from the group consisting of H, OH, SH, $OR^1$, $SR_1$, $NH_2$, $NHR^1$, $NR^1R^2$, $COOR^1$, alkyl, cycloalkyl, alkenyl, alkynyl, aryl, heteroaryl, heteroalicyclic, acyl group, carbonyl, cyano, nitro, halogen, and, adjacent $X_3$ substituents combined, a cycloalkyl of 3 to 8 carbon atoms, a heterocycloalkyl of 3 to 8 members comprising carbon atoms and from 1 to 6 heteroatoms selected from the group consisting of N, S, and O, and an aryl or heteroaryl ring having 3 to 8 members, wherein $R^1$ and $R^2$ are selected from the group consisting of H, alkyl, cycloalkyl, alkenyl, aryl, heteroaryl, carbonyl, and sulfonyl, and n is 0 to 4; or

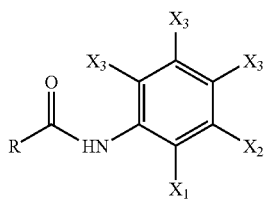

wherein $X_1$, $X_2$, and $X_3$ are independently selected from the group consisting of H, OH, SH, $OR^1$, $SR^1$, $NH_2$, $NHR^1$, $NR^1R^2$, $COOR^1$, alkyl, cycloalkyl, alkenyl, alkynyl, aryl, heteroaryl, heteroalicyclic, acyl group, carbonyl, cyano, nitro, halogen, and, adjacent $X_1$, $X_2$, and $X_3$ substituents combined, a cycloalkyl of 3 to 8 carbon atoms, a heterocycloalkyl of 3 to 8 members comprising carbon atoms and from 1 to 6 heteroatoms selected from the group consisting of N, S, and O, and an aryl or heteroaryl ring having 3 to 8 members, wherein $R^1$ and $R^2$ are selected from the group consisting of H, alkyl, cycloalkyl, alkenyl, aryl, heteroaryl, carbonyl, and sulfonyl; or

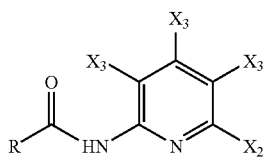

wherein $X_2$ and $X_3$ are independently selected from the group consisting of H, OH, SH, $OR^1$, $SR^1$, $NH_2$, $NHR^1$, $NR^1R^2$, $COOR^1$, alkyl, cycloalkyl, alkenyl, alkynyl, aryl, heteroaryl, heteroalicyclic, acyl group, carbonyl, cyano, nitro, halogen, and, adjacent $X_2$ and $X_3$ substituents combined, a cycloalkyl of 3 to 8 carbon atoms, a heterocycloalkyl of 3 to 8 members comprising carbon atoms and from 1 to 6 heteroatoms selected from the group consisting of N, S, and O, and an aryl or heteroaryl ring having 3 to 8 members, wherein $R^1$ and $R^2$ are selected from the group consisting of H, alkyl, cycloalkyl, alkenyl, aryl, heteroaryl, carbonyl, and sulfonyl, and wherein R is selected from the group consisting of $C_mH_{2m+1}$, wherein m is 1 to 14,

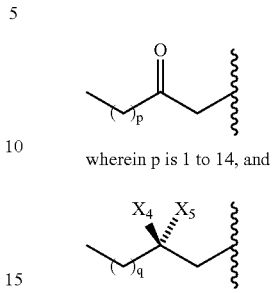

wherein p is 1 to 14, and

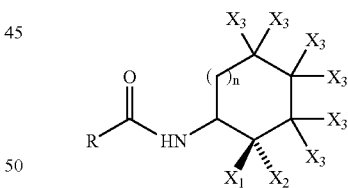

wherein q is 1 to 14, $X_4$ is OH, $NH_2$, or SH and $X_5$ is H, or $X_4$ is H and $X_5$ is OH, $NH_2$, or SH. In one embodiment, n is 1 to 4. The autoinducer analog is contacted with an autoinducer receptor and an autoinducer, whereby competition between the autoinducer analog and the autoinducer for the autoinducer receptor is allowed to occur. Activity of the receptor in the presence of the autoinducer analog and autoinducer is then measured and compared with activity of the receptor in the presence of only the autoinducer. Suitable reporter assays for use in this method of the present invention are described above. The autoinducer analog can be provided as part of a combinatorial library, as described above.

Yet another aspect of the present invention relates to a method for regulating the activity of an autoinducer receptor. This method involves contacting an autoinducer receptor with an autoinducer analog, wherein the autoinducer analog is an autoinducer agonist or antagonist. In one embodiment, the autoinducer analog is an autoinducer-1 (AI1) agonist or antagonist compound. In another embodiment, the autoinducer analog is an autoinducer-2 (AI2) agonist or antagonist compound. In a further embodiment, the autoinducer analog has the structure wherein $X_1$ is selected from the group consisting of H and OH, $X_2$ is selected from the group consisting of H and OH, $X_3$ is independently selected from the group consisting of H, OH, SH, $OR^1$, $SR_1$, $NH_2$, $NHR^1$, $NR^1R^2$, $COOR^1$, alkyl, cycloalkyl, alkenyl, alkynyl, aryl, heteroaryl, heteroalicyclic, acyl group, carbonyl, cyano, nitro, halogen, and, adjacent $X_3$ substituents combined, a cycloalkyl of 3 to. 8 carbon atoms, a heterocycloalkyl of 3 to 8 members comprising carbon atoms and from 1 to 6 heteroatoms selected from the group consisting of N, S, and O, and an aryl or heteroaryl ring having 3 to 8 members, wherein $R^1$ and $R^2$ are selected from the group consisting of H, alkyl, cycloalkyl, alkenyl, aryl, heteroaryl, carbonyl, and sulfonyl, and n is 0 to 4; or

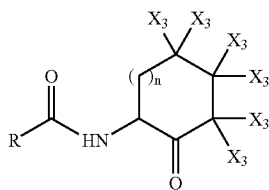

wherein X₃ is independently selected from the group consisting of H, OH, SH, OR¹, SR¹, NH₂, NHR¹, NR¹R², COOR¹, alkyl, cycloalkyl, alkenyl, alkynyl, aryl, heteroaryl, heteroalicyclic, acyl group, carbonyl, cyano, nitro, halogen, and, adjacent X₃ substituents combined, a cycloalkyl of 3 to 8 carbon atoms, a heterocycloalkyl of 3 to 8 members comprising carbon atoms and from 1 to 6 heteroatoms selected from the group consisting of N, S, and O, and an aryl or heteroaryl ring having 3 to 8 members, wherein R¹ and R² are selected from the group consisting of H, alkyl, cycloalkyl, alkenyl, aryl, heteroaryl, carbonyl, and sulfonyl, and n is 0 to 4; or

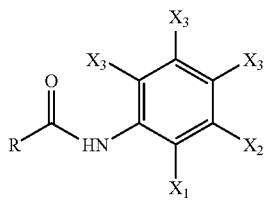

wherein X₁, X₂, and X₃ are independently selected from the group consisting of H, OH, SH, OR¹, SR₁, NH₂, NHR¹, NR¹R², COOR¹, alkyl, cycloalkyl, alkenyl, alkynyl, aryl, heteroaryl, heteroalicyclic, acyl group, carbonyl, cyano, nitro, halogen, and, adjacent X₁, X₂, and X₃ substituents combined, a cycloalkyl of 3 to 8 carbon atoms, a heterocycloalkyl of 3 to 8 members comprising carbon atoms and from 1 to 6 heteroatoms selected from the group consisting of N, S, and O, and an aryl or heteroaryl ring having 3 to 8 members, wherein R¹ and R² are selected from the group consisting of H, alkyl, cycloalkyl, alkenyl, aryl, heteroaryl, carbonyl, and sulfonyl; or

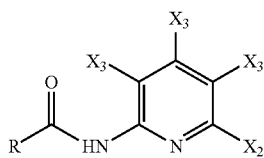

wherein X₂ and X₃ are independently selected from the group consisting of H, OH, SH, OR¹, SR¹, NH₂, NHR¹, NR¹R², COOR¹, alkyl, cycloalkyl, alkenyl, alkynyl, aryl, heteroaryl, heteroalicyclic, acyl group, carbonyl, cyano, nitro, halogen, and, adjacent X₂ and X₃ substituents combined, a cycloalkyl of 3 to 8 carbon atoms, a heterocycloalkyl of 3 to 8 members comprising carbon atoms and from 1 to 6 heteroatoms selected from the group consisting of N, S, and O, and an aryl or heteroaryl ring having 3 to 8 members, wherein R¹ and R² are selected from the group consisting of H, alkyl, cycloalkyl, alkenyl, aryl, heteroaryl, carbonyl, and sulfonyl, and wherein R is selected from the group consisting of $C_mH_{2m+1}$, wherein m is 1 to 14,

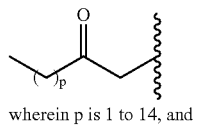

wherein p is 1 to 14, and

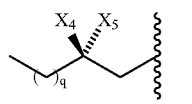

wherein q is 1 to 14, X₄ is OH, NH₂, or SH and X₅ is H, or X₄ is H and X₅ is OH, NH₂, or SH, whereby activity of the receptor is regulated. In one embodiment, n is 1 to 4.

In one embodiment of the present invention, the autoinducer receptor is found in a gram negative or gram positive bacterium, as described above, which may or may not be present within a host. In another embodiment of the present invention, the autoinducer receptor is LasR, LasI, RhlR, or RhlI of *P. aeruginosa*. However, other suitable receptors include, but are not limited to, LuxR and LuxI (of *V. fischeri*), and all LuxR and LuxI homologs (e.g., LuxP and LuxQ) (see, e.g., Miller et al., *Annu. Rev. Microbiol.* 55:165-199 (2001); Dunny et al., "Cell-toCell Signaling in Bacteria," *American Society for Microbiology*, Washington D.C. (1999), which are hereby incorporated by reference in their entirety). As used herein, regulating may comprise activating the receptor or inhibiting the receptor.

A further aspect of the present invention relates to a method of regulating biofilm formation. This method involves contacting a cell of an organism with an autoinducer analog as described above with regard to the method for regulating an autoinducer receptor, whereby biofilm formation on the cell is regulated. In one embodiment of the present invention, biofilm formation is inhibited. In another embodiment of the present invention, biofilm architecture is modified by contact with the autoinducer analog. As described above, the biofilm is a complex, polysaccharide-laden microniche that protects the bacterial from both antibiotics and the host's humoral and cell-mediated responses. Thus, the inhibition of biofilm formation or the alteration of the biofilm may result in less infectious bacterial strains which would be easier targets for antibiotics and host defenses.

The present invention also relates to a method for regulating the growth or virulence of an organism in a subject. This method involves contacting a cell of an organism with an autoinducer analog as described above with regard to the method for regulating an autoinducer receptor, whereby growth or virulence of the organism is regulated. As described above, the autoinducer analog of the present invention can be used to enhance organism (e.g., bacterial) growth by acting in concert with or instead of the wild-type autoinducer (i.e., as an autoinducer agonist) or to inhibit organism (e.g., bacterial) growth by competing with the wild-type autoinducer (i.e., as an autoinducer antagonist). In addition, the autoinducer analog of the present invention can inhibit virulence through inhibition of the interaction between secreted quorum sensing molecules (autoinducers) of an organism and their cognate transcriptional regulator proteins, thereby inhibiting the production of virulence factors (see FIG. 1 and the description in the Examples below).

Another aspect of the present invention relates to a method of inhibiting a quorum sensing mechanism in an organism. This method involves contacting a cell of an organism possessing a quorum sensing mechanism with an autoinducer analog as described above with regard to the method for regulating an autoinducer receptor, whereby the quorum sensing mechanism of the organism is inhibited.

The aforementioned autoinducer analogs and compositions are also useful in treating an infection in a subject caused by an organism possessing a quorum sensing mechanism by administering an effective amount of an autoinducer analog or composition including an autoinducer analog to the subject. The autoinducer analog or composition can, for example, prevent the transcriptional activation of virulence factors, such as Elastase A, Elastase B, exotoxin A, pyoverdine, pyocyanin, and other virulence factors, such as those described in PCT International Publication No. WO 01/85664, which is hereby incorporated by reference in its entirety. In addition, the autoinducer analog or composition can, for example, inhibit biofilm formation or alter biofilm architecture for an organism possessing the quorum sensing mechanism and/or kill the organism possessing the quorum sensing mechanism by, for example, a NO-mediated suicidal mechanism. Thus, this method of the present invention is useful for treating any subject capable of being infected by an organism possessing a quorum sensing mechanism, such as mammals and plants, and, in particular, humans. The autoinducer analog can be administered alone, or in combination with suitable pharmaceutical carriers or diluents. The diluent or carrier ingredients should be selected so that they do not diminish the therapeutic effects of the autoinducer analogs or compositions. Suitable pharmaceutical compositions include those which include a pharmaceutical carrier and, for example, one or more of an autoinducer analog, as described herein.

The autoinducer analogs and compositions herein can be made up in any suitable form appropriate for the desired use; e.g., oral, parenteral, or topical administration. Examples of parenteral administration are intraventricular, intracerebral, intramuscular, intravenous, intraperitoneal, rectal, and subcutaneous administration. The preferred route for administration is intravenous. In cases where the autoinducer analogs or compositions are administered topically or parenterally, it is preferred that they be pre-hydrolyzed.

Suitable dosage forms for oral use include tablets, dispersible powders, granules, capsules, suspensions, syrups, and elixirs. Inert diluents and carriers for tablets include, for example, calcium carbonate, sodium carbonate, lactose, and talc. Tablets may also contain granulating and disintegrating agents, such as starch and alginic acid; binding agents, such as starch, gelatin, and acacia; and lubricating agents, such as magnesium stearate, stearic acid, and talc. Tablets may be uncoated or may be coated by known techniques to delay disintegration and absorption. Inert diluents and carriers which may be used in capsules include, for example, calcium carbonate, calcium phosphate, and kaolin. Suspensions, syrups, and elixirs may contain conventional excipients, such as methyl cellulose, tragacanth, sodium alginate; wetting agents, such as lecithin and polyoxyethylene stearate; and preservatives, such as ethyl-p-hydroxybenzoate. Dosage forms suitable for parenteral administration include solutions, suspensions, dispersions, emulsions, and the like. They may also be manufactured in the form of sterile solid compositions which can be dissolved or suspended in sterile injectable medium immediately before use. They may contain suspending or dispersing agents known in the art.

For oral administration either solid or fluid unit dosage forms can be prepared. For preparing solid compositions, such as tablets, a suitable autoinducer analog or composition, as disclosed above, is mixed with conventional ingredients, such as talc, magnesium stearate, dicalcium phosphate, magnesium aluminum silicate, calcium sulfate, starch, lactose, acacia methylcellulose, and functionally similar materials as pharmaceutical diluents or carriers. Capsules are prepared by mixing the disclosed autoinducer analogs or compositions with an inert pharmaceutical diluent and filling the mixture into a hard gelatin capsule of appropriate size. Soft gelatin capsules are prepared by machine encapsulation of a slurry of the autoinducer analog or composition with an acceptable vegetable oil, light liquid petrolatum, or other inert oil.

Fluid unit dosage forms for oral administration such as syrups, elixirs, and suspensions can be prepared. The water-soluble forms can be dissolved in an aqueous vehicle together with sugar, aromatic flavoring agents, and preservatives to form a syrup. An elixir is prepared by using a hydro-alcoholic (ethanol) vehicle with suitable sweeteners, such as sugar and saccharin, together with an aromatic flavoring agent. Suspensions can be prepared with a syrup vehicle with the aid of a suspending agent, such as acacia, tragacanth, methylcellulose, and the like.

For parenteral administration, fluid unit dosage forms are prepared utilizing the aforementioned autoinducer analogs or compositions and a sterile vehicle, water being preferred. The autoinducer analog or composition, depending on the vehicle and concentration used, can be either suspended or dissolved in the vehicle. In preparing solutions, the autoinducer analog or composition can be dissolved in water for injection and filter sterilized before filling into a suitable vial or ampule and sealing. Advantageously, adjuvants, such as a local anesthetic, preservative, and buffering agents, can be dissolved in the vehicle. To enhance the stability, the fluid unit dosage form can be frozen after filling into the vial, and the water removed under vacuum. The dry lyophilized powder is then sealed in the vial, and an accompanying vial of water for injection is supplied to reconstitute the liquid prior to use. Parenteral suspensions are prepared in substantially the same manner except that the autoinducer analog or composition is suspended in the vehicle instead of being dissolved, and sterilization cannot be accomplished by filtration. The autoinducer analog or composition can be sterilized by exposure to ethylene oxide before suspending in the sterile vehicle. Advantageously, a surfactant or wetting agent is included in the parenteral suspension to facilitate uniform distribution of the autoinducer analog or composition.

Suitable daily dosages can be based on suitable doses of antibiotics (e.g., carbapenems). Typically, suitable daily doses are from about 10 ng/mL to about 10 mg/mL of the autoinducer analog or composition (e.g., about 300 mg total for a human). Alternatively, the autoinducer analogs or compositions can be administered orally in foodstuffs.

Alternatively, the autoinducer analog or composition can be incorporated into a sustained release formulation and surgically implanted using conventional methods. Suitable sustained release matrices include those made of ethylene vinyl acetate and other biocompatible polymers.

For topical administration, carriers, such as phospholipid vesicles, which contain the aforementioned autoinducer analogs or composition may facilitate uptake through the skin.

The present invention is further illustrated by the following examples.

EXAMPLES

Example 1—Library Synthesis

In previously reported works, autoinducer analogs were synthesized individually and modified mainly on the alky side chain of AI1 (Passador et al., *J. Bacteriol.* 178:5995-6000 (1996); Kline et al., *Bioorg. Med. Chem. Lett.* 9:3447-3452 (1999), which are hereby incorporated by reference in their entirety). Although these attempts revealed the importance of the side chain for activity, no potent antagonist was discovered. On the other hand, very few investigations were made altering the HSL moiety. The only significant findings were that substitution of HSL with homocysteine thiolactone is as active as AI1, whereas the corresponding lactam has nearly no QS activity (Passador et al., *J. Bacteriol* 178:5995-6000 (1996), which is hereby incorporated by reference in its entirety). Again, no potent antagonists were found.

To this end, 96 different autoinducer analogs with various substituents at the HSL position were synthesized as shown in FIG. 2 and as described below.

General Synthetic Methods 3,4-dihydro-2H-pyran-2-ylmethoxymethyl polystyrene (DHP resin) was purchased from Novabiochem (Laufelfingen, SWI). All other chemicals were purchased from Sigma-Aldrich (Milwaukee, Wis.) or Acros. All the solvents were anhydrous grade, or were distilled before use. All reactions were carried out in oven-dried glassware under an argon atmosphere, except the ones containing water. Anhydrous $MgSO_4$ was used as drying agent for all products. Analytical thin layer chromatography was performed on EM Reagent 0.25 mm silica gel 60-F plate. Flash chromatography was performed using EM silica gel 60 (230-400 mesh). Parallel synthesis was performed using a reactor block from Robbins Scientific Inc. (Sunnyvale, Calif.). Mass spectra were recorded on a Finnigan MAT95 XL spectrometer (San Jose, Calif.). NMR spectra were taken on a Varian Gemini 300, Inova 400, or Inova 500 MHz spectrometer (Palo Alto, Calif.). $^1H$ chemical shifts were referenced to tetramethylsilane (0.00 ppm). $^{13}C$ chemical shifts were referenced to $CDCl_3$ (77.0 ppm). IR spectra were recorded on a Perkin-Elmer 1760 infrared spectrometer (Shelton, Conn.). AI1 (Pearson et al., *Proc. Nat'l. Acad. Sci. USA* 91:197-201 (1994), which is hereby incorporated by reference in its entirety) and AI2 (Eberhard et al., *Arch. Microbiol.* 146:35-40 (1986), which is hereby incorporated by reference in its entirety) were synthesized according to literature procedures.

Synthesis of the Template Molecule: Ethyl 3-oxo-12-tridecenoate (1)

To a stirred solution of 10-undecenoic acid (5.055 mL, 25 mmol) in $CH_2Cl_2$ (50 mL) was slowly added $(COCl)_2$ (4.364 mL, 50 mmol). The mixture was stirred at room temperature overnight. The solvent was removed under reduced pressure to give 10-undecenoyl chloride (25 mmol). The product was used for the next reaction without further purification. $^1H$ NMR (500 MHz, $CDCl_3$) δ 1.29-1.48 (m, 10H), 1.71 (m, 2H), 2.05 (m, 2H), 2.88 (t, J=7 Hz, 2H), 4.98 (m, 2H), 5.80 (m, 1H).

A stirred solution of monoethyl malonate (5.3 g, 40 mmol) in anhydrous THF (150 mL) was cooled to −78° C. under an argon atmosphere, and n-BuLi (2.5 M, 32 mL, 80 mmol) was added drop-wise via an air-tight syringe. After the addition, the temperature was raised to 0° C., and the stirring was continued for 1 hour. The reaction mixture was then re-cooled to −78° C., and 10-undecenoyl chloride (25 mmol) was added drop-wise via an air-tight syringe. The mixture was stirred for one hour at −78° C., 30 minutes at 0° C., and 30 minutes at room temperature. The solvent was removed under reduced pressure, and the residue was re-dissolved in 50 mL ethyl acetate. The solution was washed with 1 M HCl (100 mL), saturated aqueous $NaHCO_3$ (50 mL), and brine (50 mL). The organic layer was dried over $MgSO_4$ and concentrated to give (1) (6.270 g). The crude product was used for the next reaction without further purification. $^1H$ NMR (400 MHz, $CDCl_3$) δ 1.28-1.40 (m, 13H), 1.58 (m, 2H), 2.03 (m, 2H), 2.53 (t, J=7 Hz, 2H), 3.43 (s, 2H), 4.21 (q, J=7 Hz, 2H), 4.97 (m, 2H), 5.80 (m, 1H).

Ethyl 3,3-ethylenedioxo-13-hydroxy-tridecanoate (2)

The mixture of (1) (6.270 g, ca. 24.7 mmol), ethylene glycol (13.67 mL, 247 mmol) and a catalytic amount of para-toluenesulfonic acid (p-TsOH) (475 mg, 2.5 mmol) in benzene (120 mL) was refluxed at 110° C. under an argon atmosphere overnight. The solvent was removed, and the residue was diluted with 50 mL ethyl acetate. The solution was washed with saturated aqueous $NaHCO_3$ (50 mL) and brine (50 mL), and the organic phase was dried ($MgSO_4$) and concentrated to give ethyl 3,3-ethylenedioxo-12-tridecenoate (6.973 g). The crude product was used for the next reaction without further purification. $^1H$ NMR (400 MHz, $CDCl_3$) δ 1.26-1.50 (m, 15H), 1.80 (m, 2H), 2.02 (m, 2H), 2.64 (s, 2H), 3.98 (m, 4H), 4.16 (q, J=7 Hz, 2H), 4.96 (m, 2H), 5.79 (m, 1H).

A stirred solution of ethyl 3,3-ethylenedioxo-12-tridecenoate (6.973 g, ca. 23.4 mmol) in anhydrous THF (100 mL) was cooled to 0° C. under an argon atmosphere. $BH_3$.THF (1 M, 117 mL, 117 mmol) was added drop-wise via an air-tight syringe. The mixture was stirred at 0° C. for three hours. Then, aqueous $NaHCO_3$ (2 M, 70 mL, 140 mmol) and 30% $H_2O_2$ (4.375 mL, 140 mmol) were added to the reaction slowly, and the mixture was stirred at room temperature for 1.5 hours. The organic solvent was evaporated under reduced pressure, and the residue was extracted with ethyl acetate (2×100 mL). The combined organic layers were washed with brine, then dried over $MgSO_4$ and concentrated. The residue was purified by flash chromatography (hexane/EtOAc 2:1, $R_f$=0.21) to give (2) (3.00 g, 9.5 nmol) as a colorless liquid. $^1H$ NMR (500 MHz, $CDCl_3$) δ 1.26-1.40 (m, 17H), 1.56 (m, 2H), 1.79 (m, 2H), 2.65 (s, 2H), 3.63 (t, J=7 Hz, 2H), 3.96 (m, 4H), 4.16 (q, J=7 Hz, 2H). The overall yield of the above three steps was 38%, and $^1H$ NMR data of all molecules were consistent with the literature data (Pearson et al., *Proc. Nat'l. Nat'l. Acad. Sci. USA* 91:197-201 (1994), which is hereby incorporated by reference in its entirety), except for the functionalities (olefin or hydroxyl group) newly introduced into the terminus of the acyl chain.

Solid Phase Reactions

DHP resin (0.98 mmol/g, 5.1 g, 5 mmol) was soaked in 50 mL $CH_2Cl_2$ for 1 hour. Then (2) (2.3 g, 7.28 mmol) and pyridium para-toluenesulfonate (PPTS) (1.83 g, 7.29 mmol) were added. The mixture was stirred gently at room temperature for 27 hours. The resin was washed with an excess amount of $CH_2Cl_2$ and dried under vacuum to give (3).

The mixture of (3) (ca. 5 mmol) and $LiOH.H_2O$ (21 g, 500 mmol) in 100 mL THF/$H_2O$ (1:1) was gently stirred and heated at 75° C. for 20 hours. The resin was sequentially washed with an excess amount of water, THF, and $CH_2Cl_2$ and dried under vacuum to give (4).

The parallel couplings of (4) with 96 molecules (FIG. 4) were performed on a 96 well reactor block by mixing the following compounds in each well: (4) (ca. 0.05 mmol), amine/alcohol (0.5 mmol), EDC (0.5 mmol), DMAP (0.5 mmol), iPr$_2$NEt (0.5 mmol), DMF (1.5 mL). The reactor block was assembled and rotated end-to-end at room temperature for 70 hours to afford coupling products (5).

Figure 8:
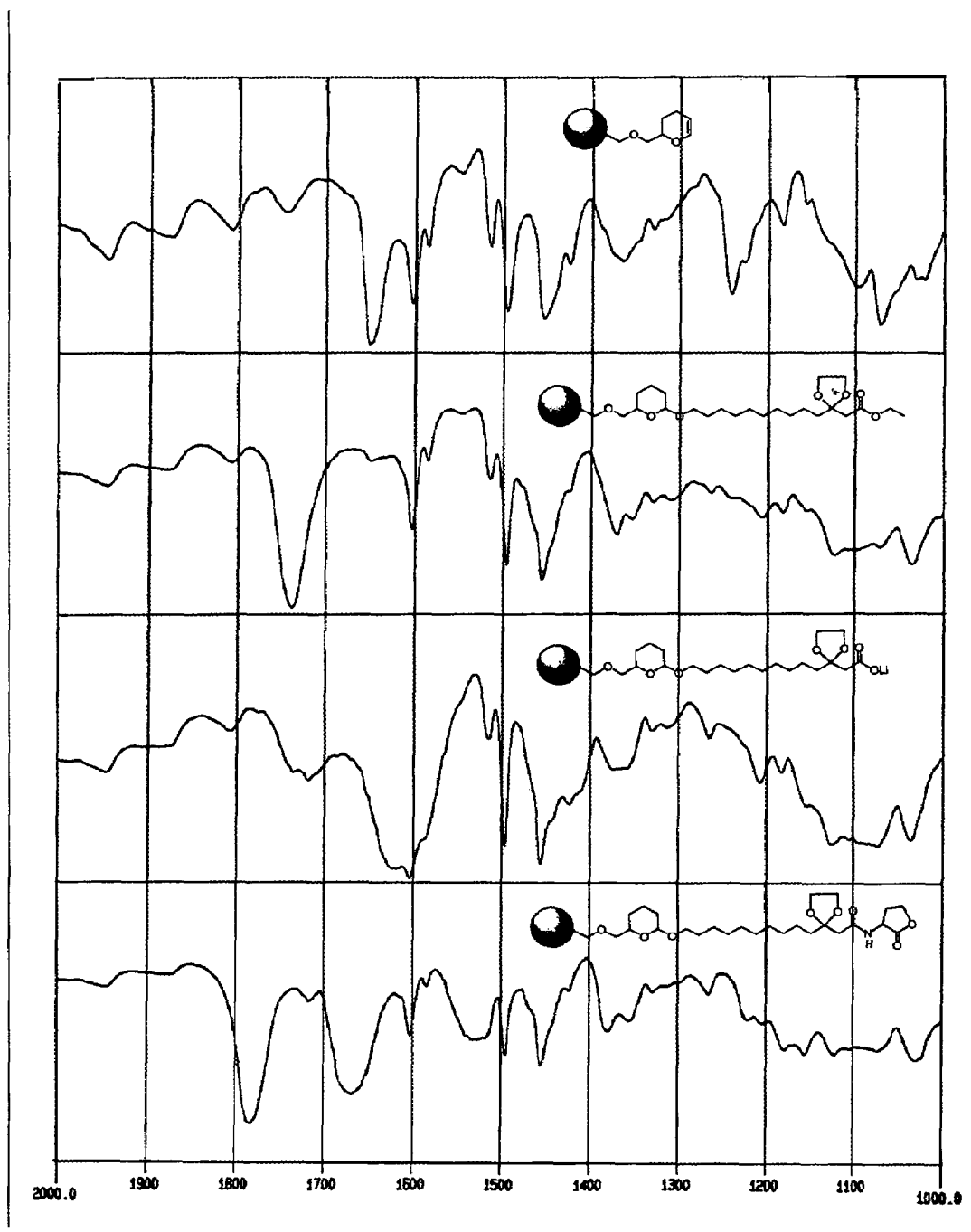
FIG. 8 shows representative on-resin FT-IR spectra of solid phase reactions. Only the region between 1000 $cm^{-1}$ and 2000 $cm^{-1}$ is shown here.

DHP resin, the intermediates (3) and (4), and some representative coupling products (5a-d) were characterized by on-resin FT-IR (FIG. 8). In each case, a small amount of dried resin (1-2 mg) was mixed with anhydrous KBr (75 mg) to make a pellet, and FT-IR spectroscopy was recorded.

DHP resin. IR (KBr) 3020, 2890, 1644, 1491, 1446, 1237, 1060, 746, 662 cm$^{-1}$.

(Resin bound) Ethyl 3,3-ethylenedioxo-13-(tetrahydropyranyl)oxytridecanoate (3). IR (KBr) 3459, 3026, 2931, 1734, 1494, 1455, 1029, 758, 698 cm$^{-1}$.

(Resin bound) Lithium 3,3-ethylenedioxo-13-(tetrahydropyranyl)oxytridecanoate (4). IR (KBr) 3437, 3025, 2927, 1603, 1494, 1454, 1073, 759, 699 cm$^{-1}$.

(Resin bound) N-(13-tetrahydropyranyloxy-3,3-ethylenedioxo-tridecanoyl)-L-homoserine lactone (5a). IR (KBr) 3372, 3026, 2920, 1784, 1673, 1494, 1454, 1028, 756, 698 cm$^{-1}$.

(Resin bound) 2-(13-tetrahydropyranyloxy-3,3-ethylenedioxo-tridecanoyl)-1,3,4-thiadiazole (5b). IR (KBr) 3450, 3025, 2920, 1697, 1549, 1494, 1454, 1032, 757, 698 cm$^{-1}$.

(Resin bound) 2-(13-tetrahydropyranyloxy-3,3-ethylenedioxo-tridecanoyl)-phenol (5c). IR (KBr) 3366, 3025, 2930, 1682, 1533, 1494, 1454, 1031, 749, 697 cm$^{-1}$.

(Resin bound) 3-(13-tetrahydropyranyloxy-3,3-ethylenedioxo-tridecanoyl)-2,6-dimethoxypyridine (5d). IR (KBr) 3356, 3026, 2927, 1685, 1592, 1521, 1455, 1021, 757, 698 cm$^{-1}$.

After the coupling reaction, the reactor block was disassembled and connected to a vacuum line. The resin was washed with a large amount of DMF and CH$_2$Cl$_2$ to remove excessive reactants, coupling reagents, and undesired byproducts. The vacuum was applied overnight to dry the resin. 1 mL TFA/H$_2$O (95:5) was added into each well, and the reactor block was reassembled and rotated at room temperature for 30 minutes. The cleavage products (6) were collected into a 96 deep-well plate. 1 mL CH$_2$Cl$_2$ was added to each resin to wash off the products into the collection plate. The solvents were evaporated with a water pump, and the products were dried under vacuum. Four products (6a-d, see below) were arbitrarily chosen and characterized by $^1$H NMR and FAB mass spectrometry to confirm the formation of the desired product.

N-(13-trifluoroacetoxy-3-oxo-tridecanoyl)-L-homoserine lactone (6a). 9.9 mg was obtained in 51% yield. $^1$H NMR (500 MHz, CDCl$_3$) δ 7.66 (d, J=5 Hz, 1H), 4.6 (m, 1H), 4.48 (t, J=8 Hz, 1H), 4.35 (t, J=7 Hz, 1H), 4.28 (m, 1H), 3.47 (s, 2H), 2.77 (m, 1H), 2.53 (t, J=7 Hz, 2H), 2.23 (m, 1H), 1.76 (m, 2H), 1.58 (m, 2H), 1.20-1.40 (broad, 12H); FAB-LRMS calc'd for C$_{19}$H$_{29}$NO$_6$F$_3$ (MH$^+$) 424.2. found 424.5.

2-(13-trifluoroacetoxy-3-oxo-tridecanamido)-1,3,4-thiadiazole (6b). 13.1 mg was obtained in 67% yield. $^1$H NMR (500 MHz, CDCl$_3$) δ 12.76 (s, 1H), 8.82 (s, 1H), 4.33 (t, J=7 Hz, 2H), 3.87 (s, 2H), 2.63 (t, J=7 Hz, 2H), 1.50-1.80 (m, 4H), 1.18-1.22 (broad, 12H); FAB-LRMS calc'd for C$_{17}$H$_{25}$N$_3$O$_4$SF$_3$ (MH$^+$) 424.1. found 424.4.

2-(13-trifluoroacetoxy-3-oxo-tridecanamido)-phenol (6c). 10.4 mg was obtained in 52% yield. $^1$H NMR (500 MHz, CDCl$_3$) δ 9.82 (s, 1H), 8.68 (s, 1H), 7.15 (m, 1H), 7.04 (m, 2H), 6.89 (m, 1H), 4.34 (t, J=7 Hz, 2H), 3.64 (s, 2H), 2.42 (t, J=7 Hz, 2H), 1.76 (m, 2H), 1.56 (m, 2H), 1.20-1.40 (broad, 12H); FAB-LRMS calc'd for C$_{21}$H$_{29}$NO$_5$F$_3$ (MH$^+$) 432.2. found 432.4.

3-(13-trifluoroacetoxy-3-oxo-tridecanamido)-2,6-dimethoxypyridine (6d). 10.8 mg was obtained in 49% yield. $^1$H NMR (500 MHz, CDCl$_3$) δ 9.05 (s, 1H), 8.43 (d, J=8 Hz, 1H), 6.29 (d, J=8 Hz, 1H), 4.34 (t, J=7 Hz, 2H), 4.03 (s, 3H), 3.89 (s, 3H), 3.56 (s, 2H), 2.58 (t, J=7 Hz, 2H), 1.74 (m, 2H), 1.59 (m, 2H), 1.20-1.40 (broad, 12H); FAB-LRMS calc'd for C$_{22}$H$_{32}$N$_2$O$_6$F$_3$ (MH$^+$) 477.2. found 477.3.

Synthesis of 3-oxo-C$_{12}$-HSL and 3-oxo-C$_{12}$-D12
3,3-ethylenedioxydodecanoic Acid A stirred solution of monoethyl malonate (1.26 g, 9.6 mmol) in 25 mL anhydrous THF was cooled to −78° C. under an argon atmosphere, and n-BuLi (2.5 M, 8 mL, 20 mmol) was added drop-wise via an air-tight syringe. After the addition, the temperature was raised to 0° C., and the stirring was continued for 1 hour. The mixture was then re-cooled to −78° C., and decanoyl chloride (1.044 mL, 5 mmol) was added drop-wise via an air-tight syringe. The mixture was stirred for one hour at −78° C., 30 minutes at 0° C. and 30 minutes at room temperature. The solvent was removed under reduced pressure, and the residue was re-dissolved in 50 mL ethyl acetate. The solution was washed with 1 M HCl (100 mL), saturated aqueous NaHCO$_3$ (50 mL), and brine (50 mL). The organic layer was dried over MgSO$_4$ and concentrated to give ethyl 3-oxododecanoate (1.456 g). The crude product was used for the next reaction. $^1$H NMR (500 MHz, CDCl$_3$) δ 0.88 (t, J=7 Hz, 3H), 1.20-1.38 (m, 12H), 1.50-1.68 (m, 2H), 2.53 (t, J=7.5 Hz, 2H), 3.43 (s, 2H), 4.20 (q, J=7 Hz, 2H); $^{13}$C NMR (125 MHz, CDCl$_3$) δ 13.975, 13.988, 22.5, 23.4, 28.91, 29.14, 29.26, 29.29, 31.8, 42.9, 49.2, 61.2, 167.2, 202.9.

The mixture of ethyl 3-oxododecanoate (1.456 g, ca. 5 mmol), ethylene glycol (2.78 mL, 50 mmol) and a catalytic amount of p-TsOH (95 mg, 0.5 mmol) in benzene (50 mL) was heated to 110° C. under an argon atmosphere overnight. The solvent was removed, and the residue was diluted with 50 mL ethyl acetate. The solution was washed with saturated aqueous NaHCO$_3$ (50 mL) and brine (50 mL), and the organic phase was dried over MgSO$_4$ and concentrated. The residue was purified by flash chromatography (hexane/EtOAc 8:1, R$_f$=0.21) to give ethyl 3,3-ethylenedioxydodecanoate (1.131 g, 3.95 mmol) in 79% overall yield for the above two steps. $^1$H NMR (500 MHz, CDCl$_3$) δ 0.88 (t, J=7 Hz, 3H), 1.20-1.44 (m, 17H), 1.76-1.82 (m, 2H), 2.65 (s, 2H), 3.94-4.04 (m, 4H), 4.16 (q, J=7 Hz, 2H); $^{13}$C NMR (125 MHz, CDCl$_3$) δ 14.1, 22.6, 23.4, 29.22, 29.43, 29.48, 29.62, 31.8, 37.7, 42.5, 60.4, 65.0, 109.4, 169.5.

To a 25 mL flask were added ethyl 3,3-ethylenedioxydodecanoate (1.131 g, 3.95 mmol), LiOH.H$_2$O (840 mg, 20 mmol), THF (5 mL), and water (5 mL). The mixture was stirred at room temperature overnight. The solution was acidified by the addition of 1 M HCl (50 mL), and extracted with ethyl acetate (3×50 mL). The organic layers were combined and washed once with brine. The organic phase was dried (MgSO$_4$) and concentrated to give 3,3-ethylenedioxydodecanoic acid (0.824 g, 3.19 mmol) in 81% yield. $^1$H NMR (500 MHz, CDCl$_3$) δ 0.88 (t, J=7 Hz, 3H), 1.20-1.44 (m, 14H), 1.72-1.80 (m, 2H), 2.72 (s, 2H), 3.98-4.10 (m, 4H); $^{13}$C NMR (125 MHz, CDCl$_3$) δ 13.9, 22.5, 23.3, 29.13, 29.35, 29.39, 29.50, 31.7, 37.5, 42.2, 64.9 (2 C), 109.2, 174.8.

All data above are consistent with the literature data reported previously (Wierenga et al., *J. Org. Chem.* 44:310-

311 (1979); Eberhard et al., *J. Biochem.* 20:2444-2449 (1981), which are hereby incorporated by reference in their entirety).

N-(3-oxododecanoyl)-L-homoserine lactone (3-oxo-$C_{12}$-HSL, AI-1)

To a 25 mL flask were added 3,3-ethylenedioxydodecanoic acid (824 mg, 3.2 mmol), L-homoserine lactone hydrobromide (1.135 g, 6.2 mmol), EDC (1.198 g, 6.2 mmol), DMAP (0.756 g, 6.2 mmol), i-Pr$_2$NEt (1.1 mL, 6.3 mmol) and DMF (5 mL). The reaction was stirred at room temperature overnight. DMF was removed under reduced pressure, and the residue was re-dissolved into 1 M HCl (25 mL). The aqueous solution was extracted with ethyl acetate (3×25 mL), and the combined extracts were washed sequentially with saturated aqueous NaHCO$_3$ and brine. The organic phase was dried (MgSO$_4$) and concentrated to give approximately 1 g crude intermediate.

The above intermediate (1 g, ca. 2.93 mmol) was dissolved in acetone (48 mL) and water (4 mL), and p-TsOH (0.285 g, 1.5 mmol) was added. The mixture was refluxed at 65° C. for 20 hours. The acetone was removed under reduced pressure, and the residue was dissolved into 25 mL ethyl acetate. The organic layer was washed sequentially with saturated aqueous NaHCO$_3$ and brine, then dried (MgSO$_4$) and concentrated to give the pure product (741 mg, 2.49 mmol) in 86% yield. IR(KBr) 3295, 2921, 1782, 1712, 1642, 1549, 1179, 1017 cm$^{-1}$; $^1$H NMR (CDCl$_3$, 500 MHz) δ 0.88 (t, J=7.2 Hz, 3H), 1.20-1.38 (broad, 12H), 1.50-1.65 (m, 2H), 2.20-2.30 (m, 1H), 2.54 (t, J=7.2 Hz, 2H), 2.72-2.84 (m, 1H), 3.47 (s, 2H), 4.24-4.32 (m, 1H), 4.48 (t, J=9.2 Hz, 1H), 4.58-4.64 (m, 1H), 7.67 (d, J=5.2 Hz, 1H); $^{13}$C NMR (125 MHz, CDCl$_3$) δ 14.0, 22.5, 23.4, 28.89, 29.14, 29.26, 29.29, 29.43, 31.7, 43.7, 28.4, 48.9, 65.9, 166.5, 175.0, 206.3; EI-HRMS calc'd for $C_{16}H_{27}O_4N$ (M$^+$) 297.1935. found 297.1940.

N-(trans-2-hydroxycyclohexyl)-3-oxododecanamide (3-oxo-$C_{12}$-HSL-D12)

The same procedure for the preparation of AI-1 was used. 38 mg crude product was obtained from trans-2-aminocyclohexanol hydrochloride. Flash chromatography (EtOAc) gave 3-oxo-$C_{12}$-HSL-D12 in the ketone form (23 mg, 0.074 mmol, R$_f$=0.29) and enol form (11 mg, 0.035 mmol, R$_f$=0.17). Ketone form: IR (KBr) 3274, 2927, 1715, 1652, 1617, 1564 cm$^{-1}$; $^1$H NMR (500 MHz, CDCl$_3$) δ 0.88 (t, J=7.5 Hz, 3H), 1.18-1.40 (m, 16H), 1.58 (m, 2H), 1.72 (m, 2H), 1.90-2.10 (m, 2H), 2.53 (t, J=7.5, 2H), 3.35 (m, 1H), 3.43 (s, 2H), 3.67 (m, 1H), 7.19 (d, J=5 Hz, 1H); $^{13}$C NMR (125 MHz, CDCl$_3$) δ 14.1, 22.6, 23.3, 23.9, 24.5, 28.9, 29.21, 29.31, 29.34, 31.2, 31.8, 34.2, 44.0, 48.3, 55.7, 75.2, 167.3, 207.5; EI-HRMS calc'd for $C_{18}H_{33}O_3N$ (M$^+$) 311.2455. found 311.2463. Enol form: IR (KBr) 2921, 2853, 1668, 1452, 1040 cm$^{-1}$; $^1$H NMR (500 MHz, CDCl$_3$) δ 0.88 (t, J=7.5 Hz, 3H), 1.16-1.60 (m, 18H), 1.75 (m, 2H), 2.00-2.24 (m 4H), 3.25 (m, 1H), 3.84 (m, 1H), 5.02 (d, J=2 Hz), 5.60 (s, 1H); $^{13}$C NMR (125 MHz, CDCl$_3$) δ 14.1, 22.7, 23.2, 23.4, 27.3, 28.9, 29.27, 29.33, 29.44, 31.5, 31.9, 32.2, 36.8, 54.2, 82.7, 97.4, 166.1, 167.8; EI-HRMS calc'd for $C_{18}H_{31}O_2N$ (M-H$_2$O) 293.2349. found 293.2357.

Example 2—Library Screening for Agonists

Screening of individual molecules for their ability to activate LasR was conducted using *P. aeruginosa* PAO-JP2 (lasI, rhlI) harboring plasmid plasI-LVAgfp (a gift from Dr. Barbara Iglewski at the University of Rochester) (de Kievit et al., *Appl. Environ. Microbiol.* 67:865-1873 (2001), which is hereby incorporated by reference in its entirety). Since this strain lacks the ability to produce natural AIs due to disruption of both AI synthase genes, activation of LasR relies on the addition of exogenous AI1. Expression of gfp (encoding green fluorescent protein) is under control of the LasR-AI1 inducible lasI promoter, allowing rapid screening for LasR agonists by measuring the level of GFP expression in their presence.

GFP Reporter Assays

The procedure of screening and biological assay was similar to that reported by Kline et al. (Kline et al., *Bioorganic & Medicinal Chemistry Letters,* 9:3447-3452 (1999), which is hereby incorporated by reference in its entirety) and the representative process is described here. *P. aeruginosa* strain PAO-JP2 (lasI, rhlI) (Rahme et al., *Science* 268:1899-1902 (1995), which is hereby incorporated by reference in its entirety) harboring plasI-LVAgfp (Pearson et al., *Proc. Natl Acad. Sci. USA* 91:197-201 (1994), which is hereby incorporated by reference in its entirety) was grown at 37° C. in LB with 300 µg/ml carbenicillin. For agonist assays, an overnight culture was diluted to an OD$_{600}$ of 0.1 and transferred to wells of a 96-well plate on which test compounds had previously been added and dried. The final concentration of each analog tested was roughly 400 µM, although this is an overestimate due to purity issues. Cells were then incubated for 6 hours at 37° C. with vigorous shaking. GFP expression was detected with a Molecular Imager (BioRad) (488 nm excitation and 695 nm bandpass filter) and quantified with ImageQuant software. The OD$_{600}$ of cultures was determined to normalize GFP expression to cell density.

lacZ Reporter Assays

*E. coli* strain MG4 (pKDT37) was grown overnight in Supplemented A media with 100 µg/mL ampicillin at 30° C. and diluted 1:100 in the same media. 1 mL of this culture was added to a test tube containing AI1 or 3-oxo-$C_{12}$-D12 that had been previously aliquoted and dried. Following a 6 hour incubation at 30° C., β-galactosidase activity was determined using standard methods (Platt et al., *Assays of the lac operon Enzymes In: Experiments in Molecular Genetics*, Cold Spring Harbor Laboratory Press, Cold Spring Harbor, N.Y., pp. 352-355 (1972), which is hereby incorporated by reference in its entirety).

Results

Figure 5:
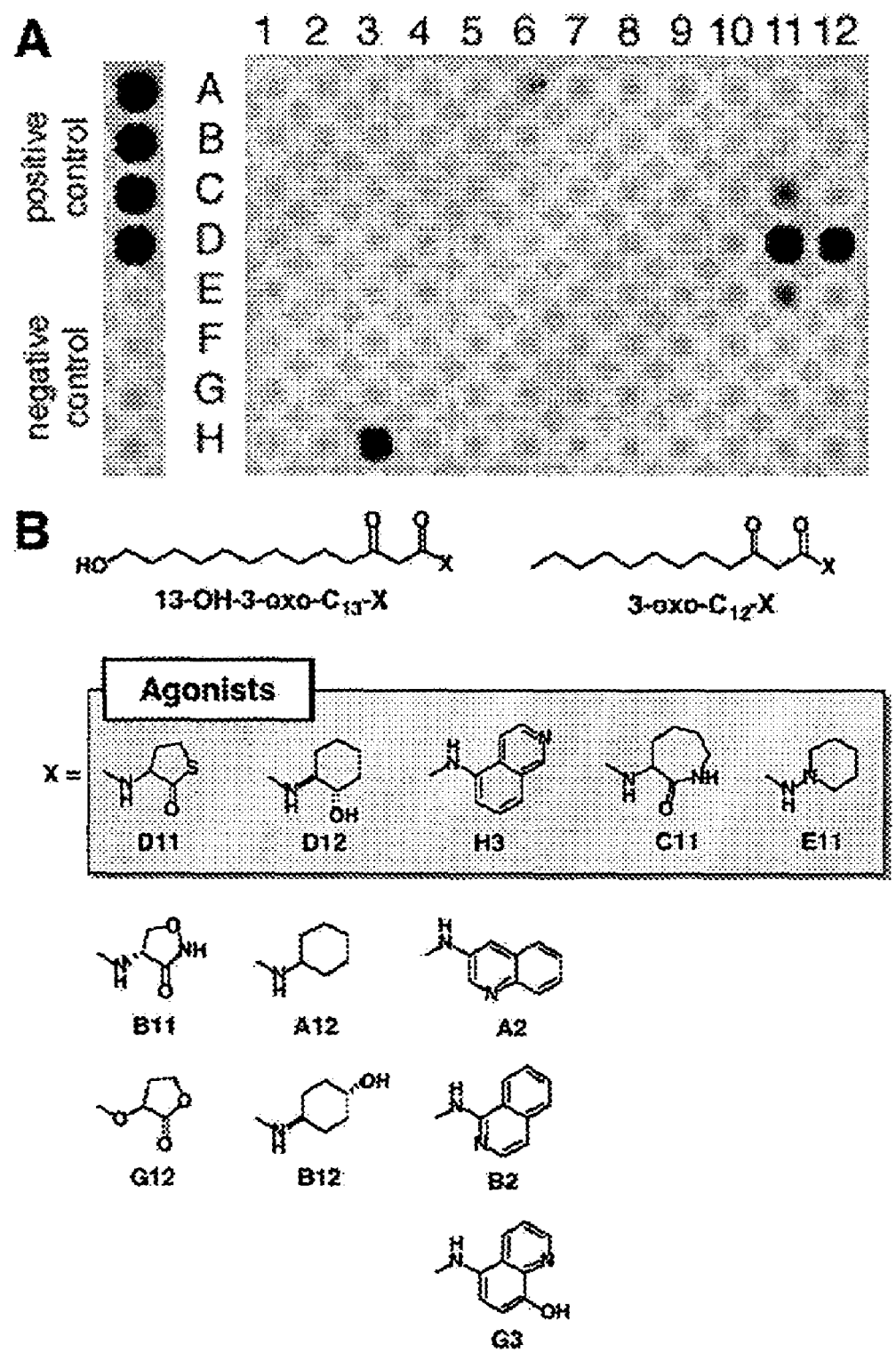
FIGS. 5A-B show agonist screening.

Results of screening are shown in FIG. 5. Three strong agonists (D11, D12, H3) and two weaker agonists (C11, E1) were present in the library. The corresponding unconjugated amines were assayed and no agonist activity was observed, indicating the side chain is crucial for activity. Among the three strong agonists identified is homocysteine thiolactone (D11), which was included in the library as an internal control. This confirmed the reliability of the assay system as well as the assumption that the OH modification at the terminus of the acyl side chain does not interfere with agonist activity. Interestingly, B11 and G12, compounds very similar to D11, were not active. B11 is likely inactive due to the γ-lactam ring structure (which is known to be nearly inactive (Passador et al., *J. Bacteriol.* 178:5995-6000 (1996), which is hereby incorporated by reference in its entirety)) and interference of the oxygen substitution with hydrophobic interactions between the inducer and LasR. G12, which has the HSL amide bond replaced with an ester, is also inactive. This indicates that the amino group is required for activity in *P. aeruginosa*. This data is supported by the recent TraR-3-oxo- $C_8$-HSL crystal structure that shows Asp70 (a residue conserved in LasR) in a hydrogen (H) bond with the HSL amino group. This putative H bond cannot be maintained by compound G12.

Figure 9:
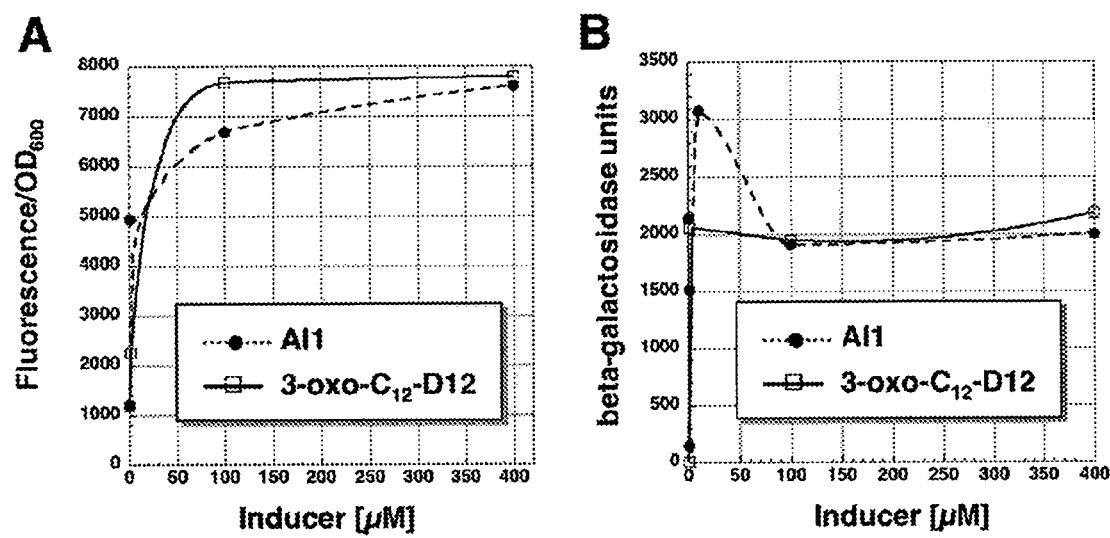
FIGS. 9A-B show reporter gene assays.

One of the new agonist structures identified from the library, D12, is 2-aminocyclohexanol (FIG. 5B). The hydroxyl group adjacent to the amino group in D12 is clearly important for activity, since similar molecules that lack the OH group at this position, such as compounds A12 and B12, showed no activity. Interestingly, D12 shares two structural features with AI1: (1) the OH group mimics the carbonyl group of HSL which participates in a hydrogen bond in the TraR crystal structure, with the highly conserved residue Trp57; and (2) the cyclohexane ring mimics the saturated ring structure of HSL, presumably presenting appropriate hydrophobic contacts to LasR. 3-oxo-$C_{12}$-D12, containing the natural side chain, was synthesized in solution phase, and tested with both the lasI-gfp reporter as well as a lasB-lacZ reporter in *Escherichia coli*. *E. coli* strain MG4 harboring plasmid pKDT37 expresses lasR and contains a lacZ reporter gene controlled by a LasR-AI1 inducible lasB promoter (Passador et al., *J. Bacteriol.* 178:5995-6000 (1996), which is hereby incorporated by reference in its entirety). Both of these reporter genes were activated in the presence of control AI1 or 3-oxo-$C_{12}$-D12 (FIG. 9), demonstrating that this agonist has LasR inducing activity comparable to the natural AI1. It also provides strong evidence that the agonist activity in *P. aeruginosa* is LasR dependent.

The second strong agonist, H3 (FIG. 5A), is a quinoline derivative (FIG. 5B). Comparison of H3 with other quinoline derivatives in the library such as A2, B2, and G3, suggests that the positions of N2 and the 5-exo-amine on the quinoline ring dictate activity. Since H3 shares some structural features with another autoinducer called Pseudomonas quinolone signal (PQS, FIG. 1) it appears that it may exert its agonist activity via the PQS pathway. PQS has been shown to strongly induce rhlI, and mildly induce both lasR and rhlR, but not lasI (Pesci et al., *Proc. Natl Acad. Sci. USA* 96:11229-11234 (1999), which is hereby incorporated by reference in its entirety). However, these studies were done in a lasR null background and might be drastically different in the presence of LasR. A PQS analog discovered in experiments activated the lasI-gfp reporter in strain PAO-JP2 (plasI-LVAgfp), suggesting that PQS may be able to induce the lasI promoter in the presence of LasR. Other protein(s) involved in PQS signaling have not yet been identified. Two weaker agonists, C11 and E11, were also identified. Although both compounds exhibited detectable levels of agonist activity, their activities were significantly lower than the other three agonists found in the library. It should be noted that 3-oxo-$C_6$-C11 was not active in *V. fischeri* reporter gene assays (Schaefer et al., *J. Bacteriol.* 178:2897-2901 (1996), which is hereby incorporated by reference in its entirety).

Example 3—Library Screening for Antagonists

Each compound in the library was tested for antagonist activity using the same reporter strain, PAO-JP2 (plasI-LVAgfp) (de Kievit et al., *Appl. Environ. Microbiol.* 67:865-1873 (2001), which is hereby incorporated by reference in its entirety) to find compounds that could compete against AI1 and reduce GFP expression. The methods were the same as described in Example 2 (GFP Reporter Assay), except that 1 µM AI1 was added to each well in combination with the library compound. The fluorescence/OD$_{600}$ of each compound competing against AI1 was reported relative to the fluorescence/OD$_{600}$ of the positive control of AI1 alone, which was set to 1. When strain PAO-JP2 (prhlI-LVAgfp) was used, the positive control was 1 µM AI1 and 10 µM AI2. Eight compounds that inhibited reporter gene expression by greater than 50% were identified (see, e.g., FIG. 6).

Among these antagonists, D10, H10, C10, F10 and G9 are aniline derivatives. This set of molecules also has an ortho- or meta-substituent of a hydroxyl, carboxyamide, or pyridyl group, which can act as H bond acceptors. The position of these substituents seems important, and depends on the particular substituent, i.e., ortho for hydroxyl or pyridyl and ortho/meta for carboxyamide. Structurally similar compounds differing only in the position of these substituents, E10 and G10 (FIG. 6), were inactive. This indicates that the hydroxyl group in D10 and H10, the pyridyl group in G9, and the carbonyl group in C10 and F10 maintain the putative H bond interaction observed between TraR Trp57 and the *A. tumefaciens* AI1 (Zhang et al., *Nature* 417:971-974 (2002), which is hereby incorporated by reference in its entirety) by acting as H bond acceptors. The importance of the putative H bond is consistent with the observation that agonists D11, D12, C11, and E11 (FIG. 5B) all have a potential H bond acceptor group adjacent to the amino group. It was concluded, therefore, that the combination of an aniline structure and H bond acceptor dictates the antagonist activity of this set of molecules.

Figure 10:
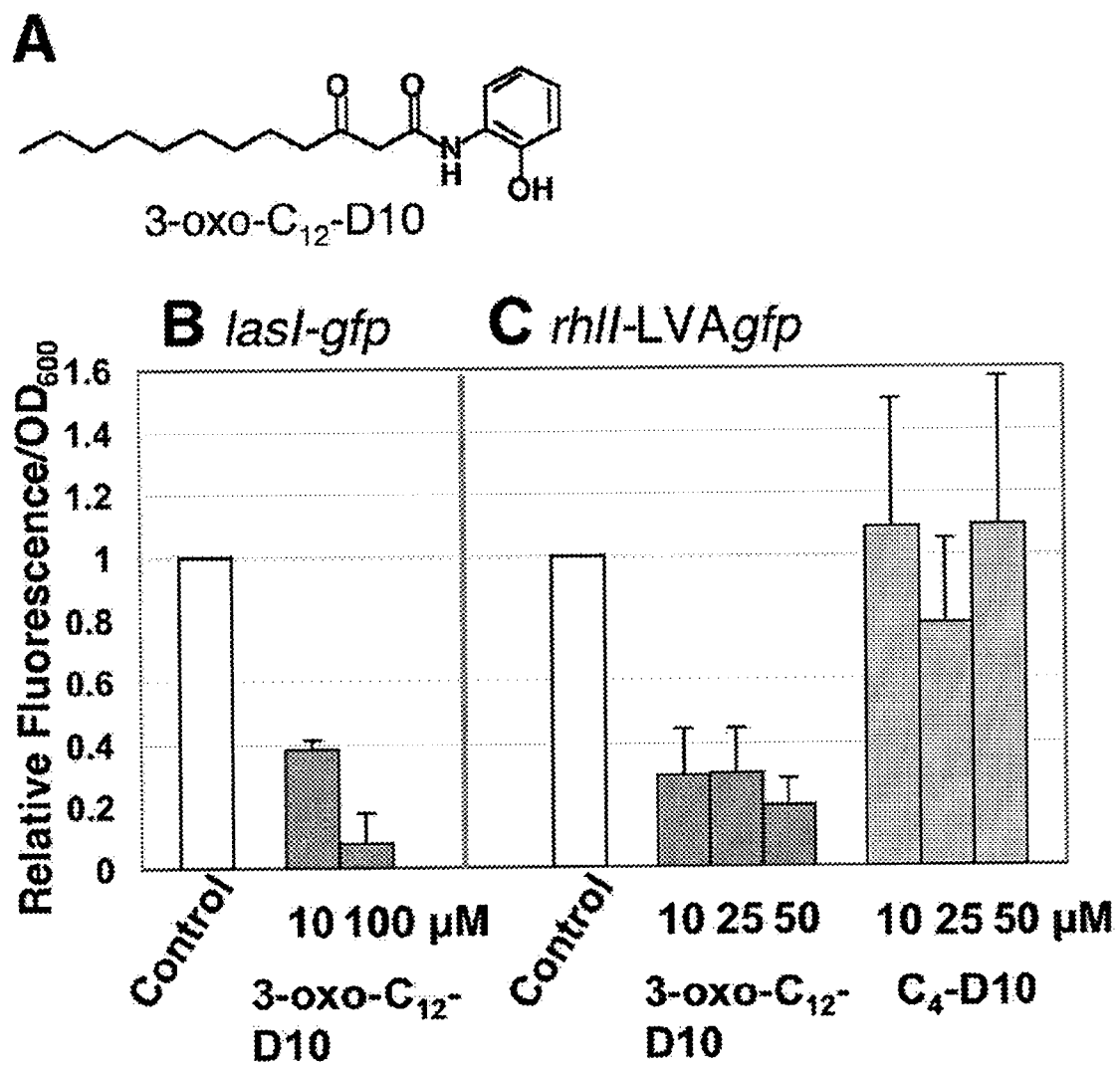
FIGS. 10A-C show the chemical structure of an antagonist and antagonist assays.

Example 4—3-oxo-$C_{12}$-(2-aminophenol) and $C_4$-(2-amino-phenol) Analysis Since D10 (2-aminophenol) was the simplest molecule among the aniline-based antagonists, and most interestingly it differed from the strong agonist D12 only by the unsaturated ring, D10 was used for further studies. 3-oxo-$C_{12}$-$D_{10}$ was synthesized in solution phase, where the natural side chain was coupled with D10 and purified by chromatography. To determine if the same structural motif can be applied to inhibition of the RhlR-AI2 interaction, $C_4$-D10 was also synthesized. Assays were performed with both the lasI-gfp reporter PAO-JP2 (plasI-LVAgfp) and an RhlR-AI2 controlled rhlI-gfp reporter, PAO-JP2 (prhlI-LVAgfp) (FIGS. 10A-C) (de Kievit et al., *Appl. Environ. Microbiol.* 67:865-1873 (2001), which is hereby incorporated by reference in its entirety). The lasI-gfp reporter assay clearly showed a concentration dependent inhibition of GFP expression by 1 µM 3-oxo-$C_{12}$-D10, resulting in approximately 60 and 90% reduction of GFP expression by the addition of 10 and 100 µM 3-oxo-$C_{12}$-D10, respectively (FIG. 10B). A strong reduction of GFP expression by 3-oxo-$C_{12}$-D10 was also observed with the rhlI-gfp reporter (FIG. 10C). The expression induced by 1 µM AI1 and 10 µM AI2 was inhibited by more than 80% in the presence of 50 µM 3-oxo-$C_{12}$-D10. These results suggested that 3-oxo-$C_{12}$-D10 is a strong and specific inhibitor of QS, so assays of specific QS controlled virulence factors were pursued, as discussed below. $C_4$-D10 did not inhibit rhlI-gfp expression, indicating that $C_4$-D10 does not antagonize the RhlR-AI2 interaction (FIG. 10C). This compound was also tested in virulence factor assays, but consistently showed no effect on their expression.

Figure 11:
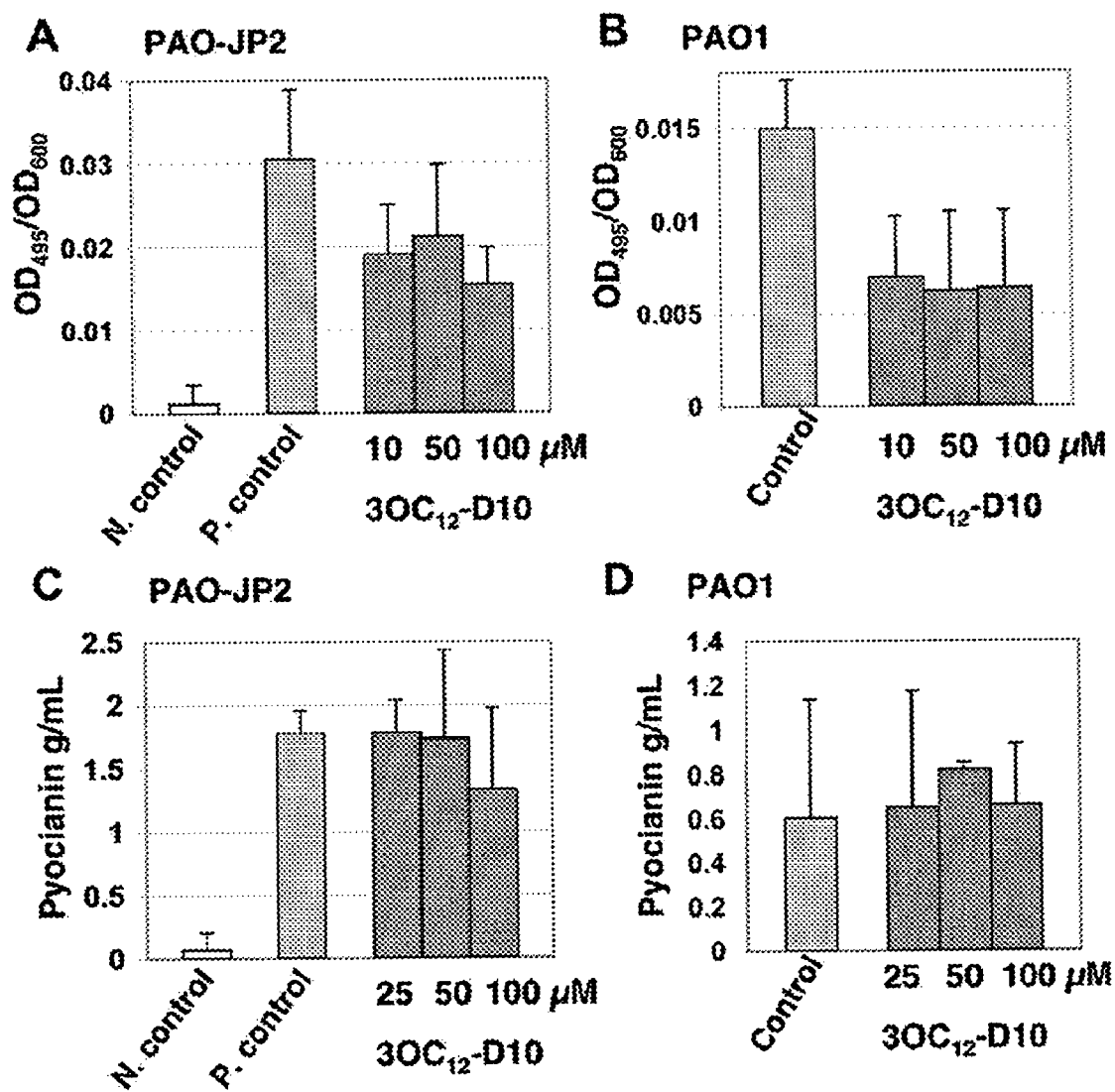
FIGS. 11A-D show virulence factor assays.

To further confirm the ability of 3-oxo-$C_{12}$-D10 to specifically interfere with QS controlled gene expression, its ability to reduce expression of elastase, pyocyanin, and biofilm, three *P. aeruginosa* virulence factors controlled by QS, was tested (de Kievit et al., *Sci. Med. November/December:*42-50 (1999), which is hereby incorporated by reference in its entirety). Pyocyanin, elastase, and biofilm were assayed as previously described (Smith et al., *Chem. Biol.* 10:81-89 (2003), which is hereby incorporated by reference in its entirety). Elastase activity produced by *P. aeruginosa* in the presence of AIs and competing 3-oxo-$C_{12}$-D10 was determined by measuring breakdown of the substrate Elastin Congo Red. Using the lasI rhlI knockout strain PAO-JP2, 10-100 µM 3-oxo-$C_{12}$-D10 reduced elastase activity by approximately 50% when competing against 5 µM AI and 10 µM AI2 supplied exogenously (FIG. 1A). This antagonist also reduced elastase activity produced by wild type *P. aeruginosa* strain PAO1 (FIG. 11B). These results indicate that 3-oxo-$C_{12}$-D10 inhibits elastase production by *P. aeruginosa*, and provides additional evidence that this compound specifically interferes with las QS-controlled gene expression.

Further testing of 3-oxo-$C_{12}$-D10 for its effect on pyocyanin production is presented in FIGS. 11C and D. This compound was not able to interfere with pyocyanin production by either PAO-JP2 (FIG. 11C) or PAO1 (FIG. 11D). This indicates that it is necessary to interfere with both LasR and RhlR function in order to significantly inhibit pyocyanin production.

Figure 12:
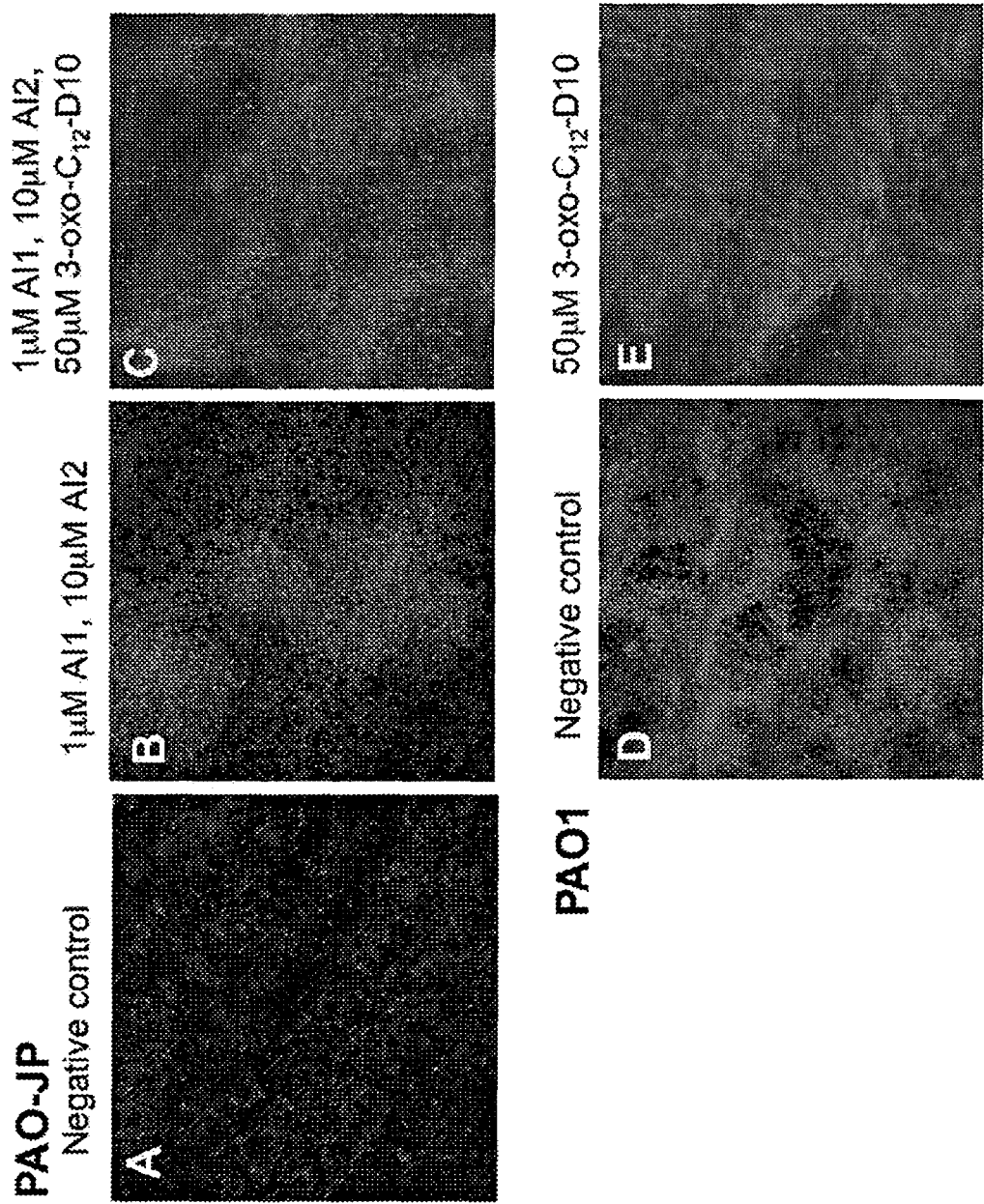
FIGS. 12A-E show static biofilm assays.

Static biofilm assays were also performed with 3-oxo-$C_{12}$-D10 (FIGS. 12A-E). In POA-JP2, formation of biofilm was dependent on the presence of exogenous AIs (FIGS. 12A and B). When 3-oxo-$C_{12}$-D10 was added to PAO-JP2 in combination with AIs (FIG. 12C), biofilm formation was slightly enhanced rather than inhibited. Similarly, 3-oxo-$C_{12}$-D10 did not interfere with biofilm formation by wild type PAO1 cells (FIGS. 12D and E). However, the molecule clearly had an effect on biofilm morphology, resulting in a biofilm that appeared "fluffy". Therefore, although inhibition of biofilm formation was not observed, the molecule had some impact on biofilm architecture.

Example 5—Discussion

An efficient synthetic sequence to generate a library of AI1 analogs has been developed. Additional analog libraries can be easily and rapidly synthesized and screened for activity, based on the above description. Screening of the initial library identified new agonists that follow the same trend as previously discovered structures, allowing the conclusion that the HSL keto group and saturated carbons on the ring are involved in the interaction between the inducer and LasR. This result is consistent with the X-ray structure of a LasR homolog, TraR, that identified an H bond interaction between TraR and the HSL oxo group (Zhang et al., *Nature* 417:971-974 (20002); Vannini et al., *EMBO J.* 21:4393-4401 (2002), which are hereby incorporated by reference in their entirety). Several new antagonists of the QS system were also identified. It has been shown that a common structural feature for antagonists is an aniline ring with an appropriate H bond acceptor at the ortho or meta position. It is striking that the only difference between the agonist 3-oxo-$C_{12}$-D12 (2- aminocyclohexanol) and the antagonist 3-oxo-$C_{12}$-$D_{10}$ (2-aminophenol) is an aromatic ring. It appears that an aromatic ring somehow interferes with the ability of the antagonists to activate the R protein for DNA binding.

The antagonist 3-oxo-$C_{12}$-D10 displays potent inhibitory activity in reporter gene assays and interferes with elastase activity and normal bio film formation. The promoter-specific differences in inhibitory activity result from the complexity of the *P. aeruginosa* QS signaling network.

The potential benefits of controlling QS are very significant both medically and economically. The parallel synthesis of AI analogs allowing discovery of several new analogs that activate or inhibit QS provides a significant advancement in the understanding of the LasR-AI1 interaction. This results in alternative therapeutic options for the treatment of chronic *P. aeruginosa* and other bacterial infections.

Example 6—Antagonists Found from a Focused Library Based on the Agonists

A library of *P. aeruginosa* autoinducer analogs with variation targeted to the homoserine lactone (HSL) moiety was synthesized (see Examples 1-5) and a new agonist, 3-oxo-$C_{12}$-(2-aminocyclohexanol), capable of activating LasR as a transcription factor was discovered. Two sets of focused libraries against the quorum sensing transcription factors LasR and RhlR, respectively, were constructed. Opposing the prediction that both proteins should have the same binding site for HSL, it was determined that these two related proteins respond to different structural motifs. This suggested that the HSL binding site differs in these proteins. Subtle structural modifications to the agonists yielded compounds with antagonist activity. A series of assays was performed to show that inhibition of quorum sensing by these antagonists significantly reduced the production of virulence factors and biofilm formation.

A new structural element at the HSL position, 2-aminocyclohexanol, was found that exhibits a nearly wild type QS activity (Examples 1-4). Superimposition of the amino and hydroxyl groups in this molecule with the amino and keto groups in HSL suggested similarities in structure. Thus, it was hypothesized that a 5- or 6-membered ring with a keto or hydroxyl group (or other hydrogen bond acceptor) adjacent to the amine is sufficient for both binding and activation of LasR. To test this hypothesis, the series of molecules shown in FIG. 13 (compounds 14) was synthesized. To determine whether analogs binding to one R protein could bind other R proteins simply by substituting the cognate side chain, a second series of molecules (FIG. 13, 5-8) with $C_4$ side chains was synthesized, and their ability to activate RhlR using a rhlI-gfp reporter strain, PAO-JP2 (prhlI-LVAgfp), was tested (de Kievit et al., *Appl. Environ. Microbiol.* 67:865-1873 (2001), which is hereby incorporated by reference in its entirety).

N-(trans-2-hydroxycyclopentyl)-3-oxododecanamide (2)

To a solution of 3,3-ethylenedioxydodecanoic acid (55 mg, 0.213 mmol) (Pearson et al., *Proc. Natl Acad. Sci. USA* 91:197-201 (1994); Bu et al., Synthetic agonists of a *Pseudomonas aeruginosa* quorum sensing molecule, submitted for publication, which are hereby incorporated by reference in their entirety) and trans-2-amino-cyclopentanol hydrochloride (35 mg, 0.256 mmol, purchased from Aldrich, 52,586-3) in anhydrous DMF (2 mL) was added successively EDC (49 mg, 0.256 mmol), DMAP (32 mg, 0.256 mmol), and i-$Pr_2$NEt (45 µL, 0.256 mmol) at room temperature. The mixture was stirred for 18 hours. After removing DMF in vacuo, the residue was dissolved into ethyl acetate (20 mL) and washed with 0.1 M HCl saturated with NaCl (20 mL). The aqueous phase was extracted with ethyl acetate (3×40 mL). The combined organic extracts were dried over $MgSO_4$ and concentrated to give a crude intermediate (57 mg, 79%). The 3,3-ethylenedioxy protective group was deprotected by treatment of the intermediate dissolved in 1 mL $CH_2C_{12}$ with 1 mL 95% TFA for 2 hours at room temperature. The organic solvent was briefly removed under reduced pressure, and the residue was mixed with saturated aqueous $NaHCO_3$ followed by extraction with ethyl acetate (3×40 mL). The organic layers were combined and washed once with brine, and dried over MgSO$_4$. After concentration, the residue was purified by flash chromatography on silica gel to give N-(trans-2-hydroxycyclopentyl)-3-oxododecanamide in the ketone form (14.8 mg, 0.050 mmol, R$_f$=0.42) and the enol form (19.2 mg, 0.065 mmol, R$_f$=0.15) in a total of 54% yield. Ketone form: IR (KBr) 3270, 2921, 1716, 1646, 1613, 1561 cm$^{-1}$; $^1$H NMR (500 MHz, CDCl$_3$) δ 0.88 (t, J=7 Hz, 3H), 1.20-1.35 (m, 12H), 1.48-1.52 (m, 1H), 1.58 (m, 2H), 1.60-1.78 (m, 2H), 1.81 (m, 1H), 2.05 (m, 1H), 2.16 (m, 1H), 2.52 (t, J=7 Hz, 2H), 3.42 (s, 2H), 3.84 (m, 1H), 3.98 (m, 1H), 4.24 (s, 1H), 7.40 (s, 1H); $^{13}$C (125 MHz, CDCl$_3$): 14.1, 21.3, 22.6, 23.3, 28.95, 29.20, 29.30, 29.35, 30.3, 31.8, 32.6, 44.0, 47.9, 60.7, 79.5, 167.5, 207.4; EI-HRMS calc'd for C$_{17}$H$_{31}$O$_3$N (M$^+$) 297.2298. found 297.2299. Enol form: IR (KBr) 2918, 2952, 1655, 1424, 1365, 832 cm$^{-1}$; $^1$H NMR (500 MHz, CDCl$_3$) δ 0.88 (t, J=7.5 Hz, 3H), 1.20-1.38 (m, 12H), 1.52 (m, 2H), 1.62 (m, 1H), 1.78-1.96 (m, 3H), 2.15 (td, J=7 Hz, 1.5 Hz, 2H), 2.30 (m, 2H), 3.56 (m, 1H), 4.27 (m, 1H), 5.03 (d, J=1.5 Hz, 1H), 6.82 (s, 1H); $^{13}$C (125 MHz, CDCl$_3$) δ 14.1, 21.1, 22.6, 27.6, 28.9, 29.24, 29.29, 29.42, 30.66, 30.69, 31.8, 36.6, 57.3, 87.8, 98.2, 165.6, 168.7; EI-HRMS calc'd for C$_{17}$H$_{29}$O$_2$N (M-H$_2$O) 279.2193. found 279.2197.

N-(2-oxocyclopentyl)-3-oxododecanamide (1)

Oxalyl chloride (42.5 μL, 0.486 mmol) in 1 μL anhydrous CH$_2$Cl$_2$ was cooled to −78° C. under an argon atmosphere, and anhydrous DMSO (69 μL, 0.974 mmol) was added via a syringe. The mixture was stirred for 2 minutes. 2 with the 3,3-ethylenedioxy protective group at the 2-oxo position (83 mg, 0.243 mmol) in 1 mL CH$_2$Cl$_2$ was added via a syringe, and the mixture was stirred for 15 minutes. Triethylamine (169 μL, 1.215 mmol) was added to the resulting solution, and the stirring was continued for 5 minutes. After warming to room temperature, the reaction was quenched by the addition of 20 mL 0.1 M HCl. The resulting mixture was extracted with ethyl acetate (3×30 mL), and the combined organic layers were washed sequentially with saturated aqueous NaHCO$_3$ and brine. All the extracts were combined, dried (MgSO$_4$), and concentrated to give the crude intermediate 1 with the protective group (57 mg). This molecule was treated with 95% TFA in the same manner as in the synthesis of 2, and its chromatographic purification on silica gel afforded 1 (42 mg, 0.14 mmol) in 85% yield. IR (KBr) 3244, 2927, 1752, 116, 1651, 1591, 1567 cm$^{-1}$; $^1$H NMR (500 MHz, CDCl$_3$) δ 0.879 (t, J=7.5 Hz, 3H), 1.20-1.36 (m, 12H), 1.52-1.64 (m, 2H), 1.64-1.76 (m, 1H), 1.80-1.92 (m, 1H), 2.04-2.16 (m, 1H), 1.98-2.08 (m, 1H), 2.36-2.44 (m, 1H), 2.53 (t, J=7.5 Hz, 2H), 2.55-2.69 (m, 1H), 4.12-4.20 (m, 1H), 7.40 (d, J=5 Hz, 2H); $^{13}$C (125 MHz, CDCl$_3$) δ 14.0, 18.2, 22.6, 23.3, 28.92, 29.17, 29.28, 29.31, 29.61, 31.8, 35.0, 43.8, 48.4, 57.8, 166.0, 206.6, 214.5; EI-HRMS calc'd for C$_{17}$H$_{29}$O$_3$N (M$^+$) 295.2142. found 295.2145.

N-(trans-2-hydroxycyclohexyl)-3-oxododecanamide (4)

The same procedure as the synthesis of 1 was performed, except that trans-2-amino-cyclohexanol hydrochloride was used instead of trans-2- amino-cyclopentanol hydrochloride. Column chromatography of the crude product gave 4 in the ketone form (23 mg, 0.074 mmol, R$_f$=0.29) and enol form (11 mg, 0.035 mmol, R$_f$=0.17) in a total of 51% yield. Ketone form: IR (KBr) 3274, 2927, 1715, 1652, 1617, 1564 cm$^{-1}$; $^1$H NMR (500 MHz, CDCl$_3$) δ 0.88 (t, J=7.5 Hz, 3H), 1.18-1.40 (m, 16H), 1.58 (m, 2H), 1.72 (m, 2H), 1.90-2.10 (m, 2H), 2.53 (t, J=7.5, 2H), 3.35 (m, 1H), 3.43 (s, 2H), 3.67 (m, 1H), 7.19 (d, J=5 Hz, 1H); $^{13}$C (125 MHz, CDCl$_3$) δ 14.1, 22.6, 23.3, 23.9, 24.5, 28.9, 29.21, 29.31, 29.34, 31.2, 31.8, 34.2, 44.0, 48.3, 55.7, 75.2, 167.3, 207.5; EI-HRMS calc'd for C$_{18}$H$_{33}$O$_3$N (M$^+$) 311.2455. found 311.2463. Enol form: IR (KBr) 2921, 2853, 1668, 1452, 1040 cm$^{-1}$; $^1$H NMR (500 MHz, CDCl$_3$) δ 0.88 (t, J=7.5 Hz, 3H), 1.16-1.60 (m, 18H), 1.75 (m, 2H), 2.00-2.24 (m 4H), 3.25 (m, 1H), 3.84 (m, 1H), 5.02 (d, J=2 Hz), 5.60 (s, 1H); $^{13}$C (125 MHz, CDCl$_3$) δ 14.1, 22.7, 23.2, 23.4, 27.3, 28.9, 29.27, 29.33, 29.44, 31.5, 31.9, 32.2, 36.8, 54.2, 82.7, 97.4, 166.1, 167.8; EI-HRMS calc'd for C$_{18}$H$_{31}$O$_2$N (M-H$_2$O) 293.2349. found 293.2357.

N-(2-oxocyclohexyl)-3-oxododecanamide (3)

The same procedure for the preparation of 1 was used, except that the starting material was 4 with the 3,3-ethylenedioxy protective group at the 2-oxo position (117 mg, 0.38 mmol). The crude product was purified by flash chromatography (hexane/EtOAc 1:2, R$_f$=0.38) to give 3 (87 mg, 0.28 mmol) in 73% yield. IR (KBr) 3280, 2935, 1712, 1654, 1628, 1550 cm$^{-1}$; $^1$H NMR (500 MHz, CDCl$_3$) δ 0.877 (t, J=7 Hz, 3H), 1.20-1.34 (m, 12H), 1.36-1.44 (m, 1H), 1.55-1.70 (m, 3H), 1.76-1.84 (m, 1H), 1.84-1.95 (m, 1H), 2.11-2.20 (m, 1H), 2.36-2.44 (m, 1H), 2.50-2.60 (m, 3H), 2.60-2.65 (m, 1H), 3.41 (s, 2H), 4.45-4.55 (m, 1H), 7.53 (d, J=4 Hz, 1H); $^{13}$C (125 MHz, CDCl$_3$) δ 14.0, 22.6, 23.3, 24.0, 27.9, 28.96, 29.20, 29.31, 29.34, 31.8, 35.1, 41.1, 43.7, 49.2, 58.2, 165.3, 206.0, 207.0; EI-HRMS calc'd for C$_{18}$H$_{31}$O$_3$N (M$^+$) 309.2298. found 309.2284.

N-(trans-2-hydroxy)cyclopentylbutanamide (6) and N-(trans-2-hydroxy)cyclohexylbutanamide (8)

The procedure for the preparation of C$_4$-HSL was used for this series of molecules. The EDC-mediated coupling of butyric acid and trans-2- amino-cyclopentanol or trans-2-amino-cyclohexanol afforded 6 in 66% yield or 8 in 82% yield. 6: IR (KBr) 3284, 2960, 1643, 1567, 1058 cm$^{-1}$; $^1$H NMR (500 MHz, CDCl$_3$) δ 0.952 (t, J=7.5 Hz, 3H), 1.40-1.50 (m, 1H), 1.60-1.74 (m, 4H), 1.75-1.82 (m, 1H), 1.96-2.08 (m, 1H), 2.08-2.18 (m, 1H), 2.19 (t, J=7 Hz, 2H), 3.80-3.86 (m, 1H), 3.92-4.00 (m, 1H), 4.90 (s, 1H), 6.28 (s, 1H); $^{13}$C (125 MHz, CDCl$_3$) δ 13.6, 19.0, 21.1, 30.0, 32.3, 38.0, 60.5, 79.5, 175.3; EI-HRMS calc'd for C$_9$H$_{17}$O$_2$N (M$^+$) 171.1254. found 171.1257. 8: IR (KBr) 3294, 2930, 1638, 1567, 1086, 1072 cm$^{-1}$; $^1$H NMR (500 MHz, CDCl$_3$): 0.952 (t, J=7.5 Hz, 3H), 1.15-1.20 (m, 4H), 1.60-1.80 (m, 4H), 1.98 (m, 2H), 2.20 (t, J=7.5, 2H), 3.30-3.34 (m, 1H), 3.54-3.60 (m, 1H), 4.20 (s, 1H), 6.30 (d, J=7 Hz, 1H); $^{13}$C (125 MHz, CDCl$_3$) δ 13.5, 19.1, 24.0, 24.4, 31.3, 34.3, 38.4, 55.6, 74.8, 174.9; EI-HRMS calc'd for C$_{10}$H$_{19}$O$_2$N (M$^+$) 185.1410. found 185.1410.

N-2-oxocyclopentylbutanamide (5) and N-2-oxocyclohexylbutanamide (7)

Swern oxidation, similar to the synthesis of 1, was performed to afford 5 in 60% yield and 7 in 48% yield. 5:IR (KBr) 3256, 2963, 1744, 1641, 1555 cm$^{-1}$; $^1$H NMR (500 MHz, CDCl$_3$) δ 0.954 (t, J=7.5 Hz, 3H), 1.56-1.70 (m, 3H), 1.82-1.94 (m, 1H), 2.02-2.10 (m, 1H), 2.18-2.26 (m, 3H), 2.38-2.44 (m, 1H), 2.60-2.68 (m, 1H), 4.10-4.20 (m, 1H), 6.00 (s, 1H); $^{13}$C (125 MHz, CDCl$_3$) δ 13.6, 18.0, 18.9, 30.1, 34.9, 38.1, 173.3, 215.4 EI-HRMS calc'd for C$_9$H$_{15}$O$_2$N (M$^+$) 169.1097. found 169.1101. 7: IR (KBr) 3295, 2943, 1719, 1643, 1552 cm$^{-1}$; $^1$H NMR (500 MHz, CDCl$_3$) δ 0.95 (t, J=7 Hz, 3H), 1.25-1.40 (m, 1H), 1.60-1.70 (m, 3H), 1.78-1.90 (m, 2H), 2.10-2.19 (m, 1H), 2.20 (t, J=7 Hz, 2H), 2.36-

2.44 (m, 1H), 2.50-2.55 (m, 1H), 2.64-2.72 (m, 1H), 4.40-4.60 (m, 1H), 6.42 (s, 1H); $^{13}C$ (125 MHz, CDCl$_3$) δ 13.7, 19.1, 24.0, 28.1, 35.6, 38.6, 41.2, 58.0, 172.7, 208.0; EI-HRMS calc'd for $C_{10}H_{17}O_2N$ (M$^+$) 183.1254. found 183.1259.

Example 7—Reporter Gene Assays

Reporter strains were grown overnight in LB plus 300 μg/ml carbenicillin at 37° C. and diluted to an OD$_{600}$ of 0.1. Following an incubation of 1 hour, 200 μl of cell culture was added to individual wells of a 96 well plate containing appropriate amount of test compound(s). Plates were incubated for 6 hours and then scanned for fluorescence emission with a Molecular Imager (488 nm excitation and 695 nm bandpass filter). Fluorescence was quantified with ImageQuant software.

Figure 14:
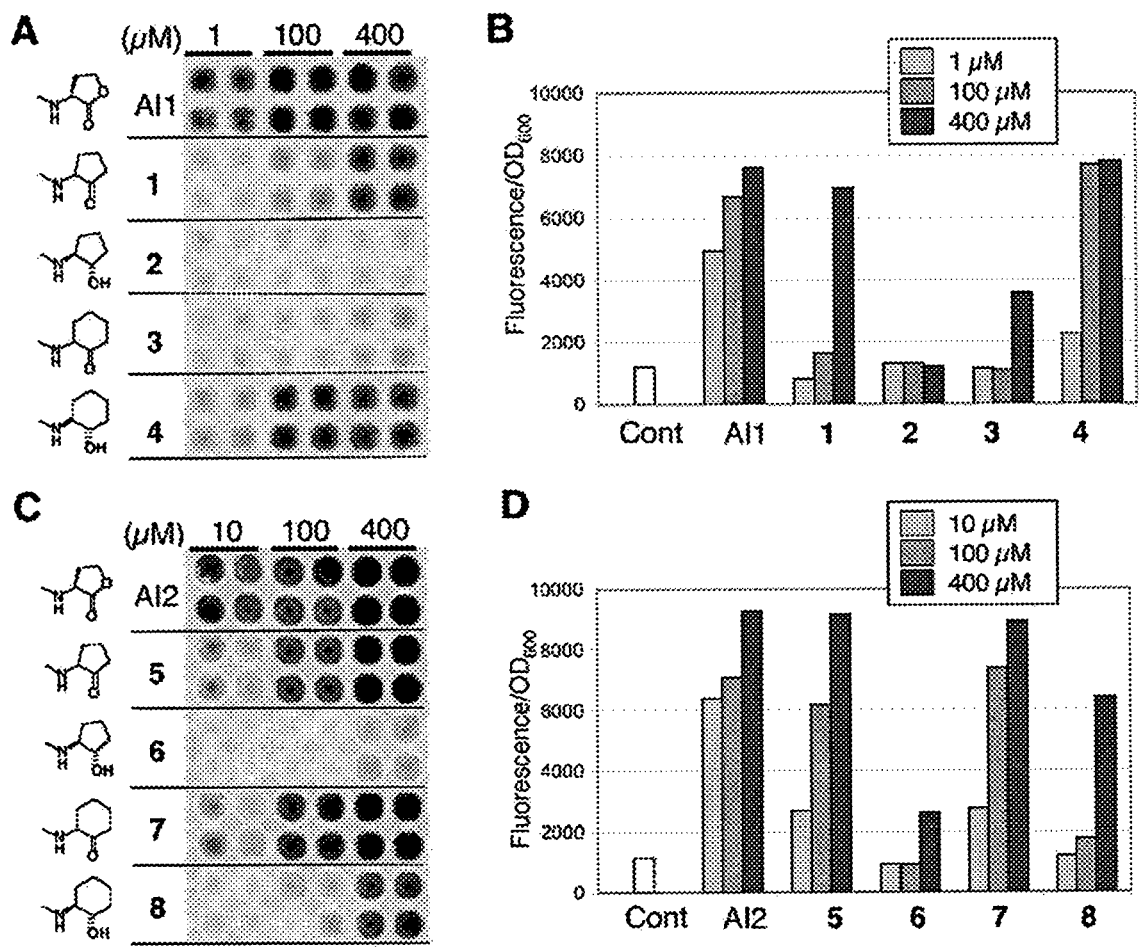
FIGS. 14A-D show reporter gene induction by autoinducers and their analogs.

Using the PAO-JP2 (plasI-LVAgfp) reporter strain, activity of the 3-oxo-C$_{12}$ molecules, AI1, and 14 was tested. Strong QS induction by AI1 was evidenced by the high GFP signal observed at as low as 1 μM of AI1 (FIG. 14A and B, AI1). The previously identified agonist, 3-oxo-C$_{12}$(2-aminocyclohexanol) 4, showed strong agonist activity with GFP induction only 2-fold less than AI1 at 1 μM, and comparable to AI1 at higher concentrations (FIGS. 14A and B, 4). 3-oxo-C$_{12}$-(2-aminocyclopentanone) 1 is structurally more similar to AI1 than 4, since the oxygen of HSL was simply replaced with carbon in 1. Hence, it was expected that 1 would have strong agonist activity. Contrary to this prediction, 1 was able to induce the reporter only at a very high concentration (FIGS. 14A and B, 1). Even more surprising, compounds 2 and 3 were nearly unable to induce the reporter, even at high concentrations (FIGS. 14A and B, 2 and 3).

The C$_4$ compounds (A12 and 5-8) were analyzed for agonist activity using PAO-JP2 (prhlI-LVAgfp) (FIGS. 14C and D). Induction of GFP expression in this reporter requires addition of both AI1 and AI2. The AI2 control and agonist assays, therefore, were performed in the presence of 1 μM AI1 and increasing concentrations of AI2 or analog (FIGS. 14C and D). Both ketone derivatives, 5 and 7, showed strong agonist activity, inducing the reporter at just 10 μM (FIGS. 14C and D, 5 and 7). In contrast, the 2-aminocyclopentanol derivative 6 had no agonist activity. Moreover, the 2-aminocyclohexanol derivative 8 had very little AI2 agonist activity; it could induce only moderate GFP expression at 400 μM (FIGS. 14C and D, column 8).

As mentioned above, it was initially assumed that since 2-aminocyclopentanone (1 and 5) and 2-aminocyclohexanone (3 and 7) have a keto group, they would better mimic the HSL structure than the 2-aminocyclopentanol (2 and 6) and 2-aminocyclohexanol (4 and 8). In fact, in the rhl circuit the ketone derivates were better agonists of AI2 than the alcohol derivatives. This is also consistent with the crystal structure of the TraR-3-oxo-C$_8$ HSL complex which shows the ketone participating in an H bond. Presumably, an alcohol substitution could maintain the H bond, but less efficient binding would be expected. The results for the AI1 analogs, however, do not fit this pattern. In the las circuit, 2-aminocyclohexanol 4 was the strongest agonist, 2-aminocyclopentanone 1 was a weak agonist, and 2-aminocyclohexanone 3 had no agonist activity. Thus, based on these results, it is proposed that the microenvironment of the protein-HSL interface differs between LasR, RhlR, and TraR.

An intriguing observation was that a subtle structural change from hydroxyl to keto group on the cyclohexane ring (4→3), or from keto to hydroxyl group on the cyclopentane ring (1→2 or 5→6), drastically reduced agonist activity. It is unlikely that such a small structural difference would completely eliminate binding to the respective R protein. A more likely, alternative explanation is that the cyclopentanol (2) and cyclohexanone (3) compounds can still bind LasR with similar affinity but are unable to activate it. Therefore, it appears that compounds 2 and 3 might act as AI1 antagonists. Similarly, compound 6 should maintain the ability to bind RhlR, and therefore should act as an AI2 antagonist.

Example 8—Antagonist Assays

Based on the above hypothesis, a competition assay of 2 and 3 against AI1, using strain PAO-JP2 (plasI-LVAgfp), was performed. As predicted, compound 2 inhibited GFP expression approximately 70% at a 100-fold excess concentration over AI1 (FIG. 15A), and compound 3 had a lesser inhibitory effect (35% reduction) under the same conditions. It should be noted that this inhibition experiment was performed with competition against 1 μM AI1, a concentration typically produced by wild type *P. aeruginosa* (Pearson et al., *Proc. Natl Acad. Sci. USA* 92:1490-1494 (1995), which is hereby incorporated by reference in its entirety). These results indicate that both molecules bind LasR and prevent it from being activated by AI1. This view is supported by the compounds' inability to inhibit GFP expression when the lasI promoter is replaced with a lac promoter in strain PAO-JP2 (pTdK-GFP) (de Kievit et al., *Appl. Environ. Microbiol.* 67:1865-1873 (2001), which is hereby incorporated by reference in its entirety). It should also be noted that cell growth was not affected by the addition of 2 or 3 at concentrations up to 400 μM. Thus, it appears that compounds 2 and 3 act as specific inhibitors of QS controlled promoters. Compound 6 was also tested for its ability to compete against AI2, but no inhibition of the rhlI-gfp reporter gene was seen.

Figure 15:
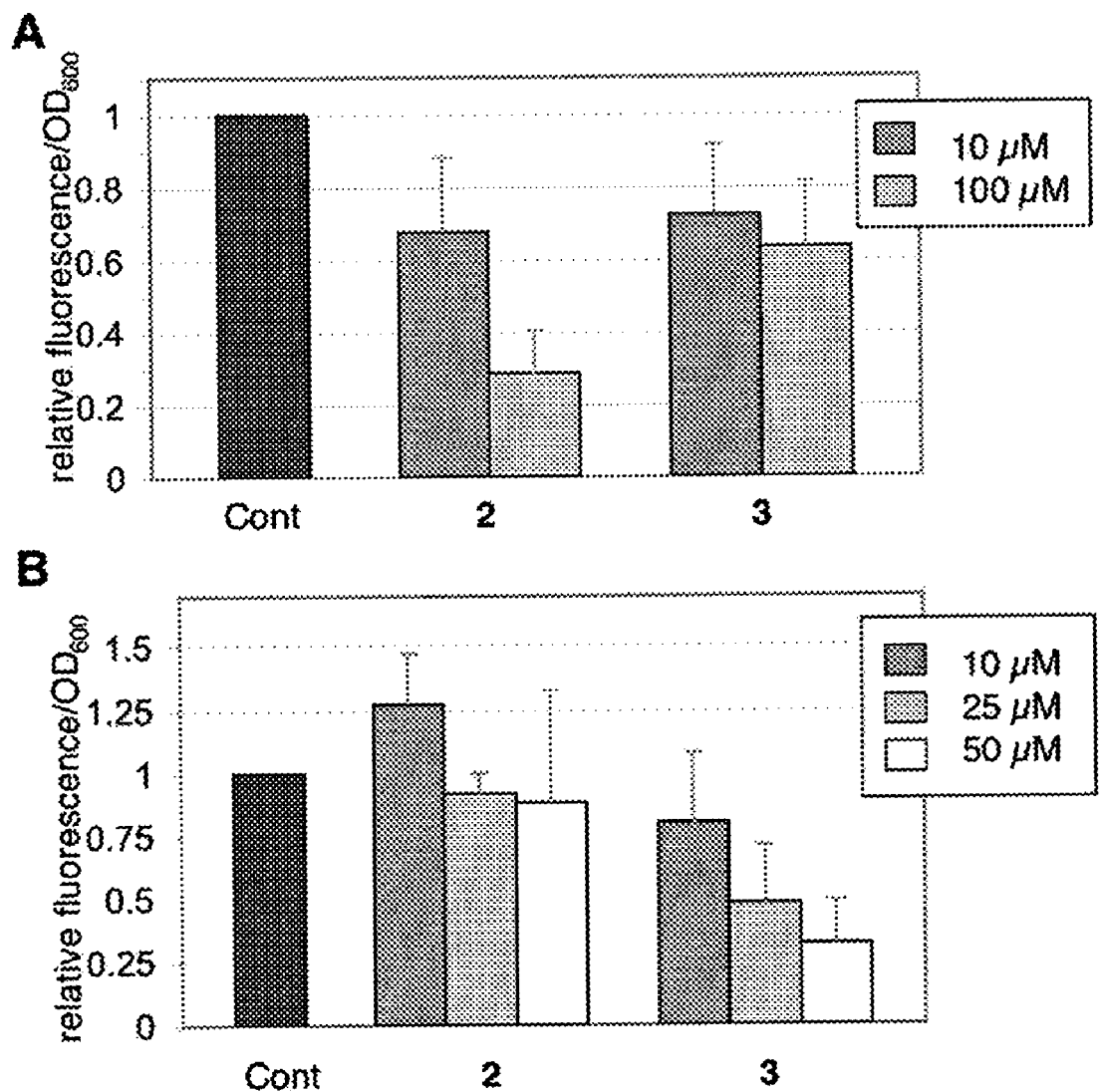
FIGS. 15A-B show antagonist assays.

Next the ability of 2 and 3 to inhibit the rhlI-gfp reporter strain PAO-JP2 (prhlI-LVAgfp) was tested, since this expression is also AI1-dependent. The Iglewski group recently reported that the rhlI promoter is induced primarily by the LasR-AI1 complex (de Kievit et al., *FEMS Microbiol. Lett.* 212:101-106 (2002), which is hereby incorporated by reference in its entirety), but no induction of this promoter was seen with the addition of only AI1. It is possible that the rhlI-lacZ reporter used in their study is more sensitive than the rhlI-gfp construct used in this study, and the small amount of GFP induced by AI1 is below this limit of detection. However, since both AI1 and AI2 are required to induce GFP from the PAO-JP2 (prhlI-LVAgfp) reporter, the data is interpreted in the context of earlier experiments that showed predominantly RhlR-AI2 activation of the rhlI promoter (Latifi et al., *Mol. Microbiol.* 21:1137-1146 (1996), which is hereby incorporated by reference in its entirety). Surprisingly, compound 2 showed no antagonist activity in this assay (FIG. 15B). More promising results were obtained from the assay of compound 3, where GFP expression of the rhlI-gfp reporter was inhibited by greater than 60% at 50 μM when competing against 1 μM AI1 and 10 μM AI2 (FIG. 15B).

Inhibition by compound 3 of the rhlI-gfp reporter was greater than that seen with the lasI-gfp reporter. Results from the lasI-gfp assay indicate that 3 inhibits LasR-AI1 dependent activation of transcription (FIG. 15A). Since the rhlR promoter is also activated by LasR-AI1, inhibition of rhlI-gfp in the presence of 3 is likely due to inhibition of LasR-AI1 dependent activation of rhlR expression. This then translates into reduced activation of RhlR-AI2 dependent rhlI-gfp expression. It is also possible, however, that 3 directly interacts with RhlR and prevents AI2 binding, since AI1 is able to act as an antagonist against RhlR and prevent binding by AI2

(Pesci et al., *J. Bacteriol.* 179:3127-3132 (1997), which is hereby incorporated by reference in its entirety). The AI2 analog with the same ring structure as compound 3 (compound 7, 2-aminocyclohexanone) is a strong agonist of RhlR. This supports the speculation that 3 could enter the AI1 binding site of RhlR and antagonize the RhlR-AI2 interaction. The chain length of RhlR autoinducers appears to be the determining factor regulating RhlR activation, since $C_4$HSL activates RhlR but 3-oxo-$C_{12}$HSL antagonizes it, and no $C_4$ analogs have been identified that can antagonize it. Regardless of the mechanism of inhibition by compound 3, since the rhlI target is further downstream in the LasR signaling pathway than lasI, a stronger inhibition of rhlI than lasI would be expected.

Example 9

Virulence Factor Assays

In order to provide further evidence that compounds 2 and 3 are disrupting QS, their ability to reduce expression of virulence factors in both the AI1 synthase knockout (PAO-JP2) and wild type (PAO1) *P. aeruginosa* strains was tested. Two important virulence factors in Pseudomonas infections were chosen for the assay. First, the pigment pyocyanin that is required for disease in the *Arabidopsis thaliana* (Rahme et al., *Proc. Natl Acad. Sci. USA* 94:13245-13250 (1997), which is hereby incorporated by reference in its entirety), *Caenorhabditis elegans* (Mahajan-Miklos et al., *Cell* 96:47-56 (1999), which is hereby incorporated by reference in its entirety), and *Galleria mellonella* (Jander et al., *J. Bacteriol* 182:3843-3845 (2000), which is hereby incorporated by reference in its entirety) infection models, and causes serious tissue damage in chronic lung infections (Wilson et al., *Infect. Immun.* 56:2515-2517 (1988), which is hereby incorporated by reference in its entirety). Second, the metalloprotease Elastase B, which degrades immune components and causes tissue damage (Kon et al., *FEMS Immunol. Med. Microbiol.* 25:313-321 (1999), which is hereby incorporated by reference in its entirety).

For the pyocyanin assay, cells were grown overnight in LB then washed in fresh media and diluted to an $OD_{600}$ of 0.05. This culture was grown for 3-4 hours to mid-log phase ($OD_{600}$ of 0.3-0.5), then diluted to an $OD_{600}$ of 0.05, and aliquoted to test tubes containing an appropriate amount of test compound(s). Following 18 hours of growth, pyocyanin was extracted from filtered culture supernatants and quantified using standard methods (Essar et al., *J. Bacteriol.* 172: 884-900 (1990), which is hereby incorporated by reference in its entirety).

Figure 16:
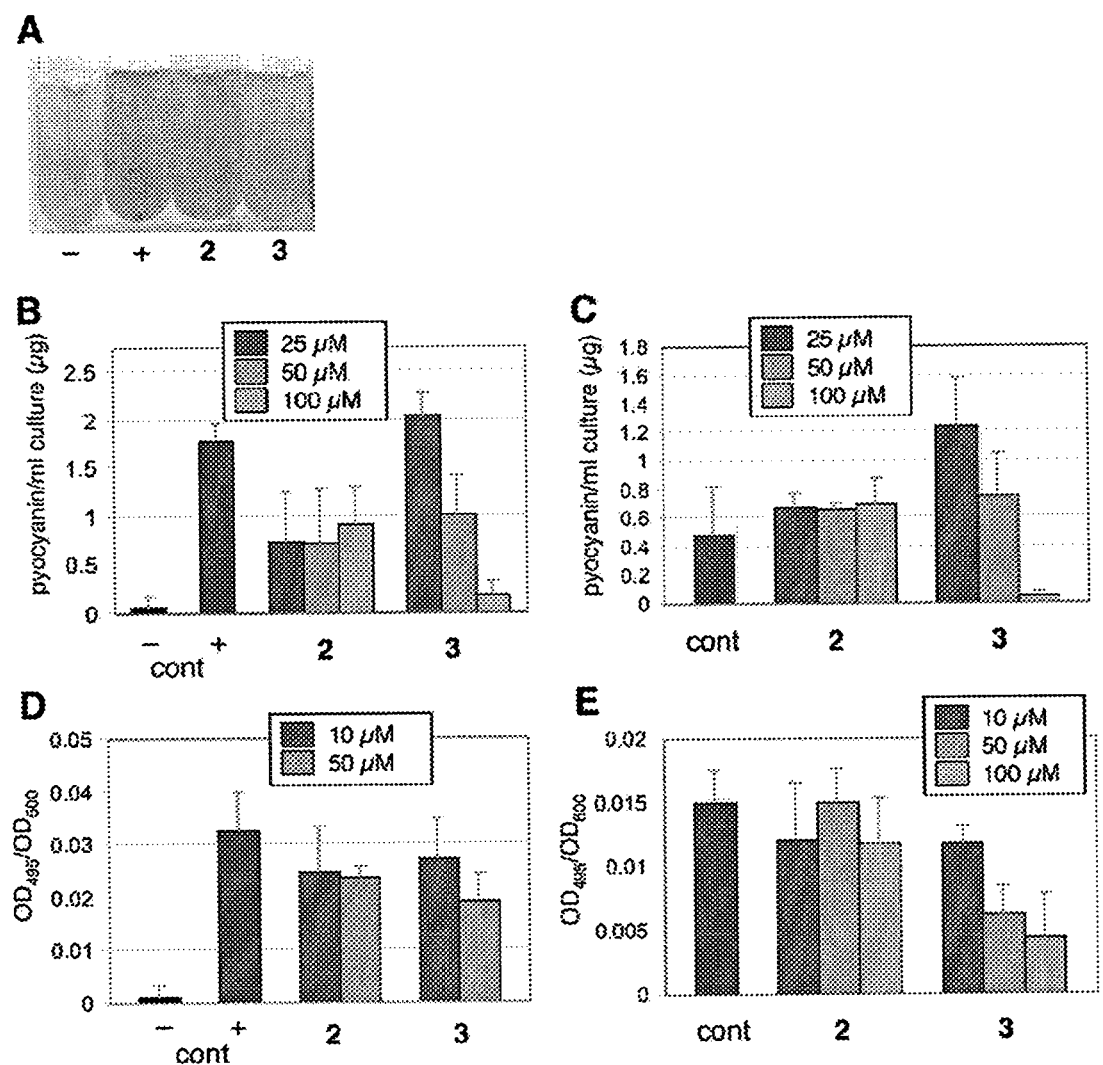
FIGS. 16A-E show virulence factor assays.

Strong induction of pyocyanin in *P. aeruginosa* PAO-JP2 requires addition of both AI1 and AI2 (FIGS. 16A and 4B). When compound 3 was added in combination with exogenous AIs, there was nearly complete inhibition of pyocyanin expression (FIGS. 16A and B). A very similar inhibitory effect by 3 was observed when wild type *P. aeruginosa* (PAO1) was assayed (FIG. 16C). The concentration dependent inhibitory effect of 3 led us to believe that 3 is specifically competing against AI activation of pyocyanin expression. Compound 2, on the other hand, reduced pyocyanin expression by 50% in PAO-JP2 (FIGS. 16A and B), but the inhibition was not concentration dependent over the range tested. Moreover, 2 had no significant effect on PAO1 (FIG. 16C). Therefore, the inhibitory effect of 2 on pyocyanin expression is not as significant as that of 3.

For the elastase B assay, cells (PAO-JP2) were grown overnight in PTSB media (5% Peptone, 0.1% Tryptic Soy Broth) at 37° C., washed and diluted to an $OD_{600}$ of 0.05, grown to mid-log phase, washed again, and re-suspended to an $OD_{600}$ of 0.05. The culture was then added to test tubes containing test compound(s) and grown for 6 hours. Elastase B activity was quantified by incubation of 100 µl of filtered culture supernatant with 5 mg Elastin Congo Red substrate and 1 ml of 10 mM Tris pH 7.2, 1 mM $CaCl_2$ for 6 hours at 37° C. with agitation. Elastase B activity is represented by the $OD_{495}$ of the enzyme assay following reaction quenching with EDTA and centrifugation to remove unreacted substrate, divided by the $OD_{600}$ of the cell culture. The same assay was run with strain PAO-1, however no exogenous autoinducers were added. Thus, a colorimetric assay was conducted using Elastin Congo Red substrate, so the observed protease activity is predominantly due to Elastase B and not other proteases that might be present in culture supernatants (FIGS. 16D and E) (Caballero et al., *Analytical Biochem.* 290:330-337 (2001), which is hereby incorporated by reference in its entirety). The control experiment showed that 5 µM AI1 and 10 µM AI2 were required for consistent induction of elastase B activity in PAO-JP2. At 50 µM 3, elastase activity was reduced to 60% of the positive control level (FIG. 16D). When the same assay was performed on wild type *P. aeruginosa*, elastase activity was reduced to 30% of the control level in the presence of 100 µM 3 (FIG. 16E). These results indicate that 3 likely inhibits elastase B expression, although the inhibition was not as strong as that observed for pyocyanin expression. On the other hand, compound 2 had no significant effect on elastase activity produced by either strain (FIGS. 16D and E). Since 2 showed weaker inhibition of pyocyanin and elastase production than 3, future studies focused solely on 3.

Example 10—Static Biofilm Assay

There is evidence that the chronic nature of *P. aeruginosa* infections is due in part to biofilm growth (Singh et al., *Nature* 407:762-764 (2000); Drenkard et al., *Nature* 416:740-743 (2002), which are hereby incorporated by reference in their entirety). Biofilm is an attached colony of bacteria protected from biocide treatment and the host immune response by a secreted polysaccharide matrix (O'Toole et al., *Annu. Rev. Microbiol.* 54:49-79 (2000), which is hereby incorporated by reference in its entirety). Its development in *P. aeruginosa* is QS controlled, and disruption of QS has been shown to eliminate or reduce biofilm development (Davies et al., *Science* 280:295-298 (1998); Wu et al., *Microbiol.* 147:1105-1113 (2001); Shirtliff et al., *Chem. & Biol.* 9:859-871 (2002), which are hereby incorporated by reference in their entirety). Prevention of biofilm growth continues to be a challenge, since treatment of biofilm colonies has proven extremely difficult.

Compound 3 was tested for its effect on biofilm development in a 24-hour assay that looks at the early stages of biofilm formation. The static biofilm assay is a simple yet reliable method to monitor QS-controlled steps of biofilm formation (de Kevit et al., *Appl. Environ. Microbiol* 67:1865-1873 (2001), which is hereby incorporated by reference in its entirety). Cells (strain PAO-JP2 (pTdK-GFP) (de Kevit et al., *Appl. Environ. Microbiol.* 67:1865-1873 (2001), which is hereby incorporated by reference in its entirety), which contains a constitutively expressed GFP construct for visualization by scanning confocal laser microscopy) were grown in M9 media (47.7 mM $Na_2HP_4.7H_2O$, 21.7 mM $KH_2PO_4$, 8.6 mM NaCl, 18.7 mM $NH_4Cl$, 0.5% casamino acids, 11.1 mM glucose, 1 MM $MgSO_4$) plus carbenicillin (300 µg/ml) overnight, washed, and re-suspended to an $OD_{600}$ of 0.05, grown to mid-log phase, then diluted to an $OD_{600}$ of 0.05, and added to sterile shell vials containing glass coverslips (ViroMed Laboratories, Minneapolis, Minn.) on which the test compounds had been applied. Cultures were grown at 37° C. with shaking for 30 minutes, and then allowed to sit at 37° C. for an additional 23.5 hours. Coverslips were then rinsed and placed on slides for visualization using an MRC1024 Laser Scanning Microscope (BioRad) with a Nikon Fluor-60X oil emersion objective lens (NA=1.4), 488 nm Argon Laser and OG515 filter.

Figure 17:
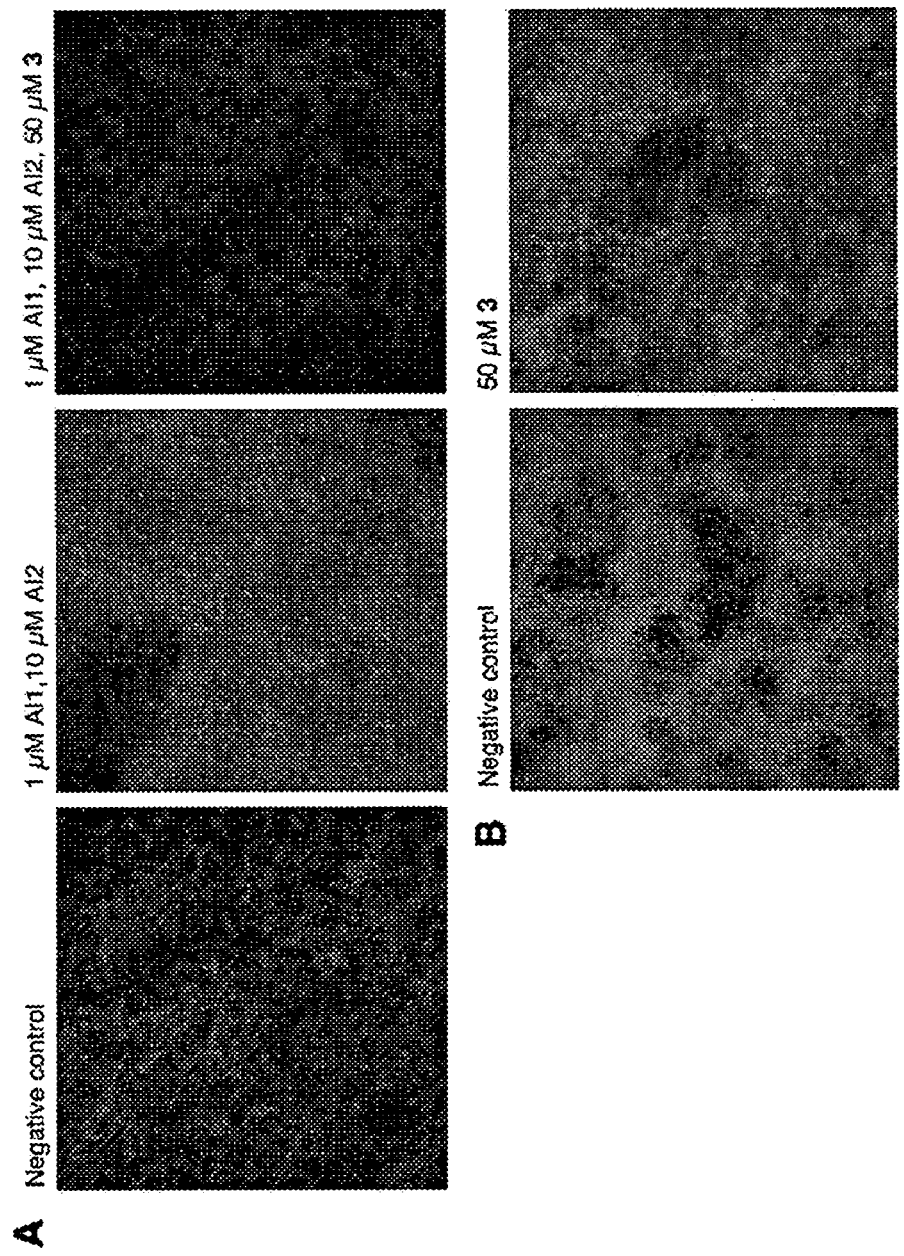
FIGS. 17A-B show a static biofilm assay.

The PAO-JP2 autoinducer synthase knockout strain did not form a biofilm unless AIs were added (FIG. 17A). When this strain was grown in the presence of AIs plus 3, biofilm formation was completely inhibited (FIG. 17A, right panel). The same assay was run with strain PAO-1 (pTdK-GFP), and no exogenous autoinducers were added. Inhibition of biofilm formation in the wild type strain, PAO1 (pTdK-GFP) (FIG. 17B), was less obvious, but there was a noticeable difference in biofilm morphology when grown in the presence of 3. The above results provide additional evidence that compound 3 interferes with QS signaling and reduces the production of important virulence factors.

Example 11—Discussion

The studies described in Examples 1-10 yielded several new compounds that agonize or antagonize the *P. aeruginosa* QS circuit. Interestingly, these molecules are structurally related to each other: all compounds have a hydroxyl or keto group adjacent to the amino group that connects to the 3-oxo-$C_{12}$ side chain, and also have six- or five-membered ring structures. A particularly intriguing discovery was that a very subtle change of the agonist 4 makes it an antagonist; the hydroxyl group to ketone (3), saturated ring to unsaturated benzene ring (3-oxo-$C_{12}$-D10), and six-membered ring to five (2).

Despite the structural similarity of antagonists, the observed activities were different. 3-oxo-$C_{12}$-(2-aminocyclohexanone) 3 (FIG. 18), nearly completely inhibited pyocyanin and biofilm, strongly inhibited both reporter genes, and moderately inhibited elastase activity. However, 3-oxo-$C_{12}$-D10 (FIG. 18), found from the library screening, showed very good inhibition of the reporter genes (stronger than 3) and moderate inhibition of elastase, but no inhibition of pyocyanin or biofilm. A similar result was seen with 2, which inhibited the las reporter and pyocyanin expression from PAO-JP2, but could not inhibit the rhl reporter or elastase.

It is clear that the effect of QS transcription factors is dependent on the individual promoters, due to the affinity of the promoter sequence for LasR and RHlR, and any number of other regulatory proteins influencing the level of activation of each gene. This would explain why a specific promoter would be more or less susceptible to inhibition. The difference between the capacity of each compound to inhibit specific virulence factors, however, is less clear. It is proposed that it is due to the ability of 3 to antagonize both LasR-AI and RhlR-AI2. 3-oxo-$C_{12}$-D10 and 2, in contrast, can only disrupt the LasR-AI1 interaction. Therefore, the rhl regulon can still be activated even though the las regulon is significantly inhibited, resulting in induction of virulence factors. Evidence supporting this hypothesis is provided by agonist assays of AI2 analogs with the corresponding ring structures. AI2, $C_4$-HSL, is the activator of RhlR. AI1, 3-oxo-$C_{12}$-HSL, was able to competitively inhibit AI2 binding to RhlR in *E. coli*. AI1 reduced binding of AI2 to RhlR by 86% when present in only 4-fold excess (Kline et al., *Bioorg. Med. Chem. Lett.* 9:3447-3452 (1999), which is hereby incorporated by reference in its entirety). Apparently, the long chain-HSL binds the same site as the short chain-HSL, but does not activate RhlR. The 2-aminocylcohexanone analog also fits into the HSL binding site of both LasR and RhlR. This is supported by the finding that $C_4$-(2-aminocylcohexanone) is a strong agonist of AI2, and 3 is a strong antagonist of AI1 (Smith et al., *Chemistry & Biology* 10:81-89 (2003), which is hereby incorporated by reference in its entirety). It appears that 3 may also antagonize the RhlR-AI2 interaction. This is a plausible hypothesis, since this compound inhibited all the virulence factors tested. Since the genes encoding elastase, pyocyanin, and biofilm are controlled by both LasR-AI1 and RhlR-AI2, it is likely that both R-proteins need to be effected to see the strong inhibition observed in the presence of 3.

In contrast, both 3-oxo-$C_{12}$-$D_{10}$ and 2 inhibited the reporter genes but were less effective at inhibiting virulence factors. It is suspected that these two compounds elicit their effects through LasR alone, and do not interact with RhlR. This is supported by the observation that neither $C_4$-(2-aminocylcopentanol) (Smith et al., *Chemistry & Biology* 10:81-89 (2003), which is hereby incorporated by reference in its entirety) nor $C_4$-D10 could activate the rhlI-gfp reporter. Since these particular HSL analogs could not activate RhlR, it seems less likely that the same analog with a 3-oxo-$C_{12}$ side chain could enter the RhlR HSL binding site.

Additional support for this hypothesis that compound 3-oxo-$C_{12}$-D10 can inhibit LasR but not RhlR function is provided by biofilm studies of *P. aeruginosa* lasI deletion strains. Davies et al. and Sauer et al. have shown that lasI mutant *P. aeruginosa* are still able to form a biofilm but maturation into the proper biofilm morphology is altered (Wilson et al., *Infect. Immun.* 56:2515-2517 (1988); Sauer et al., *J. Bacteriol.* 184:1140-1154 (2002), which are hereby incorporated by reference in their entirety). It is believed that compound D10 similarly disrupts normal biofilm development, although it cannot completely inhibit biofilm formation.

Example 12—Determination of the Chirality of A1 and Compounds 2-4

The agonist 4 and antagonists 2 and 3 (FIG. 18) were synthesized in racemic mixtures. Although HSL in AI1 is known to be the natural L-form based on the consideration of its biosynthetic mechanism, there appears to be no report describing that the D-form is inactive. Moreover, it is not necessarily true that the synthetic agonist and antagonists bear the same chirality to AI1 or that either chirality has greater activity. This is a particularly interesting issue for antagonists. Thus, both L-and D-forms (S- and R-configurations of the 2-amino carbon center) of each molecule were synthesized. Moreover, in 2 and 4, there are cis and trans geometry of the aminoalcohol's stereochemistry. Thus, the cis molecules were synthesized as well.

Figure 19:
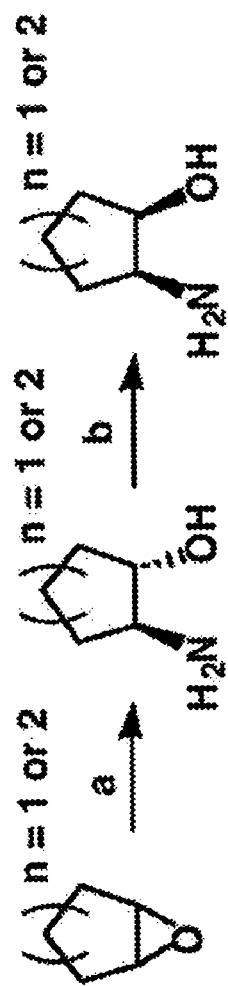
FIG. 19 shows the synthesis of chiral aminoalcohols. Reagents and conditions: (a) (i) 2 mol % Jacobsen catalyst, $TMSN_3$; (ii) MeOH, cat TFA; (iii) 2 mol % $PtO_2$, $H_0$; (b) (i) $Ac_2O$; (ii) $SOCl_2$; (iii) HCl, heat.
Figure 19:
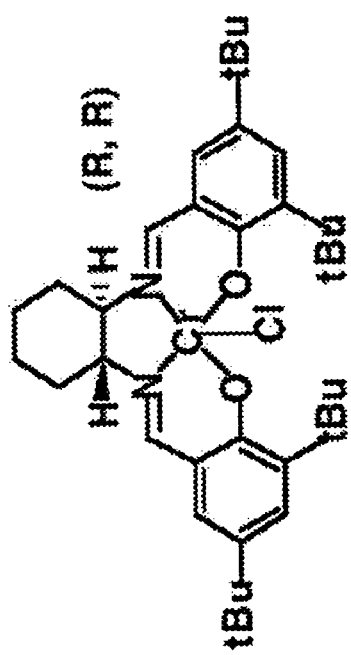

The chemistry was very straightforward. The highly enantioselective epoxidation catalysts developed by Jacobsen were used (FIG. 19). The remaining procedures are known in the literature (Jacobsen, *Acc. Chem. Res.* 33(6):421-431 (2000), which is hereby incorporated by reference in its entirety) or are described above. D-HSL was synthesized from D-homoserine, and coupled with the 3-oxo-$C_{12}$-side chain. Reporter assays using the las reporter, PAO-JP2 (plasI- LVAgfp), can be performed as described above to determine the agonist or antagonist activity of each compound.

Example 13—Expansion of las Antagonist Focused Libraries Based on the Cyclohexane and Cyclopentane Skeleton In this example, the library of las antagonists is to be expanded based on the structure of 2 and 3. The synthesis of the library will be performed based on the previously developed solid phase approach described in FIG. 2. The hydroxyl or keto group adjacent to the amino group connecting the 3-oxo-$C_{12}$-side chain will be kept intact and the substitutions on the ring will be modified.

Figure 20:
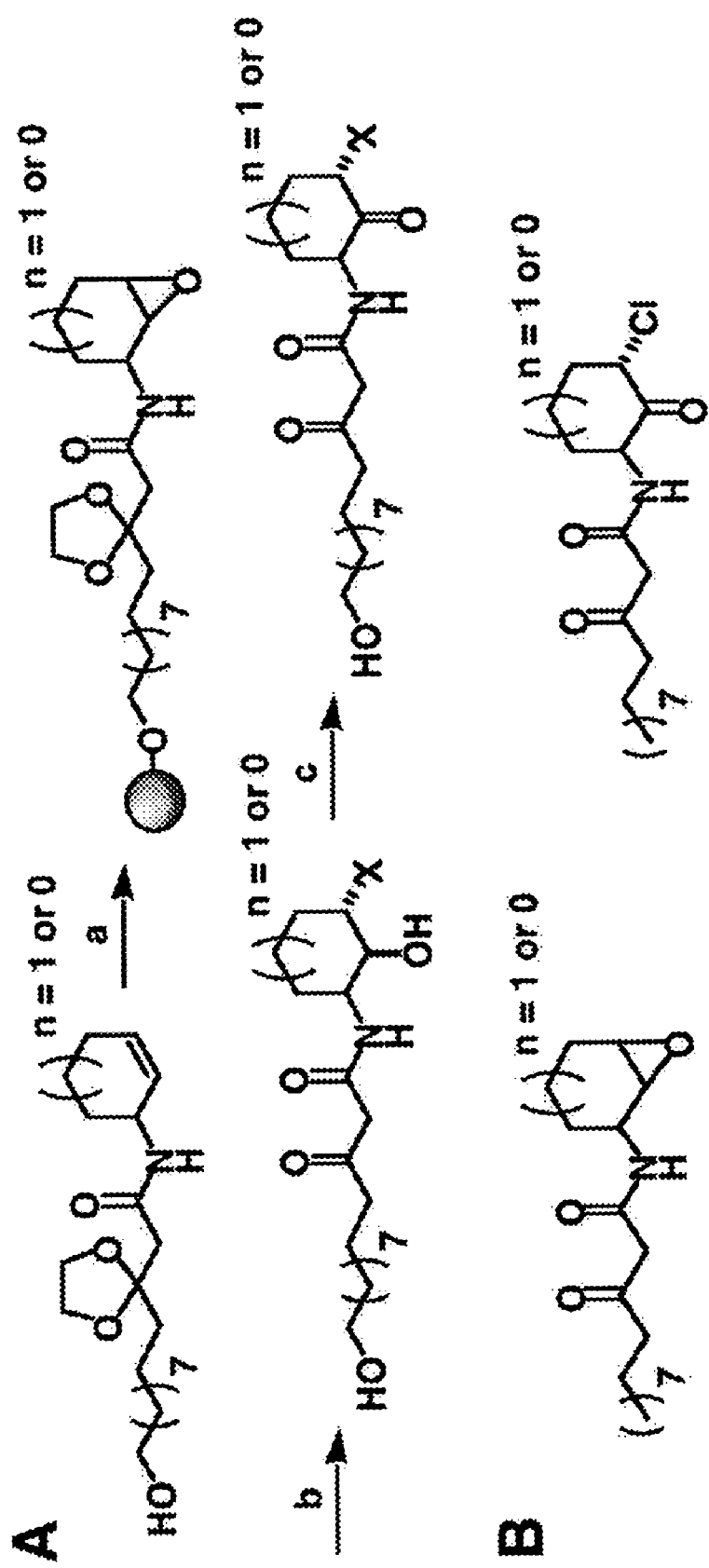
FIG. 20A shows the synthesis of las antagonist focused libraries.
FIG. 20B shows epoxy and chloro-substituted suicide compounds.

To diversify the molecular structures in the library based on 3, 3-aminoacyclohexene will be coupled with the resin-immobilized 3-oxo-$C_{13}$-side chain (FIG. 20A). 3-aminoacylhexene is commercially available in both R and S forms, so that the results obtained in Example 12 can be considered for the choice of molecule. Alternatively, the racemic form can be used to screen antagonist structure, and then the enantiomerically pure form can be re-synthesized by means of solution phase chemistry. The olefin will be oxidized to epoxide, which gives the blanching point material. Nucleophilic substitution of various organometallic alkyl and aryl groups or Lewis acid aided substitutions of various nucleophiles will yield various molecules in the library. Oxidation of the resulting molecules by Dess-Martin reagent will convert the corresponding ketones. The individual molecules can also be synthesized in solution phase, although such synthesis is more laborious but still feasible for smaller collections of molecules. Similarly, the same library construction can be performed for cyclopentane derivatives, starting from 3-aminocyclopentene.

The individual molecules will be tested using the las reporter to determine the agonist or antagonist activities for the las circuit (for antagonist assays, 1 µM AI1 will be used for competition). Once hits are identified, these molecules can then be re-synthesized in solution phase for further evaluation. The molecules will also be tested for inhibition of the rhl circuit using the rhl reporter. Upon finding potent antagonists, they will be tested for their effect on virulence factor and biofilm production.

In addition to the competitive inhibitors described above, discovery suicide inhibitors is of interest. Therefore, the epoxide molecule as well as the chlorine-substituted ketone (FIG. 20B) will also be tested.

Figure 21:
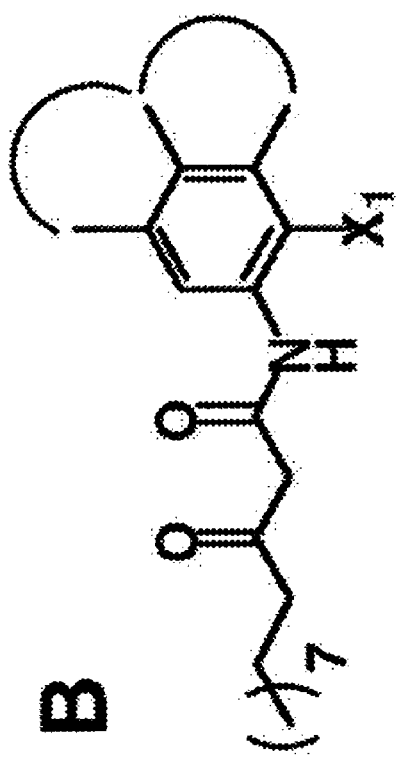
FIGS. 21A-B show aniline derivatives.
Figure 21:
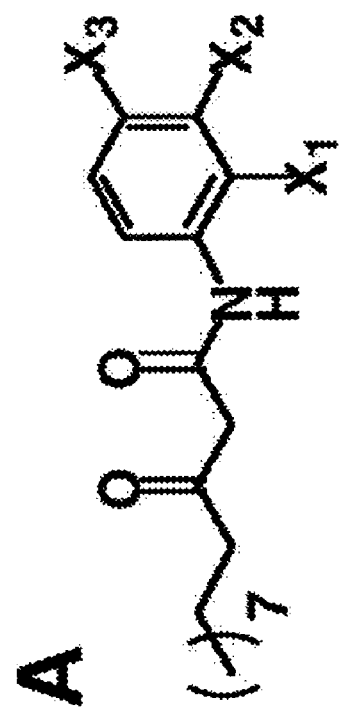

Example 14—Expansion of the 3-oxo-$C_{12}$ Library Based on 2-aminophenol or Other Aniline Derivatives It has been determined that 3-oxo-$C_{12}$-D10 is more potent than 3 for las circuit inhibition. It has also been determined from the library screening that some other substituted aniline compounds possibly antagonize the las circuit. Therefore, the library will be expanded with various anilines, particularly ortho- and meta-substituted anilines (FIG. 21A). Also, expansion of ring size will be examined (FIG. 21B).

Because a number of anilines are commercially available, the library can be initially constructed from the commercial molecules. Again, either solid phase as in FIG. 2 or solution phase using a solid-immobilized dicarbodiimide reagent to carry on the coupling can be used. The remaining procedure is the same as described above.

Example 15—Synthesis and Screening of Libraries for the rhl Quorum Sensing Circuit Although the las circuit is the master regulatory system for QS, the above results indicate that the inhibition of both circuits may be critical to shut down the entire QS system to see the same effectiveness as the genetic knockout QS strains. This working hypothesis leads to the construction of a library for the rhl circuit, i.e. $C_4$-side chain library.

Figure 13:
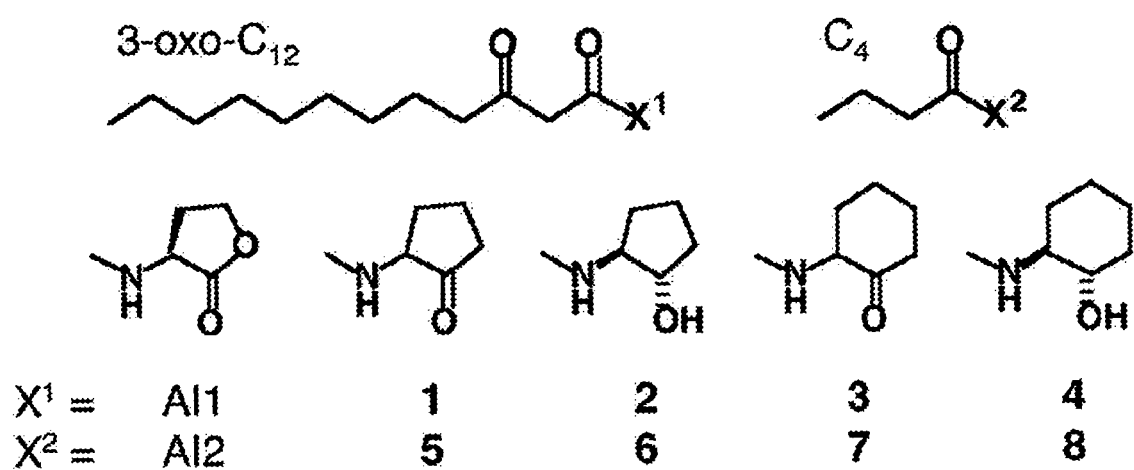
FIG. 13 shows the chemical structures of autoinducers and analogs. AI1, 3-oxo-$C_{12}$HSL; AI2, $C_4$ HSL; 1, 3-oxo-$C_{12}$-(2-aminocyclopentanone); 2, 3-oxo-$C_{12}$-(2-aminocyclopentanol); 3, 3-oxo-$C_{12}$-(2-aminocyclohexanone); 4 (formerly called 3-oxo-$C_{12}$-D12 in FIG. 5), 3-oxo-$C_{12}$-(2-aminocyclohexanol); 5, $C_4$-(2-aminocyclopentanone), 6, $C_4$-(2-aminocyclopentanol); 7, $C_4$-(2-aminocyclohexanone); 8, $C_4$-(2-aminocyclohexanol).

Unfortunately, the molecules in the $C_4$-focused library constructed in FIG. 13 did not antagonize the rhl QS circuit. However, the studies shown in FIG. 14 indicated that the microenvironment in the autoinducer binding sites of LasR and RhlR is slightly different. This finding in turn indicates that the structural elements that antagonize LasR may not be able to antagonize RhlR strongly. Thus it is necessary to construct $C_4$-libraries and screen for rhl antagonists. To this end, a $C_4$-library similar to the original 3-oxo-$C_{12}$-library (FIG. 4) has been constructed. The synthesis of such a library is accomplished by coupling various amines with butyric chloride under aqueous basic conditions or anhydrous DMAP-$Et_3N$ conditions.

High throughput screening can be carried out for agonists and antagonists using the rhl reporter. For the antagonist assay, 1 µM AI1 and 10 µM AI2 can be used to compete for the rhl-controlled GFP expression, since this concentration likely mimics well the wild-type situation.

Once hits for antagonist activity from the library are identified, the double antagonist competing conditions using 3-oxo-$C_{12}$-D10 and the $C_4$-antagonist in the presence of AI1 and AI2 can be used. The ability to attenuate pathogenicity and biofilm formation will be further evaluated with a combination of antagonists of both circuits.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. An isolated autoinducer agonist or antagonist compound having the structure

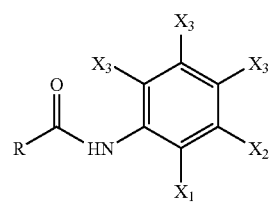

wherein $X_2$ and $X_3$ are independently selected from the group consisting of H, OH, SH, $OR^1$, $SR^1$, $NH^2$, $NHR^1$, $NR^1R^1$, $COOR^1$, alkyl, cycloalkyl, alkenyl, alkynyl, aryl, heteroaryl, heteroalicyclic, carbonyl, cyano, nitro, and halogen; when adjacent $X_2$ and $X_3$ substituents are combined, the combination forms a cycloalkyl of 3 to 8 carbon atoms, a heterocycloalkyl of 3 to 8 members comprising carbon atoms and from 1 to 6 heteroatoms selected from the group consisting of N, S, and O, and an aryl or heteroaryl ring having 3 to 8 members, wherein $R^1$ and $R^2$ are selected from the group consisting of H, alkyl, cycloalkyl, alkenyl, aryl, heteroaryl, carbonyl, and sulfonyl, and wherein R is selected from the group consisting of

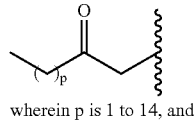
wherein p is 1 to 14, and

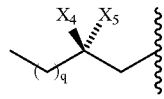

wherein q is 1 to 14, $X_4$ is OH, $NH_2$, or SH and $X_5$ is H, or $X_4$ is H and $X_5$ is OH, $NH_2$, or SH, wherein the compound has autoinducer agonist or antagonist activity.

2. The autoinducer agonist or antagonist according to claim 1 comprising an autoinducer antagonist having the structure

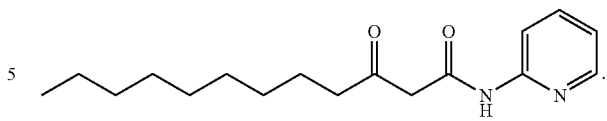

3. The autoinducer agonist or antagonist according to claim 1, wherein the autoinducer is produced by an organism selected from the group consisting of *Pseudomonas aeruginosa, Aeromonas hydrophilia, Aeromonas salmonicida, Yersinia pseudotuberculosis, Helicobacter pylori, Agrobacterium tumefaciens, Vibrio fischeri, Vibrio harveyi, Erwinia carotovora, Rhizobium leguminosarum, Rhodobacter sphaeroides,* and *Escherichia coli.*

4. The autoinducer agonist or antagonist according to claim 3, wherein the autoinducer is a *Pseudomonas aeruginosa* autoinducer.

* * * * *

UNITED STATES PATENT AND TRADEMARK OFFICE
CERTIFICATE OF CORRECTION

PATENT NO. : 7,498,292 B2  Page 1 of 1
APPLICATION NO. : 10/637940
DATED : March 3, 2009
INVENTOR(S) : Suga et al.

It is certified that error appears in the above-identified patent and that said Letters Patent is hereby corrected as shown below:

At claim 1, column 52, lines 47-57, delete the following chemical structure:

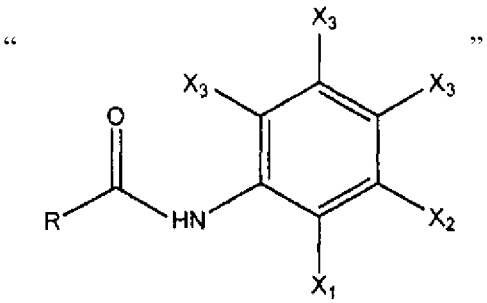

and insert the correct chemical structure:

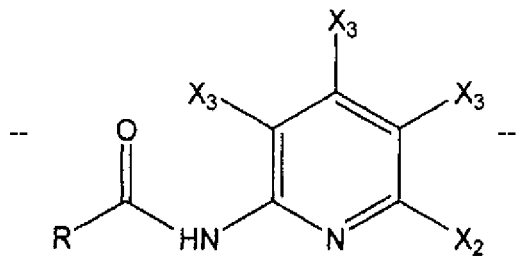

Signed and Sealed this

Twenty-sixth Day of May, 2009

JOHN DOLL
*Acting Director of the United States Patent and Trademark Office*